United States Patent
Dack et al.

(10) Patent No.: US 6,495,568 B1
(45) Date of Patent: Dec. 17, 2002

(54) HYDROXAMIC ACID DERIVATIVES AS MATRIX METALLOPROTEASE (MMP) INHIBITORS

(75) Inventors: Kevin Neil Dack; Gavin Alistair Whitlock, both of Sandwich (GB)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/423,359

(22) PCT Filed: Oct. 9, 1998

(86) PCT No.: PCT/EP98/06640

§ 371 (c)(1),
(2), (4) Date: Oct. 12, 2001

(87) PCT Pub. No.: WO99/29667

PCT Pub. Date: Jun. 17, 1999

(30) Foreign Application Priority Data

Dec. 5, 1997 (GB) .............................................. 9725782

(51) Int. Cl.$^7$ ...................... A61K 31/445; A61K 31/44; C07D 401/10; C07D 211/22
(52) U.S. Cl. ........................ 514/318; 514/210; 514/212; 514/314; 514/316; 514/320; 514/321; 514/326; 514/331; 514/332; 514/336; 514/357; 514/422; 514/428; 540/355; 540/596; 540/597; 540/602; 540/603; 540/609; 546/173; 546/174; 546/175; 546/191; 546/193; 546/196; 546/197; 546/205; 546/207; 546/256; 546/264; 546/268.1; 546/279.7; 546/280.1; 546/281.7; 546/282.1; 546/284.1; 546/339; 548/567
(58) Field of Search ................................. 514/210, 212, 514/314, 316, 318, 320, 321, 326, 331, 332, 336, 357, 422, 428; 540/355, 596, 597, 602, 603, 609; 546/191, 193, 196, 197, 205, 207, 256, 264, 268.1, 279.7, 280.1, 281.7, 282.1, 284.1, 339, 173, 174, 175; 548/567

(56) References Cited

U.S. PATENT DOCUMENTS 5,646,167 A * 7/1997 MacPherson et al. ....... 514/357
5,665,719 A * 9/1997 Bock et al. ............... 514/227.8
6,090,852 A * 7/2000 Dack et al. ................. 514/575
6,172,057 B1 * 1/2001 Benkatesan et al. ... 514/212.01

FOREIGN PATENT DOCUMENTS

| EP | 0930367 | * | 7/1999 |
| WO | 9837877 | | 9/1998 |
| WO | 9838163 | | 9/1998 |

* cited by examiner

Primary Examiner—Celia Chang
(74) Attorney, Agent, or Firm—Charles W. Ashbrook

(57) ABSTRACT

Compounds of formula (I):

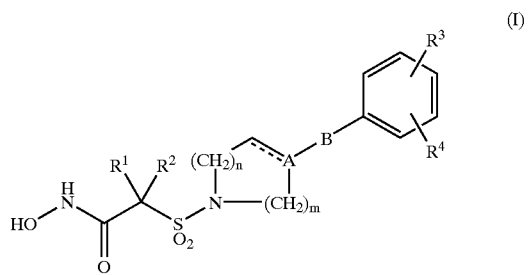

or pharmaceutically or veterinarily acceptable salts thereof, or pharmaceutically or veterinarily acceptable solvates of either entity, wherein the broken line represents an optional bond; A is C or CH; B is $CH_2$, O or absent; $R^1$ and $R^2$ are each independently selected from hydrogen, $C_1$ to $C_6$ alkyl optionally substituted with $C_1$ to $C_4$ alkoxy or phenyl, and $C_1$ to $C_6$ alkenyl; or, together with the carbon atom to which they are attached, form a $C_3$ to $C_6$ cycloalkyl group which optionally incorporates a heteroatom linkage selected from O, SO, $SO_2$ and $NR^6$ or which is optionally benzo-fused; $R^3$ is hydrogen, halo, $R^7$ or $OR^7$; $R^4$ is hydrogen, $C_1$ to $C_4$ alkyl, $C_1$ to $C_4$ alkoxy, trifluoromethyl or halo; $R^6$ is hydrogen or $C_1$ to $C_4$ alkyl; $R^7$ is an optionally substituted monocyclic or bicyclic ring system; m is 1 or 2; and n is 0, 1 or 2; with the proviso that B is not O when A is C; are MMP inhibitors useful in the treatment of, inter alia, tissue ulceration, wound repair and skin diseases.

16 Claims, No Drawings

HYDROXAMIC ACID DERIVATIVES AS MATRIX METALLOPROTEASE (MMP) INHIBITORS

This application is the U.S. national stage of PCT/EP98/06640, which has an international filing date of Oct. 9, 1998, and which claims priority from GB 9725782.8, which was filed on Dec. 5, 1997.

This invention relates to a series of substituted α-aminosulphonyl-acetohydroxamic acids which are inhibitors of zinc-dependent metalloprotease enzymes. In particular, the compounds are inhibitors of certain members of the matrix metalloprotease (MMP) family.

Matrix metalloproteases (MMPs) constitute a family of structurally similar zinc-containing metalloproteases, which are involved in the remodelling and degradation of extracellular matrix proteins, both as part of normal physiological processes and in pathological conditions. Since they have high destructive potential, MMPs are usually under close regulation and failure to maintain MMP regulation may be a component of a number of diseases and pathological conditions, including atherosclerotic plaque rupture, heart failure, restenosis, periodontal disease, tissue ulceration, wound repair, cancer metastasis, tumour angiogenesis, age-related macular degeneration, fibrotic disease, rheumatoid arthritis, osteoarthritis and inflammatory diseases dependent on migratory inflammatory cells.

Another important function of certain MMPs is to activate various enzymes, including other MMPs, by cleaving the pro-domains from their protease domains. Thus some MMPs act to regulate the activities of other MMPs, so that over-production of one MMP may lead to excessive proteolysis of extracellular matrix by another. Moreover, MMPs have different substrate preferences (shown in the following Table for selected family members) and different functions within normal and pathological conditions. For recent reviews of MMPs, see Current Pharmaceutical Design, 1996, 2, 624 and Exp. Opin. Ther. Patents, 1996, 6, 1305.

TABLE

| Enzyme | Other Names | Preferred Substrates |
|---|---|---|
| MMP-1 | collagenase-1; interstitial collagenase | collagens I, II, III, VII, X; gelatins |
| MMP-2 | gelatinase A; 72kDa gelatinase | gelatins; collagens IV, V, VII, X; elastin; fibronectin; activates pro-MMP-13 |
| MMP-3 | stromelysin-1 | proteoglycans; laminin; fibronectin; gelatins |
| MMP-8 | collagenase-2; neutrophil collagenase | collagens I, II, III |
| MMP-9 | gelatinase B; 92kDa gelatinase | gelatins; collagens IV, V; elastin |
| MMP-13 | collagenase-3 | collagens I, II, III; gelatins |
| MMP-14 | MT-MMP-1 | activates pro-MMP-2 & 13; gelatins |

Excessive production of MMP-3 is thought to be responsible for pathological tissue breakdown which underlies a number of diseases and conditions. For example, MMP-3 has been found in the synovium and cartilage of osteoarthritis and rheumatoid arthritis patients, thus implicating MMP-3 in the joint damage caused by these diseases: see Biochemistry, 1989, 28, 8691 and Biochem. J., 1989, 258, 115. MMP-13 is also thought to play an important role in the pathology of osteoarthritis and rheumatoid arthritis: see Lab. Invest., 1997, 76, 717 and Arthritis Rheum., 1997, 40, 1391. The compounds of the present invention inhibit both MMP-3 and MMP-13 and thus may be of utility in treating these diseases.

The over-expression of MMP-3 is also thought to be responsible for much of the tissue damage and chronicity of chronic wounds, such as venous ulcers, diabetic ulcers and pressure sores: see Brit. J. Dermatology, 1996, 135, 52.

Furthermore, the production of MMP-3 may also cause tissue damage in conditions where there is ulceration of the colon (as in ulcerative colitis and Crohn's disease: see J. Immunol., 1997 158, 1582 and J. Clin. Pathol., 1994, 47, 113) or of the duodenum (see Am. J. Pathol., 1996, 148, 519).

Moreover, MMP-3 may also be involved in skin diseases such as dystrophic epidermolysis bullosa (see Arch. Dermatol. Res., 1995, 287, 428) and dermatitis herpetiformis (see J. Invest. Dermatology, 1995, 105, 184).

Finally, rupture of atherosclerotic plaques by MMP-3 may lead to cardiac or cerebral infarction: see Circulation, 1997, 96, 396. Thus, MMP-3 inhibitors may find utility in the prevention of heart attack and stroke.

Studies of human cancers have shown that MMP-2 is activated on the invasive tumour cell surface (see J. Biol.Chem., 1993, 268, 14033) and BB-94, a non-selective peptidic hydroxamate MMP inhibitor, has been reported to decrease the tumour burden and prolong the survival of mice carrying human ovarian carcinoma xenografts (see Cancer Res., 1993, 53, 2087). Certain compounds of the present invention inhibit MMP-2 and therefore may be useful in the treatment of cancer metastasis and tumour angiogenesis.

Various series of MMP inhibitors have appeared in the patent literature. For example, α-arylsulphonamido-substituted acetohydroxamic acids are disclosed in EP-A-0606046, WO-A-9627583 and WO-A-9719068, whilst EP-A-0780386 discloses certain related sulphone-substituted hydroxamic acids.

The compounds of the present invention are inhibitors of some of the members of the MMP family. In particular, they are potent inhibitors of MMP-3 and MMP-13, with certain compounds exhibiting varying degrees of selectivity over other MMPs, such as MMP-1, MMP-2 and MMP-9. Certain of the compounds are potent MMP-2 inhibitors.

Thus, according to the present invention, there is provided a compound of formula (I):

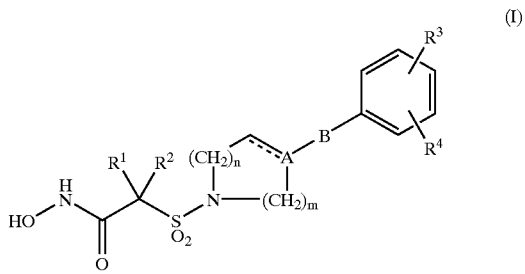

or a pharmaceutically or veterinarily acceptable salt thereof, or a pharmaceutically or veterinarily acceptable solvate (including hydrate) of either entity,
wherein
the broken line represents an optional bond;
A is C or CH;
B is $CH_2$, O or absent;
$R^1$ and $R^2$ are each independently selected from hydrogen, $C_1$ to $C_6$ alkyl optionally substituted with $C_1$ to $C_4$ alkoxy or phenyl, and $C_1$ to $C_6$ alkenyl; or, together with the carbon atom to which they are attached, form a $C_3$ to $C_6$ cycloalkyl group which optionally incorporates a heteroatom linkage selected from O, SO, $SO_2$ and NR⁶ or which is optionally benzo-fused;

R³ is hydrogen, halo, R⁷ or OR⁷;

R⁴ is hydrogen, $C_1$ to $C_4$ alkyl, $C_1$ to $C_4$ alkoxy, trifluoromethyl or halo;

R⁶ is hydrogen or $C_1$ to $C_4$ alkyl;

R⁷ is a monocyclic or bicyclic ring system selected from phenyl, thienyl, furyl, pyridinyl, pyrimidinyl, naphthyl, indanyl, benzothienyl, benzofuranyl, 2,3-dihydrobenzofuranyl, indolyl, quinolinyl, isoquinolinyl, benzodioxolyl, benzimidazolyl, benzoxazolyl, benzothiazolyl and benzodioxanyl, any of which ring systems is optionally substituted with one or two substituents selected from $C_1$ to $C_4$ alkyl optionally substituted with $C_1$ to $C_4$ alkoxy or hydroxy, $C_1$–$C_4$ alkoxy optionally substituted with $C_1$ to $C_4$ alkoxy or hydroxy, $C_1$ to $C_4$ alkylthio, trifluoromethyl, trifluoromethoxy, halo and cyano;

m is 1 or 2; and n is 0, 1 or 2;

with the proviso that B is not O when A is C.

In the above definition, unless otherwise indicated, alkyl, alkoxy, alkylthio and alkenyl groups having three or more carbon atoms may be straight chain or branched chain. Halo means fluoro, chloro, bromo or iodo.

The compounds of formula (I) may contain one or more chiral centres and therefore can exist as stereoisomers, i.e. as enantiomers or diastereoisomers, as well as mixtures thereof. The invention includes both the individual stereoisomers of the compounds of formula (I) and any mixture thereof. Separation of diastereoisomers may be achieved by conventional techniques, e.g. by fractional crystallisation or chromatography (including HPLC) of a diastereoisomeric mixture of a compound of formula (I) or a suitable salt or derivative thereof. An individual enantiomer of a compound of formula (I) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active base or acid.

Furthermore, compound of formula (I) which contain alkenyl groups can exist as cis-stereoisomers or trans-stereoisomers. Again, the invention includes both the separated individual stereoisomers as well as mixtures thereof.

Also included in the invention are radiolabelled derivatives of compounds of formula (I) which are suitable for biological studies.

Compounds of formulae (I) may provide pharmaceutically or veterinarily acceptable base salts, in particular non-toxic alkali metal salts, with bases. EXAMPLEs include the sodium and potassium salts. The pharmaceutically or veterinarily acceptable salts of the compounds of formula (I) which contain a basic centre are, for example, non toxic acid addition salts formed with inorganic acids such as hydrochloric, hydrobromic, sulphuric and phosphoric acid, with organo-carboxylic acids, or with organo-sulphonic acids.

A preferred group of compounds of formula (I) is that wherein B is absent; R¹ is hydrogen, $C_1$ to $C_4$ alkyl optionally substituted with methoxy or phenyl, or $C_1$ to $C_5$ alkenyl; R² is hydrogen or $C_1$ to $C_4$ alkyl; or R¹ and R², together with the carbon atom to which they are attached, form a $C_4$ to $C_5$ cycloalkyl group which optionally incorporates a heteroatom linkage selected from O and NR⁶ or which is optionally benzo-fused; R³ is selected from 4-phenyl, 4-pyridinyl, 4-(indan-5-yl), 4-(2,3-dihydrobenzofuran-5-yl), 4-(quinolin-3-yl), 4-(benzodioxol-5-yl) and 4-(benzimidazol-5-yl), any of which is optionally substituted with one or two substituents selected from $C_1$ to $C_3$ alkyl optionally substituted with methoxy or hydroxy, $C_1$ to $C_3$ alkoxy optionally substituted with methoxy or hydroxy, methylthio, trifluoromethyl, trifluoromethoxy, fluoro, chloro and cyano; R⁴ is hydrogen, methyl, ethyl, methoxy, trifluoromethyl, fluoro or chloro; R⁶ is methyl; m is 2; and n is 1.

A more preferred group of compounds of formula (I) is that wherein R¹ is hydrogen, methyl, ethyl, 2-methylprop-1-yl, but-1-yl, 2-methoxyethyl, benzyl, 3-phenylprop-1-yl, allyl, 2-methylallyl, 3,3-dimethylallyl; R² is hydrogen, methyl or ethyl; or R¹ and R², together with the carbon atom to which they are attached, form a cyclobutyl, cyclopentyl, tetrahydropyran-4,4-diyl, 1-methylpiperidin-4,4-diyl or indan-2,2-diyl group; R³ is 4-phenyl, 4-(2-methylphenyl), 4-(3-methylphenyl), 4-(3-ethylphenyl), 4-[3-(prop-2-yl) phenyl], 4-(3,5-dimethylphenyl), 4-(3-methoxymethylphenyl), 4-(3-hydroxymethylphenyl), 4-(2-methoxyphenyl), 4-(3-methoxyphenyl), 4-(3-ethoxyphenyl), 4-(4-ethoxyphenyl), 4-[3-(prop-1-oxy) phenyl], 4-[3-(prop-2-oxy)phenyl], 4-[4-(prop-2-oxy) phenyl], 4-(3,4-dimethoxyphenyl), 4-[3-(2-methoxyethoxy) phenyl], 4-[3-(2-hydroxyethoxy)phenyl], 4-(3-methylthiophenyl), 4-(3-trifluoromethylphenyl), 4-(3-trifluoromethoxyphenyl), 4-(2-fluorophenyl), 4-(3-chloro-4-fluorophenyl), 4-(3-cyanophenyl), 4-(pyridin-2-yl), 4-(pyridin-3-yl), 4-(pyridin4-yl), 4-(6-ethoxypyridin-2-yl), 4-(5-ethoxypyridin-3-yl), 4-(indan-5-yl), 4-(2,3-dihydrobenzofuran-5-yl), 4-(quinolin-3-yl), 4-(benzodioxol-5-yl), 4-(2,2-dimethylbenzodioxol-5-yl) and 4-(1,2-dimethylbenzimidazol-5-yl); and R⁴ is hydrogen, 2-methyl, 3-methyl, 3-ethyl, 3-methoxy, 3-trifluoromethyl, 3-fluoro or 3-chloro.

A particularly preferred group of compounds of formula (I) is that wherein R¹ and R² are both hydrogen or methyl or, together with the carbon atom to which they are attached, form a cyclobutyl, cyclopentyl, tetrahydropyran-4,4-diyl or 1-methylpiperidin-4,4-diyl group; R³ is 4-phenyl, 4-(3-methoxyphenyl), 4-(3-ethoxyphenyl), 4-[3-(2-methoxyethoxy)phenyl], 4-[3-(2-hydroxyethoxy)phenyl] or 4-(6-ethoxypyridin-2-yl); and R⁴ is 3-methyl or 3-methoxy.

Especially preferred individual compounds of the invention include

N-hydroxy-2-{4-[4-(3-ethoxyphenyl)-3-methylphenyl]-1,2,3,6-tetrahydropyridin-1-ylsulphonyl}acetamide;

N-hydroxy-2-{4-[4-(3-ethoxyphenyl)-3-methylphenyl]-1,2,3,6-tetrahydropyridin-1-ylsulphonyl}-2-methylpropanamide;

N-hydroxy-2-{4-[4-(3-ethoxyphenyl)-3-methylphenyl] piperidin-1-ylsulphonyl}-2-methylpropanamide;

N-hydroxy-1-{4-[4-(3-methoxyphenyl)-3-methylphenyl] piperidin-1-ylsulphonyl}cyclopentanecarboxamide;

N-hydroxy-1-{4-[4-(3-methoxyphenyl)-3-methylphenyl] piperidin-1-ylsulphonyl}cyclobutanecarboxamide;

N-hydroxy-2-{4-[4-(3-ethoxyphenyl)-3-methoxyphenyl] piperidin-1-ylsulphonyl}-2-methylpropanamide;

N-hydroxy-2-{4-[4-(6-ethoxypyridin-2-yl)-3-methylphenyl]piperidin-1-ylsulphonyl}-2-methylpropanamide;

N-hydroxy-2-{4-[4-(3-[2-methoxyethoxy]phenyl)-3-methylphenyl]-piperidin-1-ylsulphonyl}-2-methylpropanamide; and N-hydroxy-2-{4-[4-(3-[2-hydroxyethoxy]phenyl)-3-methylphenyl]piperidine-1-ylsulphonyl}-2-methylpropanamide.

In a further aspect, the present invention provides processes for the preparation of a compound of formula (I), or a pharmaceutically or veterinarily acceptable salt thereof, or a pharmaceutically or veterinarily acceptable solvate (including hydrate) of either entity, as illustrated below.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

Illustrative of protecting group strategies are the synthetic routes to EXAMPLE 64, in which an O-benzyl protected hydroxamate is formed prior to the required Suzuki reaction step, and to EXAMPLE 66, in which alcohol protection using a t-butyldiphenylsilyl group is employed.

It will also be appreciated that various standard substituent or functional group interconversions and transformations within certain compounds of formula (I) will provide other compounds of formula (I). An example is the conversion of the tetrahydropyridine derivative (EXAMPLE 28) to the piperidine derivative (EXAMPLE 29) by hydrogenation.

The following processes are illustrative of the general synthetic procedures which may be adopted in order to obtain the compounds of the invention.

A compound of formula (I) may be prepared directly from an ester of formula (II):

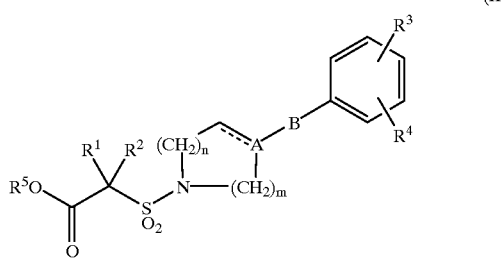

(II)

wherein $R^5$ is $C_1$ to $C_3$ alkyl, and the broken line, A,B, $R^1$, $R^2$, $R^3$, $R^4$, m and n are as previously defined for formula (I), or via the intermediacy of the corresponding carboxylic acid of formula (II) wherein $R^5$ is hydrogen.

When prepared directly from an ester of formula (II), the reaction may be carried out by treatment of the ester with up to a 3-fold excess of hydroxylamine in a suitable solvent at from about room temperature to about 85° C. The hydroxylamine is conveniently generated in situ from its hydrochloride salt by conducting the reaction in the presence of a molar equivalent amount of a suitable base such as an alkali metal carbonate or bicarbonate, e.g. potassium carbonate. Preferably the solvent is methanol, optionally combined with tetrahydrofuran or dichloromethane as co-solvent, and the reaction temperature is from about 65 to 70° C.

Alternatively, the ester may be converted by conventional hydrolysis to the corresponding carboxylic acid which is then transformed to the required hydroxamic acid of formula (I).

Preferably the hydrolysis is effected under basic conditions using up to about a 6-fold excess of an alkali metal hydroxide in aqueous solution, optionally in the presence of a co-solvent, at from about room temperature to about 85° C. Typically the co-solvent is selected from methanol, 1,4-dioxan, a mixture of methanol and tetrahydrofuran and a mixture of methanol and 1,4-dioxan and the reaction temperature is from about 40 to about 70° C.

The subsequent coupling step may be achieved using conventional amide-bond forming techniques, e.g. via the acyl chloride derivative and hydroxylamine hydrochloride in the presence of an excess of a tertiary amine such as triethylamine or pyridine to act as acid-scavenger, optionally in the presence of a catalyst such as 4-dimethylaminopyridine, in a suitable solvent such as dichloromethane, at from about 0° C. to about room temperature. For convenience, pyridine may also be used as the solvent.

In particular, any one of a host of amino acid coupling variations may be used. For example, the acid of formula (II) wherein $R^5$ is hydrogen may be activated using a carbodiimide such as 1,3-dicyclohexylcarbodiimide or 1-ethyl-3-(3dimethylaminoprop-1-yl)carbodiimide optionally in the presence of 1-hydroxybenzotriazole and/or a catalyst such as 4-dimethylaminopyridine, or by using a halotrisaminophosphonium salt such as bromotris(pyrrolidino)-phosphonium hexafluorophosphate. Either type of coupling is conducted in a suitable solvent such as dichloromethane or dimethylformamide, optionally in the presence of a tertiary amine such as N-methylmorpholine or N-ethyidiisopropylamine (for example when either the hydroxylamine or the activating reagent is presented in the form of an acid addition salt), at from about 0° C. to about room temperature. Typically, from 1.1 to 2.0 molecular equivalents of the activating reagent and from 1.0 to 4.0 molecular equivalents of any tertiary amine present are employed.

A preferred reagent for mediating the coupling reaction is O-(7-azabenzotriazol-1-yl)-1,1,3,3-tetramethyluronium hexafluorophosphate (HATU).

Preferably a solution of the acid and from 1.0 to 1.2 molecular equivalents of N-ethyidiisopropylamine in a suitable solvent such as anhydrous dimethylformamide or anhydrous 1-methylpyrrolidin-2-one, under nitrogen, is treated with up to a 50% excess of HATU at about room temperature followed, after about 15 to 30 minutes, with up to about a 3-fold excess of hydroxylamine hydrochloride and up to about a 4-fold excess of N-ethyldiisopropylamine, optionally in the same solvent, at the same temperature.

An ester of formula (II) may be prepared from an amine of formula (III):

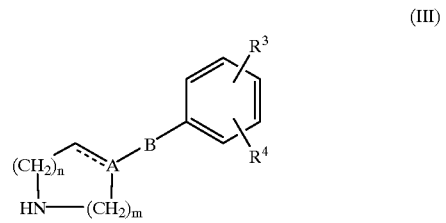

(III)

wherein the broken line, A,B, $R^3$, $R^4$, m and n are as previously defined for formula (II), by sulphonylation with a compound of formula (IV):

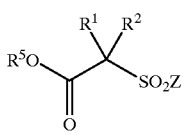

wherein Z is halo, $R^5$ is $C_1$ to $C_3$ alkyl and $R^1$ and $R^2$ are as previously defined for formula (II). Preferably, Z is chloro.

When $R^6$ is hydrogen, it will normally be advantageous to protect this secondary amino linkage with a conventional amine protecting group.

The reaction may be effected in the presence of up to a 50% excess of an appropriate base in a suitable solvent at from about 0° C. to about room temperature. For example, when both $R^1$ and $R^2$ are hydrogen, an appropriate base is 1,8-diazabicyclo[5.4.0]undec-7-ene and a suitable solvent is dichloromethane.

Alternatively, the anion of (III) may be generated initially using up to a 20% excess of a strong base in a suitable solvent, under nitrogen, and then the sulphonylation with from 1.0 to 1.2 molecular equivalents of (IV) effected.

Conveniently, such a coupling may be carried out at room temperature with N,O-bis(trimethylsilyl)acetamide as base and anhydrous tetrahydrofuran as solvent.

Further routes to the preparation of an ester of formula (II), wherein $R^3$ is $R^7$, rely on exploitation of either a Suzuki reaction or a Stille reaction with an ester of formula (II) wherein $R^3$ (but not $R^4$) is either bromo or iodo.

Thus, in the Suzuki reaction, the latter ester is treated with from 1.0 to 1.5 molecular equivalents of a boronic acid of formula $R^7B(OH)_2$, in the presence of from 2.0 to 3.0 molecular equivalents of an alkali metal fluoride, about 0.1 molecular equivalents of a triarylphosphine and about 0.05 molecular equivalents of a palladium catalyst in a suitable solvent, under nitrogen, at from about 65 to about 100° C. Typically, the fluoride is cesium fluoride, the phosphine is tri-o-tolylphosphine, the catalyst is tris(dibenzylideneacetone)-dipalladium(0) and the solvent is degassed 1,2-dimethoxyethane optionally with 1-methylpyrrolidin-2-one as co-solvent.

In the Stille reaction, the aforementioned ester starting material of formula (II) is treated with from 1.0 to 2.0 molecular equivalents of a suitable trialkylstannane derivative of formula $R^7Sn(alkyl)_3$ wherein alkyl is, for example, n-butyl, in the presence of from 2.0 to 3.0 molecular equivalents of a tertiary base, from 0.3 to 0.6 molecular equivalents of a triarylphosphine and from 0.05 to 0.2 molecular equivalents of a palladium catalyst in a suitable solvent, under nitrogen, at from about 65 to about 100° C. Typically, the base is triethylamine, the phosphine is tri-o-tolylphosphine, the catalyst is palladium(II) acetate optionally in the presence of tetrakis(triphenylphosphine) palladium(0) and the solvent is anhydrous acetonitrile.

Certain esters of formula (II) wherein at least one of $R^1$ and $R^2$ is other than hydrogen may be conveniently obtained from the α-carbanion of an ester of formula (II) wherein at least one of $R^1$ and $R^2$ is hydrogen by conventional C-alkylation procedures using an alkylating agent of formula (VA) or (VB):

RX                                                         (VA)

X-W-Y                                         (VB)

wherein R is as previously defined for $R^1$ or $R^2$ but is not hydrogen, X and Y may be the same or different and are suitable leaving groups, and W is a $C_2$ to $C_5$ alkylene group which optionally incorporates a heteroatom linkage selected from O, SO, $SO_2$ and $NR^6$ or which is optionally benzofused. When $R^6$ is to be hydrogen in a compound of formula (I), then a conventional amine protecting group strategy may be of advantage during this alkylation procedure.

A suitable leaving group may be selected from halo (e.g. chloro, bromo or iodo), $C_1$–$C_4$ alkanesulphonyloxy, trifluoromethanesulphonyloxy and arylsulphonyloxy (e.g. benzenesulphonyloxy or p-toluenesulphonyloxy).

Preferably, X and Y are selected from bromo, iodo and p-toluenesulphonyloxy.

The carbanion may be generated using an appropriate base in a suitable solvent. Typical base-solvent combinations may be selected from lithium, sodium or potassium hydride, lithium, sodium or potassium bis(trimethylsilyl)amide, lithium diisopropylamide and butyllithium, together with toluene, ether, 1,2-dimethoxyethane, tetrahydrofuran, 1,4-dioxan, dimethylformamide, N,N-dimethylacetamide, 1-methylpyrrolidin-2-one and any mixture thereof.

Preferably the base is sodium hydride and the solvent is anhydrous dimethylformamide, optionally with anhydrous tetrahydrofuran as co-solvent, or anhydrous 1-methylpyrrolidin-2-one. For monoalkylation, up to about a 10% excess of base is employed whilst, for dialkylation, from about 2 to about 3 molar equivalents are generally appropriate.

Typically, the carbanion is generated at about room temperature, under nitrogen, and subsequently treated with up to about a 30% excess of the required alkylating agent at the same temperature.

Clearly, when dialkylation is required and $R^1$ and $R^2$ are different, the substituents may be introduced in tandem in a "one-pot reaction" or in separate steps.

A particularly convenient, alternative alkylation method involves treatment of the substrate with the required alkylating agent in the presence of from 3.0 to 3.5 molecular equivalents of anhydrous potassium carbonate in anhydrous dimethyl sulphoxide or anhydrous 1,2-dimethoxyethane, under nitrogen, at about room temperature.

Clearly, an alternative variation for preparing a compound of formula (II) is to introduce $R^1$ and/or $R^2$ into a suitable bromo or iodo intermediate before further elaboration via, for example, a Suzuki or Stille reaction.

An amine of formula (III) may be obtained by standard chemical procedures. For example, when B is absent, m is 2 and n is 1, a suitably N-protected piperidin-4-one of formula (VI):

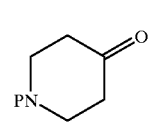

wherein P is a conventional amine protecting group, is reacted with a carbanion derivative of a compound of formula (VII):

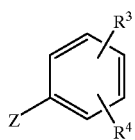

(VII)

wherein Z is as previously defined for formula (IV) and $R^3$ and $R^4$ are as previously defined for formula (III), to provide a compound of formula (VIII):

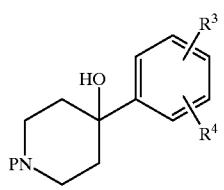

(VIII)

Preferably, Z is chloro, bromo or iodo.

Conveniently (VII) is converted to an aryllithium or aryl Grignard derivative whilst, of the plethora of amine protecting groups available, P is typically t-butoxycarbonyl (Boc) or benzyl.

When P is Boc, (VIII) may be transformed directly to a compound of formula (III), wherein the broken line represents a bond, A is C, B is absent, m is 2, n is 1 and $R^3$ and $R^4$ are as previously defined for formula (III), using trifluoroacetic acid optionally in a suitable solvent such as dichloromethane at about room temperature. Alternatively, when P is benzyl, (VIII) may be converted in two steps to the same compound of formula (III). For example, in the first step, dehydration may be effected in refluxing toluene using p-toluenesulphonic acid and a Dean-Stark apparatus. N-Deprotection of the resulting alkene (1,2,3,6-tetrahydropyridine derivative), in the second step, may be achieved using 1-chloroethyl chloroformate in refluxing toluene followed by treatment of the reaction mixture, at room temperature, with either methanol or ethanol.

This unsaturated piperidine may be converted to a compound of formula (III) wherein the broken line does not represent a bond, A is CH, B is absent, m is 2, n is 1 and $R^3$ and $R^4$ are as previously defined for formula (III) under conventional catalytic, or catalytic transfer, hydrogenation conditions. Alternatively, these hydrogenation conditions may be employed to convert the previously described N-benzyl alkene (1,2,3,6-tetrahydropyridine derivative) to the same piperidine derivative, directly in one step. Furthermore, this fully saturated piperidine is also available in one step from (VIII) when P is Boc by standard ionic hydrogenation using, for example, triethylsilane and trifluoroacetic acid in dichloromethane.

Other amines of formula (III), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the EXAMPLEs and Preparations sections which allow the compounds defined by formula (I) to be obtained.

The pharmaceutically and veterinarily acceptable base salts of the compounds of formula (I) may also be prepared in a conventional manner. For example a solution of the hydroxamic acid is treated with the appropriate base, either neat or in a suitable solvent, and the resulting salt isolated either by filtration or by evaporation under vacuum of the reaction solvent. Pharmaceutically and veterinarily acceptable acid addition salts can be obtained in an analogous manner by treating a solution of a basic compound of formula (I) with the appropriate acid. Both types of salt may be formed or interconverted using ion-exchange resin techniques.

The biological activities of the compounds of the present invention were determined by the following test methods, which are based on the ability of the compounds to inhibit the cleavage of various fluorogenic peptides by MMPs 1, 2, 3, 9, 13 and 14.

The assays for MMPs 2, 3, 9 and 14 are based upon the original protocol described in FEBS, 1992, 296, 263, with the minor modifications described below.

Inhibition of MMP-1

Enzyme Preparation

Catalytic domain MMP-1 was prepared in Pfizer Central Research laboratories. A stock solution of MMP-1 (1 $\mu$M) was activiated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 $\mu$M $ZnSO_4$ and 0.05% Brij 35, pH 7.5) to a concentration of 10 nM. The final concentration of enzyme used in the assay was 1 nM.

Substrate

The fluorogenic substrate used in this assay was Dnp-Pro-$\beta$-cyclohexyl-Ala-Gly-Cys(Me)-His-Ala-Lys-(N-Me-Ala)-$NH_2$ as originally described in Anal. Biochem., 1993, 212, 58. The final substrate concentration used in the assay was 10 $\mu$M.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG Lab Technologies, Aylesbury, UK) at an excitation wavelength of 355 nm and emission wavelength of 440 nm. The potency of inhibition was measured from the amount of substrate cleavage obtained using a range of test compound concentrations and, from the resulting dose-response curve, an $IC_{50}$ value (the concentration of inhibitor required to inhibit 50% of the enzyme activity) was calculated.

Inhibition of MMP-2, MMP-3 and MMP-9

Enzyme Preparation

Catalytic domains MMP-2, MMP-3 and MMP-9 were prepared in Pfizer Central Research laboratories. A stock solution of MMP-2, MMP-3 or MMP-9 (1 $\mu$M) was activated by the addition of APMA. For MMP-2 and MMP-9, a final concentration of 1 mM APMA was added, followed by incubation for 1 hour at 37° C. MMP-3 was activated by the addition of 2 mM APMA, followed by incubation for 3 hours at 37° C. The enzymes were then diluted in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assays was 1 nM.

Substrate

The fluorogenic substrate used in this screen was Mca-Arg-Pro-Lys-Pro-Tyr-Ala-Nva-Trp-Met-Lys(Dnp)-NH$_2$ (Bachem Ltd., Essex, UK) as originally described in J.Biol.Chem., 1994, 269, 20952. This substrate was selected because it has a balanced hydrolysis rate against MMPs 2, 3 and 9 ($k_{cat}/k_m$ of 54,000, 59,400 and 55,300 s$^{-1}$ M$^{-1}$ respectively). The final substrate concentration used in the assay was 5 μM.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C., prior to determination of fluorescence using a fluorimeter (Fluostar; BMG Lab Technologies, Aylesbury, UK) at an excitation wavelength of 328 nm and emission wavelength of 393 nm. The potency of inhibition was measured from the amount of substrate cleavage obtained using a range of test compound concentrations and, from the resulting dose-response curve, an IC$_{50}$ value (the concentration of inhibitor required to inhibit 50% of the enzyme activity) was calculated.

Inhibition of MMP-13

Enzyme Preparation

Human recombinant MMP-13 was prepared by PanVera Corporation (Madison, Wis.) and characterised at Pfizer Central Research laboratories. A 1.9 mg/ml stock solution was activated with 2 mM APMA for 2 hours at 37° C. MMP-13 was then diluted in assay buffer (50 mM Tris, 200 mM NaCl, 5 mM CaCl$_2$, 20 μM ZnCl$_2$ and 0.02% Brij 35, pH 7.5) to a concentration of 5.3 nM. The final concentration of enzyme used in the assay was 1.3 nM.

Substrate

The fluorogenic substrate used in this screen was Dnp-Pro-Cha-Gly-Cys(Me)-His-Ala-Lys(NMA)-NH$_2$. The final substrate concentration used in the assay was 10 μM.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate. The addition of substrate to each well initiated the reaction. Fluorescence intensity was determined using a 96 well plate fluorimeter (Cytofluor II; PerSeptive Biosystems, Inc., Framingham, Mass.) at an excitation wavelength of 360 nm and emission wavelength of 460 nm. The potency of inhibition was measured from the amount of substrate cleavage obtained using a range of test compound concentrations and, from the resulting dose-response curve, an IC$_{50}$ value (the concentration of inhibitor required to inhibit 50% of the enzyme activity) was calculated.

Inhibition of MMP-14

Enzyme Preparation

Catalytic domain MMP-14 was prepared in Pfizer Central Research laboratories. A 10 μM enzyme stock solution was activated for 20 minutes at 25° C. following the addition of 5 μg/ml of trypsin (Sigma, Dorset, UK). The trypsin activity was then neutralised by the addition of 50 μg/ml of soyabean trypsin inhibitor (Sigma, Dorset, UK), prior to dilution of this enzyme stock solution in Tris-HCl assay buffer (100 mM Tris, 100 mM NaCl, 10 mM CaCl$_2$, 0.16% Brij 35, pH 7.5) to a concentration of 10 nM. The final concentration of enzyme used in the assay was 1 nM.

Substrate

The fluorogenic substrate used in this screen was Mca-Pro-Leu-Gly-Leu-Dpa-Ala-Arg-NH$_2$ (Bachem Ltd., Essex, UK) as described in J.Biol.Chem., 1996, 271, 17119.

Determination of Enzyme Inhibition

This was performed as described for MMPs 2, 3 and 9.

In human therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice.

They may be administered orally in the form of tablets containing such excipients as starch or lactose, or in capsules or ovules either alone or in admixture with excipients, or in the form of elixirs, solution or suspensions containing flavouring or colouring agents. They can also be injected, for example intravenously, intramuscularly or subcutaneously, and are best used in the form of a sterile aqueous solution which may contain other substances, for example enough salts or monosaccarides to make the solution isotonic with blood. For other routes of parenteral administration, such as buccal or sublingual, they may be administered in the form of tablets or lozenges which can be formulated in a conventional manner.

In addition, the compounds and their salts may be administered topically in the form of sterile creams, gels, suspensions, lotions, ointments, dusting powders, sprays, drug-incorporated dressings or via a skin patch. For example, they can be incorporated into a cream consisting of an aqueous or oily emulsion of polyethylene glycols or liquid paraffin, or they can be incorporated into an ointment consisting of a white wax soft paraffin base, or as a hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycol impregnated gauze dressings or with hydrogel, hydrocolloid, alginate or film dressings. Moreover, the compounds and salts may be administered intraocularly as an eye drop with appropriate buffers, viscosity modifiers (e.g. cellulose derivatives), preservatives (e.g. benzalkonium chlorides (BZK)) and agents to adjust tonicity (e.g. sodium chloride).

All such formulations may also contain stabilisers and preservatives.

Depending on the route of administration to human patients, the daily dosage level of the compounds of formula (I) and their salts may be from 0.001 to 20 mg/kg, in single or divided doses. Thus, for example, tablets or capsules could contain from 0.02 to 500 mg of active compound for administration singly or two or more at a time as appropriate.

The physician in any event will determine the actual dosage which will be most suitable for an individual patient and it will vary with the age, weight and response of the particular patient. The above dosages are exemplary of the average case; there can of course be individual instances where higher or lower dosage ranges are merited and such are within the scope of this invention.

For veterinary use, a compound of formula (I), or a veterinarily acceptable salt thereof, or a veterinarily acceptable solvate of either entity, is administered as a suitably acceptable formulation in accordance with normal veterinary practice and the veterinary surgeon will determine the dosing regimen and route of administration which will be most appropriate for a particular animal.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

It further provides a veterinary formulation comprising a compound of formula (I), or a veterinarily acceptable salt thereof, or a veterinarily acceptable solvate of either entity, together with a veterinarily acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a human medicament.

In addition, it provides a compound of formula (I), or a veterinarily acceptable salt thereof, or a veterinarily acceptable solvate of either entity, or a veterinary formulation containing any of the foregoing, for use as an animal medicament.

In yet another aspect, the invention provides the use of a compound of formula (I), or a pharmaceutically acceptable salt thereof, or a pharmaceutically acceptable solvate of either entity, for the manufacture of a human medicament for the curative or prophylactic treatment of a medical condition for which a MMP inhibitor is indicated.

It also provides the use of a compound of formula (I), or a veterinarily acceptable salt thereof, or a veterinarily acceptable solvate of either entity, for the manufacture of an animal medicament for the curative or prophylactic treatment of a medical condition for which a MMP inhibitor is indicated.

Moreover, the invention provides the use of a compound of formula (I), or a pharmaceutically acceptable salt thereof, or a pharmaceutically acceptable solvate containing either entity, for the manufacture of a human medicament for the curative or prophylactic treatment of atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells.

It also provides the use of a compound of formula (I), or a veterinarily acceptable salt thereof, or a veterinarily acceptable solvate containing either entity, for the manufacture of an animal medicament for the curative or prophylactic treatment of atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells.

Additionally, the invention provides a method of treating or preventing a medical condition for which a MMP inhibitor is indicated, in a mammal (including a human being), which comprises administering to said mammal a therapeutically effective amount of a compound of formula (I), or a pharmaceutically or veterinarily acceptable salt thereof, or a pharmaceutically or veterinarily acceptable solvate of either entity, or a pharmaceutical composition or veterinary formulation containing any of the foregoing.

Still further, the invention provides a method of treating or preventing atherosclerotic plaque rupture, myocardial infarction, heart failure, restenosis, stroke, periodontal disease, tissue ulceration, wound repair, skin diseases, cancer metastasis, tumour angiogenesis, age-related macular degeneration, fibrotic disease, rheumatoid arthritis, osteoarthritis and inflammatory diseases dependent on migratory inflammatory cells, in a mammal (including a human being), which comprises administering to said mammal a therapeutically effective amount of a compound of formula (I), or a pharmaceutically or veterinarily acceptable salt thereof, or a pharmaceutically or veterinarily acceptable solvate of either entity, or a pharmaceutical composition or veterinary formulation containing any of the foregoing.

The invention also includes any novel intermediates described herein, for example those of formula (II).

The syntheses of the compound of the invention and of the intermediates for use therein are illustrated by the following EXAMPLEs and Preparations.

Room temperature means 20 to 25° C.

Flash chromatography refers to column chromatography on silica gel (Kieselgel 60, 230–400 mesh).

Melting points are uncorrected.

$^1$H Nuclear magnetic resonance (NMR) spectra were recorded using a Bruker AC300, a Varian Unity Inova-300 or a Varian Unity Inova-400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

Mass spectra were recorded using a Finnigan Mat. TSQ 7000 or a Fisons Intruments Trio 1000 mass spectrometer. LRMS means low resolution mass spectrum and the calculated and observed ions quoted refer to the isotopic composition of lowest mass.

EXAMPLE 1

N-Hydroxy-2-[4-(4-phenylphenyl)-1,2,3,6-tetrahydropyridin-1-ylsulphonyl]acetamide Potassium carbonate (207 mg, 1.5 mmol) was added to a stirred mixture of the title compound of Preparation 8 (186 mg, 0.5 mmol), hydroxylamine hydrochloride (104 mg, 1.5 mmol), tetrahydrofuran (2 ml) and methanol (3 ml). The reaction mixture was heated under reflux for 20 hours, allowed to cool, diluted with water (15 ml) and ethyl acetate (10 ml) and acidified with concentrated hydrochloric acid. This mixture was then briefly heated at 100° C., allowed to cool and filtered. The material thus obtained was washed sequentially with water and ethyl acetate, then dried under vacuum to provide the title compound (125 mg, 67%) as a colourless solid, m.p. 216–218° C. Found: C, 61.05; H, 5.35; N, 7.41. $C_{19}H_{20}N_2O_4S$ requires C, 61.27; H, 5.41; N, 7.52%. δ(DMSO$_{d6}$): 2.62 (m,2H), 3.50 (m,2H), 3.92 (s,2H), 3.98 (m,2H), 6.24 (brs, 1H), 7.35 (m,1H), 7.41–7.48 (m,2H), 7.52–7.58 (m,2H), 7.62–7.73 (m,4H), 9.22 (s,1H), 10.82 (s, 1H).

LRMS (APCI): 373 (M+H)$^+$.

EXAMPLE 2

N-Hydroxy-2-[4-(3-methyl-4-phenylphenyl)-1,2,3,6-tetrahydropyridin-1-ylsulphonyl]acetamide Obtained as a colourless solid (58%), m.p. 190–191° C., from the title compound of Preparation 9, using the procedure of EXAMPLE 1. Found: C, 62.05; H, 5.74; N, 7.12. $C_{20}H_{22}N_2O_4S$ requires C, 62.16; H, 5.74; N, 7.25%. δ(DMSO$_{d6}$): 2.23 (s,3H), 2.60 (m,2H), 3.47 (t,2H), 3.90 (s,2H), 3.95 (m,2H), 6.20 (brs, 1H), 7.17 (d,1H), 7.30–7.48 (m,7H), 9.20 (s,1H), 10.80 (s,1H).

LRMS (Thermospray): 388(M+H)$^+$.

EXAMPLE 3

N-Hydroxy-2-[4-(4-phenylphenyl)piperidin-1-ylsulphonyl]acetamide

Obtained as a colourless solid (62%), m.p. 200–201° C., from the title compound of Preparation 10, using the procedure of EXAMPLE 1. Found: C, 60.96; H, 5.86; N, 6.97. $C_{19}H22N_2O_4S$ requires C, 60.94; H, 5.92; N, 7.48%. δ(DMSOd6): 1.63 (m,2H), 1.83 (m,2H), 2.66 (m,1H), 2.98 (t,2H), 3.70 (m,2H), 3.83 (s,2H), 7.30 (m,3H), 7.40 (t,2H), 7.54–7.60 (m,4H), 9.18 (s,1H), 10.75 (s,1H).

LRMS (Thermospray): 375 (M+H)$^+$.

EXAMPLE 4

N-Hydroxy-2-(4-phenyl-1,2,3,6-tetrahydropyridin-1-ylsulphonyl)acetamide

Obtained as a colourless solid (76%), m.p. 175–176° C., from the title compound of Preparation 11, using the procedure of EXAMPLE 1. Found: C, 52.41; H, 5.39; N, 9.35. $C_{13}H_{16}N_2O_4S$ requires C, 52.69; H, 5.44; N, 9.45%. δ(DMSO$_{d6}$): 2.58 (m,2H), 3.46 (t,2H), 3.90 (s,2H), 3.95 (m,2H), 6.18 (brs, 1H), 7.23–7.48 (m,5H), 9.20 (s,1H), 10.80 (s,1H).

EXAMPLE 5

N-Hydroxy-2-(4-phenylpiperidin-1-ylsulphonyl)acetamide

Obtained as a colourless solid (44%), m.p. 185–187° C., from the title compound of Preparation 12, using the procedure of EXAMPLE 1. Found: C, 52.08; H, 6.04; N, 9.23. $C_{13}H_{18}N_2O_4S$ requires C, 52.33; H, 6.08; N, 9.39%. δ(DMSO$_{d6}$): 1.62 (m,2H), 1.82 (m,2H), 2.62 (m,1H), 2.98 (t,2H), 3.70 (m,2H), 3.84 (s,2H), 7.15–7.33 (m,5H), 9.20 (s,1H), 10.78 (s,1H).

EXAMPLE 6

N-Hydroxy-2-(4-benzylpiperidin-1-ylsulphonyl)acetamide

Obtained as a colourless solid (35%), m.p. 132–135° C., from the title compound of Preparation 13, using the procedure of EXAMPLE 1. Found: C, 53.66; H, 6.43; N, 8.82. $C_{14}H_{20}N_2O_4S$ requires C, 53.83; H, 6.45; N, 8.97%. δ(DMSO$_{d6}$): 1.13 (m,2H), 1.58 (m,3H), 2.49 (d,2H), 2.75 (t,2H), 3.50 (d,2H), 3.73 (s,2H), 7.10 (m,3H), 7.22 (m,2H), 9.10 (s,1H), 10.70 (s,1H).

EXAMPLE 7

N-Hydroxy-2(R,S)-[4-(4-phenylphenyl)-1,2,3,6-tetrahydropyridin-1-ylsulphonyl]pent-4-enamide O-(7-Azabenzotriazol-1-yl)-1,1,3,3-tetramethyluronium hexafluorophosphate (100 mg, 0.26 mmol) was added to a stirred solution of the title compound of Preparation 15 (70 mg, 0.18 mmol) and N-ethyidiisopropylamine (0.03 ml, 0.18 mmol) in anhydrous dimethylformamide (1 ml), under nitrogen, at room temperature. After 15 minutes, a solution of hydroxylamine hydrochloride (37 mg, 0.53 mmol) and N-ethyidiisopropylamine (0.12 ml, 0.7 mmol) in anhydrous dimethylformamide (0.5 ml) was added and the reaction mixture stirred for 20 hours, then partitioned between ethyl acetate and aqueous phosphate buffer (pH 7). The organic phase was separated, washed with water, dried (MgSO$_4$) and evaporated under reduced pressure, then the residue purified by flash chromatography, using dichloromethane:methanol (97:3) as eluant, to give the title compound (55 mg). as a colourless, amorphous solid. δ(DMSO$_{d6}$): 2.50–2.80 (m,4H), 3.50 (m,2H), 3.80 (dd,1H), 4.00 (m,2H), 5.03–5.18 (m,2H), 5.62 (m,1H), 6.23 (brs, 1H), 7.37 (m,1H), 7.45 (m,2H), 7.53 (m,2H), 7.67 (m,4H), 9.22 (s,1H), 10.85 (s,1H).

LRMS (Thermospray): 413 (M+H)$^+$.

EXAMPLE 8

N-Hydroxy-2(R,S)-[4-(3-methyl-4-phenylphenyl)-1,2,3,6-tetrahydropyridin-1-ylsulphonyl]pent-4-enamide Obtained as a solid (13%) from the title compound of Preparation 17, using the procedure of EXAMPLE 7, but with an elution gradient of dichloromethane:methanol (100:0 to 90:10) for the chromatographic purification step. δ(CDCl$_3$): 2.25 (s,3H), 2.62 (m,2H), 2.82 (m,2H), 3.62 (m,2H), 3.80 (dd,1H), 4.10 (m,2H), 5.10–5.22 (m,2H), 5.75 (m,1H), 6.03 (brs, 1H), 7.20–7.43 (m,8H).

LRMS (APCI): 427 (M+H)$^+$.

EXAMPLE 9

N-Hydroxy-5-phenyl-2(R,S)-[4-(4-phenylphenyl)-1,2,3,6-tetrahydropyridin-1-ylsulphonyl]pentanamide Obtained as a colourless solid (35%), m.p. 150° C. (decomp.), from the title compound of Preparation 18, using the procedure of EXAMPLE 1. δ(DMSO$_{d6}$): 1.50 (m,2H), 1.80 (m,1H), 2.00 (m,1H), 2.54 (m,4H), 3.45 (m,2H), 3.75 (dd,1H), 3.98 (m,2H), 6.10 (brs,1H), 7.10–7.54 (m,10H), 7.63 (m,4H), 9.10 (s,1H), 10.88 (s,1H).

LRMS (Thermospray): 492 (M+H)$^+$.

EXAMPLE 10

N-Hydroxy-2-methyl-2-[4-(4-phenylphenyl)-1,2,3,6-tetrahydropyridin-1-ylsulphonyl]propanamide Obtained as an amorphous solid (41%) from the title compound of Preparation 19, using the procedure of EXAMPLE 7. δ(DMSO$_{d6}$): 1.50 (s,6H), 2.66 (m,2H), 3.50 (m,2H), 4.00 (m,2H), 6.10 (brs,1H), 7.30–7.70 (m,9H), 9.00 (s,1H), 10.78 (s,1H).

EXAMPLE 11

N-Hydroxy-1-[4-(3-methyl-4-phenylphenyl)-1,2,3,6-tetrahydropyridin-1-ylsulphonyl]cyclopentanecarboxamide Obtained as a solid (44%) from the title compound of Preparation 21, using the procedure of EXAMPLE 7, but with dichloromethane:methanol (99:1) as eluant for the chromatographic purification step. δ(CDCl$_3$): 1.70 (m,2H), 1.86 (m,2H), 2.27 (s,3H), 2.37 (m,2H), 2.48 (m,2H), 2.62 (m,2H), 3.60 (t,2H), 4.05 m,2H), 6.02 (brs,1H), 7.20–7.43 (m,8H).

EXAMPLE 12

N-Hydroxy-2-ethyl-2-[4-(4-phenylphenyl)-1,2,3,6-tetrahydropyridin-1-sulphonyl]butanamide Obtained as a solid (56%) from the title compound of Preparation 23, using the procedure of EXAMPLE 7.

δ(DMSO$_{d6}$): 0.90 (m,6H), 1.95–2.13 (m,4H), 2.52 (m,2H), 3.48 (m,2H), 3.98 (m,2H), 6.10 (brs,1H), 7.35 (m,1H), 7.44 (m,2H), 7.52 (m,2H), 7.64 (m,4H), 9.03 (brs,1H), 10.70 (brs,1H).

EXAMPLE 13

N-Hydroxy-2(R,S)-[4-(4-phenylphenyl)-1,2,3,6-tetrahydropyridin-1-ylsulphonyl]hexanamide Obtained as a colourless solid (72%), m.p. 186–189° C., from the title compound of Preparation 25, using the procedure of EXAMPLE 7, but with 1-methylpyrrolidin-2-one as reaction solvent and with crystallisation from diisopropyl ether:ethyl acetate, rather than flash chromatography, as the purification technique. Found: C, 63.03; H, 6.60; N, 6.43. $C_{23}H_{28}N_2O_4S$; 0.50 $H_2O$ requires C, 63.13; H, 6.68; N, 6.40%. δ(DMSO$_{d6}$): 0.83 (t,3H), 1.10–1.35 (m,4H), 1.78 (m,1H), 1.98 (m,1H), 2.55 (m,2H), 3.50 (m,2H), 3.70 (dd, 1H), 3.98 (m,2H), 6.12 (brs, 1H), 7.32 (m,1H), 7.44 (m,2H), 7.52 (m,2H), 7.64 (m,4H), 9.20 (brs, 1H), 10.85 (brs,1H).

LRMS (APCI): 429 (M+H)$^+$.

EXAMPLE 14

N-Hydroxy-4-methyl-2(R,S)-[4-(4-phenylphenyl)-1,2,3,6-tetrahydropyridin-1-ylsulphonyl]pent-4-enamide Obtained as a colourless solid (33%), m.p. 170–171° C., from the title compound of Preparation 27, using the procedure of EXAMPLE 7, but with an elution gradient of dichloromethane:methanol (100:0 to 98:2) for the chromatographic purification step. δ(DMSO$_{d6}$): 1.65 (s,3H), 2.40–2.80 (m,4H), 3.52 (m,2H), 3.90 (dd,1H), 4.00 (m,2H), 4.70 (s,1H), 4.78 (s,1H), 6.23 (brs, 1H), 7.35 (m,1H), 7.44 (m,2H), 7.52 (d,2H), 7.65 (m,4H), 9.22 (s,1H), 10.85 (s,1H).

LRMS (APCI): 427 (M+H)$^+$.

EXAMPLE 15

N-Hydroxy-2(R,S)-methyl-2-[4-(3-methyl-4-phenylphenyl)-1,2,3,6-tetrahydropyridin-1-ylsulphonyl]pent-4-enamide Obtained as a colourless gum (20%) from the title compound of Preparation 29, using the procedure of EXAMPLE 7, but with an elution gradient of dichloromethane:methanol (100:0 to 98:2 to 95:5) for the chromatographic purification step. δ(CDCl$_3$): 1.60 (s,3H), 2.28 (s,3H), 2.64 (m,3H), 3.00 (m,1H), 3.62 (m,2H), 4.10 (m,2H), 5.21 (m,2H), 5.70 (m,1H), 6.03 (brs,1H), 7.20–7.44 (m,8H).

LRMS (APCI): 441 (M+H)$^+$.

EXAMPLE 16

N-Hydroxy-2-[3-(4-phenylphenoxy)azetidin-1-ylsulphonyl]acetamide

Obtained as a colourless solid (66%) from the title compound of Preparation 32, using the procedure of EXAMPLE 1. δ(DMSO$_{d6}$): 4.03 (s,2H), 4.05 (dd,2H), 5.09 (m,1H), 6.94 (d,2H), 7.30 (m,1H), 7.40 (m,2H), 7.60 (m,4H), 9.25 (s,1H), 10.80 (brs,1H).

LRMS (Thermospray): 364 (M+H)$^+$.

EXAMPLE 17

N-Hydroxy-2-{4-[4-(3-ethoxyphenyl)-3-methylphenyl]-1,2,3,6-tetrahydropyridin-1-ylsulphonyl}acetamide Potassium carbonate (406 mg, 3 mmol) was added to a stirred mixture of the title compound of Preparation 41 (429 mg, 1 mmol), hydroxylamine hydrochloride (212 mg, 3 mmol) and methanol (20 ml). The reaction mixture was heated under reflux for about 6 hours, allowed to cool and partitioned between ethyl acetate and 1M hydrochloric acid. The separated organic phase was dried (MgSO$_4$) and evaporated under reduced pressure, then the residue triturated with diisopropyl ether and crystallised from ethyl acetate to yield the title compound (148 mg, 34%) as a colourless solid, m.p. 151–153° C. Found: C, 61.01; H, 6.04; N, 6.48. $C_{22}H_{26}N_2O_5S$ requires C, 61.38; H, 6.09; N, 6.51%. δ(DMSO$_{d6}$): 1.33 (t,3H), 2.23 (s,3H), 2.60 (m,2H), 3.46 (t,2H), 3.91 (s,2H), 3.96 (m,2H), 4.03 (q,2H), 6.10 (brs,1H), 6.80–6.95 (m,3H), 7.17 (d,1H), 7.28–7.38 (m,3H), 9.20 (brs,1H), 10.8 (brs,1H).

LRMS (APCI): 431 (M+H)$^+$.

EXAMPLE 18

N-Hydroxy-2-[4-(3-methoxy-4-phenylphenyl)-1,2,3,6-tetrahydropyridin-1-ylsulphonyl]acetamide Potassium carbonate (95 mg, 0.7 mmol) was added to a stirred mixture of the title compound of Preparation 45 (170 mg, 0.4 mmol), hydroxylamine hydrochloride (49 mg, 0.7 mmol) and methanol (3 ml). The reaction mixture was heated under reflux for about 2 hours, allowed to cool, diluted with phosphate buffer (15 ml) and extracted with ethyl acetate (2×15 ml). The combined organic phases were dried (MgSO$_4$) and evaporated under reduced pressure, then the residue was triturated with ethyl acetate to furnish the title compound (50 mg, 30%) as a colourless solid, m.p. 175–177° C. Found: C, 58.84; H, 5.51; N, 6.70. $C_{20}H_{20}N_2O_5S$; 0.10 $CH_2Cl_2$ requires C, 58.75; H, 5.45; N, 6.82%. δDMSO$_{d6}$): 2.63 (m,2H), 3.50 (t,2H), 3.80 (s,3H), 3.93 (s,2H), 3.99 (s,2H), 6.27 (s,1H), 7.10 (d,1H), 7.16 (s,1H), 7.27 (d,1H), 7.31 (d,1H), 7.41 (t,2H), 7.47 (d,2H), 9.23 (brs,1H), 10.80 (brs,1H).

LRMS (Thermospray): 420 (M+NH$_4$)$^+$.

EXAMPLE 19

N-Hydroxy-2-[4-(3-methoxy-4-phenylphenyl)-1,2,3,6-tetrahydropyridin-1-ylsulphonyl]-2-methylpropanamide O-(7-Azabenzotriazol-1-yl)-1,1,3,3-tetramethyluronium hexafluorophosphate (274 mg, 0.72 mmol) was added to a stirred solution of the title compound of Preparation 50 (200 mg, 0.48 mmol) and N-ethyldiisopropylamine (0.08 ml, 0.48 mmol) in anhydrous dimethylformamide (4 ml), under nitrogen, at room temperature. After 15 minutes, hydroxylamine hydrochloride (100 mg, 1.44 mmol) and N-ethyidiisopropylamine (0.33 ml, 1.9 mmol) were added and the reaction mixture stirred for about 3 hours, then partitioned between ethyl acetate and aqueous phosphate buffer (pH 7). The organic phase was separated, washed with water, dried (MgSO$_4$) and evaporated under reduced pressure, then the residue was triturated with diisopropyl ether to give the title compound (71 mg, 36%) as a colourless, amorphous solid, m.p. 156–158° C. Found: C, 60.80; H, 6.17; N, 6.25. $C_{22}H_{26}N_2O_5S$; 0.10 $H_2O$ requires C, 61.12; H, 6.11; N, 6.48%. δ(DMSO$_{d6}$): 1.51 (s,6H), 2.57 (m,2H), 3.43 (t,2H), 3.80 (s,3H), 4.03 (m,2H), 6.25 (brs,1H), 7.09 (d,1H), 7.13 (s,1H), 7.26 (d,1H), 7.31 (d,1H), 7.39 (t,2H), 7.46 (d,2H), 9.24 (brs,1H), 10.79 (brs,1H).

LRMS (APCI): 431 (M+H)$^+$.

EXAMPLE 20

N-Hydroxy-2-[4-(3-fluoro-4-phenylphenyl)-1,2,3,6-tetrahydropyridin-1-ylsulphonyl]acetamide Obtained as a colourless solid (40%), m.p. 184–188° C., from the title compound of Preparation 47, using the procedure of Example 1. Found: C, 58.39; H, 4.90; N, 6.84. $C_{19}H_{19}FN_2O_4S$ requires C, 58.45; H, 4.91; N, 7.17%. $\delta(DMSO_{d6})$: 2.61 (m,2H), 3.47 (t,2H), 3.94 (s,2H), 4.00 (s,2H), 6.35 (brs,1H), 7.33–7.60 (m,8H), 9.23 (brs,1H), 10.80 (brs,1H).

LRMS (Thermospray): 408 $(M+NH_4)^+$.

EXAMPLE 21

N-Hydroxy-2-{4-[4-(3-ethoxyphenyl)phenyl]-1,2,3,6-tetrahydropyridin-1-ylsulphonyl}acetamide Obtained as a colourless solid (76%), m.p. 168–170° C., from the title compound of Preparation 56, using the procedure of Example 1. $\delta(DMSO_{d6})$: 1.34 (t,3H), 2.61 (m,2H), 3.49 (t,2H), 3.94 (s,2H), 3.98 (s,2H), 4.10 (q,2H), 6.25 (brs,1H), 6.91 (d,1H), 7.17 (s,1H), 7.22 (d,1H), 7.33 (t,1H), 7.52 (d,2H), 7.66 (d,2H), 9.22 (brs,1H), 10.80 (brs,1H).

LRMS (Thermospray): 434 $(M+NH_4)^+$.

EXAMPLE 22

N-Hydroxy-2-{4-[4-(3-methoxyphenyl)-3-methylphenyl]-1,2,3,6-tetrahydropyridin-1-ylsulphonyl}acetamide Obtained as a colourless solid (76%), m.p. 162–165° C., from the title compound of Preparation 61, using the procedure of Example 1. Found: C, 60.26; H, 5.86; N, 6.43. $C_{21}H_{24}N_2O_5S$ requires C, 60.56; H, 5.81; N, 6.73%. $\delta(DMSO_{d6})$: 2.23 (s,3H), 2.60 (m,2H), 3.47 (t,2H), 3.77 (s,3H), 3.93 (s,2H), 3.97 (s,2H), 6.20 (brs,1H), 6.83–6.94 (m,3H), 7.18 (d,1H), 7.27–7.39 (m, 3H), 9.22 (brs,1H), 10.80 (brs,1H).

LRMS (APCI): 416 $(M)^+$.

EXAMPLE 23

N-Hydroxy-2-{4-[4-(3-ethylphenyl)-3-methylphenyl]-1,2,3,6-tetrahydropyridin-1-ylsulphonyl}acetamide Obtained as a colourless solid (58%), m.p. 151–154° C., from the title compound of Preparation 63, using the procedure of Example 1. Found: C, 62.75; H, 6.24; N, 6.26. $C_{22}H_{26}N_2O_4S$; 0.50 $H_2O$ requires C, 62.39; H, 6.43; N, 6.61%. $\delta(DMSO_{d6})$: 1.20 (t,3H), 2.24 (s,3H), 2.61 (m,4H), 3.47 (t,2H), 3.92 (s,2H), 3.97 (s,2H), 6.20 (brs,1H), 7.10–7.23 (m,4H), 7.27–7.38 (m,3H), 9.22 (brs,1H), 10.81 (brs,1H).

LRMS (APCI): 414 $(M)^+$.

EXAMPLE 24

N-Hydroxy-4-{4-[4-(3-Methoxyphenyl)-3-methylphenyl]-1,2,3,6-tetrahydropyridin-1-ylsulphonyl}tetrahydropyran-4-carboxymide Obtained as a pale yellow solid (47%), m.p. 160–170° C., from the title compound of Preparation 65, using the procedure of Example 19. $\delta(DMSO_{d6})$: 1.93 (m,2H), 2.23 (s,3H), 2.39 (m,2H), 2.43 (m,2H), 3.20 (t,2H), 3.49 (m,2H), 3.77 (s,3H), 3.86 (m,2H), 4.00 (m,2H), 6.16 (brs,1H), 6.83–6.94 (m,3H), 7.17 (d,1H), 7.36 (m,3H), 9.21 (brs,1H), 11.00 (brs,1H).

LRMS (APCI) 487 $(M+H)^+$.

EXAMPLE 25

N-Hydroxy-4-{4-[4-(3-methoxyphenyl)-3-methylphenyl]piperidin-1-ylsulphonyl}tetrahydropyran-4-carboxymide Obtained as a white solid (82%), m.p. 200–202° C., from the title compound of Preparation 67, using the procedure of Example 19, except that the residue was crystallised from methanol. Found: C, 60.02; H, 6.78; N, 5.45. $C_{25}H_{32}N_2O_6S$; $CH_3OH$ requires C, 59.98; H, 6.97; N, 5.38%. $\delta(DMSO_{d6})$: 1.60 (m,2H), 1.78 (m,2H), 1.90 (m,2H), 2.20 (s,3H), 2.38 (m,2H), 2.64 (m,1H), 3.04 (t,2H), 3.20 (t,2H), 3.70 (m,2H), 3.77 (s,3H), 3.86 (m,2H), 6.87 (m,3H), 7.13 (m,3H), 7.33 (t,1H), 9.16 (brs,1H), 10.97 (brs,1H).

LRMS (APCI) 489 $(M+H)^+$.

EXAMPLE 26

N-Hydroxy-2-{4-[3-methoxy-4-(3-methoxyphenyl)phenyl]piperidin-1-ylsulphonyl}-2-methylpropanamide Obtained as a white solid (47%), m.p. 161–163° C., from the title compound of Preparation 74, using the procedure of Example 19, except that the residue was purified by flash chromatography using dichloromethane:methanol:concentrated aqueous ammonia solution (90:10:1) as eluant. Found: C, 59.39; H, 6.58; N, 6.13. $C_{23}H_{30}N_2O_6S$ requires C, 59.72; H, 6.54; N, 6.06%. $\delta(DMSO_{d6})$: 1.49 (s,6H), 1.64 (m,2H), 1.81 (m,2H), 2.70 (m,1H), 3.06 (t,2H), 3.75 (s,8H), 6.87 (m,2H), 6.98 (m,3H), 7.20 (d,1H), 7.27 (t,1H), 8.99 (brs,1H), 10.75 (brs,1H).

LRMS (Thermospray): 480 $(M+NH_4)^+$.

EXAMPLE 27

N-Hydroxy-2-{4-[4(3-ethoxyphenyl)-3-methoxyphenyl]piperidin-1-ylsulphonyl}-2-methylpropanamide Obtained as a white solid (39%), m.p. 134–136° C., from the title compound of Preparation 77, using the procedure of Example 26. Found: C, 60.60; H, 6.80; N, 5.82. $C_{24}H_{32}N_2O_6S$ requires C, 60.48; H, 6.77; N, 5.88%. $\delta(DMSO_{d6})$: 1.32 (t,3H), 1.49 (s,6H), 1.66 (m,2H), 1.81 (m,2H), 2.70 (m,1H), 3.07 (t,2H), 3.76 (s,5H), 4.02 (q,2H), 6.85 (m,2H), 6.98 (m,3H), 7.20 (d,1H), 7.27 (t,1H), 9.00 (brs,1H), 10.76 (brs,1H).

LRMS (Thermospray): 494 $(M+NH_4)^+$.

EXAMPLE 28

N-Hydroxy-4-{4-[4-(3-ethoxyphenyl)-3-methylphenyl]-1,2,3,6-tetrahydropyridin-1-ylsulphonyl}tetrahydropyran-4-carboxymide Obtained as a colourless solid (87%), m.p. 152–154° C., from the title compound of Preparation 79, using the procedure of Example 19. Found: C, 61.99; H, 6.47; N, 5.54. $C_{26}H_{32}N_2O_6S$ requires C, 62.38; H, 6.44; N, 5.60%. $\delta(DMSO_{d6})$: 1.33 (t,3H), 1.93 (m,2H), 2.24 (s,3H), 2.40 (d,2H), 2.52 (m,2H), 3.21 (dd,2H), 3.50 (m,2H), 3.88 (m,2H), 3.98–4.10 (m,4H), 6.18 (brs,1H), 6.80–6.95 (m,3H), 7.18 (d,1H), 7.26–7.37 (m,3H), 9.22 (brs,1H), 11.05 (brs,1H).

LRMS (APCI): 501 $(M+H)^+$.

EXAMPLE 29

N-Hydroxy-4-{4-[4-(3-ethoxyphenyl)-3-methylphenyl]piperidin-1-ylsulphonyl}tetrahydropyran-4-carboxymide Palladium on barium sulfate (5%, 5 mg) was added to a stirred solution of the title compound of Example 28 (50 mg, 0.1 mmol) in a mixture of 1,2-dimethoxyethane (1 ml) and methanol (3 ml), then the reaction mixture hydrogenated at 345 kPa (50 psi) pressure for about 20 hours. A further portion of palladium on barium sulfate (5%, 5 mg) was added and hydrogenation continued for an additional 20 hours. The catalyst was removed by filtration, the solvent evaporated under reduced pressure and the residue crystallised from ether-hexane to afford the title compound (34 mg, 66%) as a colourless solid, m.p. 165–167° C. Found: C, 60.81; H, 6.76; N, 5.35. $C_{26}H_{34}N_2O_6S$; 0.50 $H_2O$ requires C, 61.03; H, 6.89; N, 5.47%. $\delta DMSO_{d6}$): 1.35 (t,3H), 1.60 (m,2H), 1.78 (m,2H), 1.92 (m,2H), 2.20 (s,3H), 2.40 (d,2H), 2.62 (m,1H), 3.03 (dd,2H), 3.20 (dd,2H), 3.73 (m,2H), 3.86 (m,2H), 4.04 (q,2H), 6.80–6.92 (m,3H), 7.07–7.17 (m,3H), 7.30 (t,1H), 9.18 (brs,1H), 11.0 (brs,1H).

LRMS (Thermospray): 520 $(M+NH_4)^+$.

EXAMPLE 30

N-Hydroxy-2-{4-[4-(3-ethoxyphenyl)-3-methylphenyl]-1,2,3,6-tetrahydropyridin-1-ylsulphonyl}2-methylpropanamide Obtained as a colourless solid (33%), m.p. 116–118° C., from the title compound of Preparation 81, using the procedure of Example 19. Found: C, 62.52; H, 6.47; N, 6.00. $C_{24}H_{30}N_2O_5S$ requires C, 62.86; H, 6.59; N, 6.11%. $\delta(DMSO_{d6})$: 1.34 (t,3H), 1.52 (s,6H), 2.23 (s,3H), 2.53 (m,2H), 3.50 (m,2H), 4.00–4.10 (m,4H), 6.18 (brs,1H), 6.80–6.95 (m,3H), 7.18 (d,1H), 7.28–7.38 (m,3H), 9.03 (brs, 1H), 10.8 (brs,1H).

LRMS (Thermospray): 459 $(M+H)^+$.

EXAMPLE 31

N-Hydroxy-2-{4-[4-(3-ethoxyphenyl)-3-methylphenyl]piperidin-1-ylsulphonyl}acetamide Obtained as a colourless solid (48%), m.p. 179–180° C. (crystallised from diisopropyl ether), from the title compound of Preparation 82, using the procedure of Example 17. Found: C, 60.72; H, 6.49; N, 6.36. $C_{22}H_{28}N_2O_5S$ requires C, 61.09; H, 6.53; N, 6.48%. $\delta(DMSO_{d6})$: 1.31 (t,3H), 1.68 (m,2H), 1.86 (m,2H), 2.20 (s,3H), 2.65 (m,1H), 3.00 (m,2H), 3.72 (m,2H), 3.86 (s,2H), 4.03 (q,2H), 6.80–6.90 (m,3H), 7.10 (s,2H), 7.17 (s,1H), 7.30 (t,1H), 9.20 (brs,1H), 10.8 (brs,1H).

LRMS (APCI): 433 $(M+H)^+$.

EXAMPLE 32

N-Hydroxy-2-{4-[4-(3-ethoxyphenyl)-3-methylphenyl]piperidin-1-ylsulphonyl}-2-methylpropanamide Obtained as a colourless solid (53%), m.p. 172–174° C. (crystallised from diisopropyl ether), from the title compound of Preparation 84, using the procedure of Example 19. Found: C, 62.20; H, 6.99; N, 6.02. $C_{24}H_{32}N_2O_5S$ requires C, 62.58; H, 7.00; N, 6.08%. $\delta(DMSO_{d6})$: 1.31 (t,3H), 1.50 (s,6H), 1.61 (m,2H), 1.79 (m,2H), 2.20 (s,3H), 2.65 (m,1H), 3.05 (m,2H), 3.75 (m,2H), 4.03 (q,2H), 6.80–6.90 (m,3H), 7.08–7.18 (m,3H), 7.30 (dd,1H), 8.98 (brs,1H), 10.75 (brs,1H).

LRMS (APCI): 461 $(M+H)^+$.

EXAMPLE 33

N-Hydroxy-2-{4-[3-methyl-4-(pyridin-2-yl)phenyl]-1,2,3,6-tetrahydropyridin-1-ylsulphonyl}acetamide Obtained as a colourless amorphous solid (50%) from the title compound of Preparation 85, using the procedure of Example 17. $\delta(DMSO_{d6})$: 2.33 (s,3H), 2.60 (m,2H), 3.46 (t,2H), 3.91 (s,2H), 3.97 (m,2H), 6.12 (brs,1H), 7.30–7.40 (m,4H), 7.50 (d,1H), 7.84 (dd,1H), 8.63 (d,1H), 9.20 (brs, 1H), 10.8 (brs,1H).

LRMS (APCI): 388 $(M+H)^+$.

EXAMPLE 34

N-Hydroxy-2-{4-[3-methyl-4-(pyridin-3-yl)phenyl]-1,2,3,6-tetrahydropyridin-1-ylsulphonyl}acetamide Obtained as a colourless solid (57%), m.p. 132–136° C., from the title compound of Preparation 86, using the procedure of Example 31. $\delta(DMSO_{d6})$: 2.23 (s,3H), 2.60 (m,2H), 3.46 (t,2H), 3.91 (s,2H), 3.97 (m,2H), 6.12 (brs,1H), 7.21 (d,1H), 7.35 (d,1H), 7.40 (s,1H), 7.45 (dd,1H), 7.78 (d,1H), 8.55 (m,2H), 9.20 (brs,1H), 10.8 (brs,1H).

LRMS (APCI): 388 $(M+H)^+$.

EXAMPLE 35

N-Hydroxy-2-{4-[3-methyl-4-(pyridin-4yl)phenyl]-1,2,3,6-tetrahydropyridin-1-ylsulphonyl}acetamide Obtained as a colourless solid (20%), m.p. 165–1670 C, from the title compound of Preparation 87, using the procedure of Example 31. $\delta(DMSO_{d6})$: 2.26 (s,3H), 2.60 (m,2H), 3.47 (t,2H), 3.92 (s,2H), 3.97 (m,2H), 6.12 (brs,1H), 7.22 (d,1H), 7.35–7.42 (m,4H), 8.62 (d,2H), 9.20 (brs,1H), 10.8 (brs,1H).

LRMS (APCI): 388 $(M+H)^+$.

EXAMPLE 36

N-Hydroxy -2-{4-[4-(6-ethoxypydridin-2-yl)-3-methylphenyl]piperidin-1-ylsulphonyl}-2-methylpropanamide Obtained as a colourless solid (30%), m.p. 184–187° C., from the title compound of Preparation 91, using the procedure of Example 19, except that the residue was purified by flash chromatography using dichloromethane: ethanol (98:2) as eluant. $\delta(DMSO_{d6})$: 1.30 (t,3H), 1.48 (s,6H), 1.63 (m,2H), 1.79 (m,2H), 2.35 (s,3H), 2.67 (m,1H), 3.05 (t,2H), 3.75 (d,2H), 4.30 (q,2H), 6.72 (d,1H), 7.05 (d,1H), 7.15 (m,2H), 7.34 (d,1H), 7.73 (t,1H), 9.00 (brs,1H), 10.75 (brs, 1H).

HRMS (positive ion electrospray): 462.206 $(M+H)^+$.

EXAMPLE 37

N-Hydroxy-4-[4-(4-phenylphenyl)-1,2,3,6-tetrahydropyridin-1-ylsulphonyl]tetrahydropyran-4-carboxymide Obtained as a colourless solid (68%), m.p. 191–193° C., from the title compound of Preparation 93, using the procedure of Example 19, but with crystallisation of the residue from methanol. $\delta(DMSO_{d6})$: 1.93 (m,2H), 2.40 (d,2H), 2.55 (m,2H), 3.20 (t,2H), 3.48 (m,2H), 3.85 (m,2H), 4.00 (m,2H), 6.11 (brs,1H), 7.35 (t,1H), 7.44 (m,2H), 7.52 (d,2H), 7.65 (m,4H), 9.22 (brs,1H), 11.05 (brs,1H).

LRMS (APCI): 443 $(M+H)^+$.

EXAMPLE 38

N-Hydroxy-4-{4-[4-(4-ethoxyphenyl)-3-methylphenyl]-1,2,3,6-tetrahydropyridin-1-ylsulphonyl}tetrahydropyran-4-carboxymide Obtained as a colourless solid (36%), m.p. 159–161° C., from the title compound of Preparation 95, using the procedure of Example 19, but with crystallisation of the residue from dichloromethane-diisopropyl ether. δ(DMSO$_{d6}$): 1.35 (t,3H), 1.94 (m,2H), 2.22 (s,3H), 2.38 (d,2H), 2.50 (brs,2H), 3.20 (t,2H), 3.50 (brs,2H), 3.87 (dd,2H), 3.98 (brs,2H), 4.04 (q,2H), 6.15 (brs,1H), 6.96 (d,2H), 7.13 (d,1H), 7.22 (d,2H), 7.28 (d,1H), 7.33 (s,1H), 9.20 (brs,1H),11.05 (brs,1H).

LRMS (Thermospray): 515 (M+NH$_4$)$^+$.

EXAMPLE 39

N-Hydroxy-2-{4-[4-(3-hydroxymethylphenyl)-3-methylphenyl]-1,2,3,6-tetrahydropyridin-1-ylsulphonyl}acetamide Obtained as a colourless solid (63%), m.p. 174–176° C. (crystallised from methanol-diisopropyl ether), from the title compound of Preparation 97, using the procedure of Example 17. Found: C, 60.35; H, 5.75; N, 6.70. C$_{21}$H$_{24}$N$_2$O$_5$S requires C, 60.56; H, 5.81; N, 6.73%. δ(DMSO$_{d6}$): 2.22 (s,3H), 2.60 (m,2H), 3.47 (t,2H), 3.93 (s,2H), 3.97 (s,2H), 4.53 (d,2H), 5.19 (t,1H exchangeable), 6.20 (brs,1H), 7.15–7.42 (m,7H), 9.20 (brs,1H), 10.80 (brs,1H).

LRMS (APCI): 417 (M+H)$^+$.

EXAMPLE 40

N-Hydroxy-2-methyl-2-{4-[3-methyl-4-(quinolin-3-yl)phenyl]-1,2,3,6-tetrahydropyridin-1-ylsulphonyl}propanamide Obtained as a colourless solid (51%), m.p. 158–160° C., from the title compound of Preparation 100, using the procedure of Example 19. δ(DMSO$_{d6}$): 1.50 (s,6H), 2.32 (s,3H), 2.57 (m,2H), 3.53 (m,2H), 4.03 (m,2H), 6.23 (brs, 1H), 7.34–7.48 (m,3H), 7.63 (t,1H), 7.79 (t,1H), 8.04 (t,2H), 8.37 (s,1H), 8.91 (s,1H), 9.04 (brs,1H), 10.8 (brs,1H).

LRMS (APCI): 466 (M+H)$^+$.

EXAMPLE 41

N-Hydroxy-2-{4-[3-methyl-4-(3-methylthiophenyl)phenyl]-1,2,3,6-tetrahydropyridin-1-ylsulphonyl}acetamide Obtained as a colourless solid (17%), from the title compound of Preparation 102, using the procedure of Example 1. δ(DMSO$_{d6}$): 2.23 (s,3H), 2.49 (s,3H), 2.60 (m,2H), 3.47 (t,2H), 3.91 (s,2H), 3.97 (s,2H), 6.22 (brs,1H), 7.08 (d,1H), 7.17 (m,2H), 7.24 (d,1H), 7.34 (m, 3H), 9.22 (brs,1H), 10.80 (brs,1H).

LRMS (APCI): 432 (M)$^+$.

EXAMPLE 42

N-Hydroxy-2-{4-[4-(3-methoxymethylphenyl)-3-methylphenyl]-1,2,3,6-tetrahydropyridin-1-ylsulphonyl}acetamide Obtained as a colourless solid (28%), m.p. 151–153° C. (crystallised from ethyl acetate-diisopropyl ether), from the title compound of Preparation 104, using the procedure of Example 17. Found: C, 60.16; H, 6.00; N, 6.28. C$_{22}$H$_{26}$N$_2$O$_5$S; 0.10 H$_2$O requires C, 60.11; H,6.19; N, 6.37%. δ(DMSO$_{d6}$): 2.22 (s,3H), 2.60 (m,2H), 3.30 (s,3H), 3.47 (t,2H), 3.93 (s,2H), 3.97 (s.,2H), 4.04 (s,2H), 6.20 (brs,1H), 7.17 (d,1H), 7.21–7.42 (m,6H), 9.20 (brs,1H), 10.80 (brs,1H).

LRMS (Thermospray): 432 (M+H)$^+$.

EXAMPLE 43

N-Hydroxy-2-{4-[4-(3-[2-methoxyethoxy]phenyl)-3-methylphenyl]-1,2,3,6-tetrahydropyridin-1-ylsulphonyl}acetamide Obtained as a colourless solid (64%), m.p. 158–160° C. (crystallised from ethyl acetate), from the title compound of Preparation 107, using the procedure of Example 17. Found: C, 59.78; H, 6.10; N, 6.01. C$_{23}$H$_{28}$N$_2$O$_6$S requires C, 59.98; H, 6.13; N, 6.08%. δ(DMSO$_{d6}$); 2.24 (s,3H), 2.60 (m,2H), 3.30 (s,3H), 3.47 (t,2H), 3.66 (m,2H), 3.92 (s,2H), 3.97 (m,2H), 4.12 (t,2H), 6.20 (brs,1H), 6.89 (m,3H), 7.18 (d,1H), 7.34 (m,3H), 9.20 (brs,1H), 10.80 (brs,1H).

LRMS (Thermospray): 460 (M)$^+$.

EXAMPLE 44

N-Hydroxy-2-{4-[4-(2,3-dihydrobenzofuran-5-yl)-3-methylphenyl]-1,2,3,6-tetrahydropyridin-1-ylsulphonyl}acetamide Obtained as a colourless solid (56%), m.p. 158–162° C., from the title compound of Preparation 112, using the procedure of Example 17. Found: C, 57.01; H, 5.47; N, 5.26. C$_{22}$H$_{26}$N$_2$O$_5$S; 0.60 CH$_2$Cl$_2$ requires C, 56.61; H, 5.30; N, 5.84%. δ(DMSO$_{d6}$): 2.23 (s,3H), 2.58 (m,2H), 3.20 (t,2H), 3.44 (t,2H), 3.92 (s,2H), 3.96 (s,2H), 4.55 (t,2H), 6.20 (brs,1H), 6.78 (d,1H), 7.01 (d,1H), 7.12 (d,1H), 7.17 (s,1H), 7.27 (d,1H), 7.33 (s,1H), 9.20 (brs,1H), 10.80 (brs,1H).

LRMS (APCI): 428 (M+H)$^+$.

EXAMPLE 45

N-Hydroxy-2-{4[3-methyl-4-(3-trifluoromethylphenyl)phenyl]-1,2,3,6-tetrahydropyridin-1-ylsulphonyl}acetamide Obtained as a colourless solid (50%), m.p. 168–170° C. (crystallised from diisopropyl ether), from the title compound of Preparation 116, using the procedure of Example 17, except that tetrahydrofuran was used as a co-solvent for the reaction. Found: C, 54.96; H, 4.73; N, 5.97. C$_{21}$H$_{21}$F$_3$N$_2$O$_4$S; 0.25 H$_2$O requires C, 54.96; H, 4.72; N, 6.10%. δ(DMSO$_{d6}$): 2.24 (s,3H), 2.60 (m,2H), 3.47 (t,2H), 3.93 (s,2H), 3.97 (m,2H), 6.22 (brs,1H), 7.23 (d,1H), 7.36 (d,1H), 7.41 (s,1H), 7.68 (m,4H), 9.20 (brs,1H), 10.80 (brs,1H).

LRMS (APCI): 455 (M+H)$^+$.

EXAMPLE 46

N-Hydroxy-2-[4-(4-phenoxyphenyl)piperidin-1-ylsulphonyl]acetamide

Obtained as a colourless solid (13%), m.p. 176–179° C., from the title compound of Preparation 119, using the procedure of Example 17, except that dichloromethane was used as a co-solvent for the reaction. Found: C, 57.92; H, 5.62; N, 6.97. C$_{19}$H$_{22}$N$_2$O$_5$S; 0.20 H$_2$O requires C, 57.91; H, 5.73; N, 7.11%. δ(DMSO$_{d6}$): 1.63 (m,2H), 1.84 (m,2H), 2.63 (m,1H), 2.98 (t,2H), 3.69 (m,2H), 3.85 (s,2H), 6.96 (m,4H), 7.10 (t,1H), 7.27 (d,2H), 7.36 (t,2H), 9.20 (brs,1H), 10.80 (brs,1H).

LRMS (Thermospray): 392 (M+H)$^+$.

EXAMPLE 47

N-Hydroxy-2-{4-[4-(3-[2-methoxyethoxy]phenyl)-3-methylphenyl]piperidin-1-ylsulphonyl}-2-methylpropanamide Obtained as a colourless solid (42%), m.p. 155–156° C., from the title compound of Preparation 122, using the procedure of Example 19, except that the residue was purified by flash chromatography, using dichloromethane:methanol (97:3) as eluant, prior to crystallisation from dichloromethane-diisopropyl ether. δ(DMSO$_{d6}$): 1.50 (s,6H), 1.60 (m,2H), 1.80 (m,2H), 2.20 (s,3H), 2.65 (m,1H), 3.05 (t,2H), 3.30 (s,3H), 3.62 (t,2H), 3.74 (d,2H), 4.10 (t,2H), 6.80–6.92 (m,3H), 7.10–7.17 (m,3H), 7.30 (t,1H), 9.02 (brs,1H), 10.7 (brs,1H).

LRMS (Electrospray): 513 (M+Na)$^+$.

EXAMPLE 48

N-Hydroxy-4-methoxy-2(R,S)-[4-(3-methyl-4-phenylphenyl)-1,2,3,6-tetrahydropyridin-1-ylsulphonyl]butanamide Obtained as a colourless solid (39%), m.p. 135–136° C., from the title compound of Preparation 124, using the procedure of Example 19, except that the residue was purified by flash chromatography using dichloromethane:methanol (97:3) as eluant, prior to crystallisation from diisopropyl ether. δ(DMSO$_{d6}$): 2.10 (m,2H), 2.23 (s,3H), 2.57 (m,2H),3.20 (s,4H), 3.36 (m,1H), 3.48 (m,2H), 3.87 (dd,1H), 3.98 (m,2H), 6.20 (brs,1H), 7.16 (d,1H), 7.32 (m,5H), 7.43 (m,2H), 9.22 (brs,1H), 10.95 (brs,1H).

LRMS Thermospray: 444 (M)$^+$.

EXAMPLE 49

N-Hydroxy-4-[4-(3-methyl-4-phenylphenyl)-1,2,3,6-tetrahydropyridin-1-ylsulphonyl]tetrahydropyran-4-carboxymide Obtained as a colourless solid (91%), m.p. 188–190° C., from the title compound of Preparation 126, using the procedure of Example 38. Found: C, 61.89; H, 6.15; N, 5.94. C$_{24}$H$_{28}$N$_2$O$_5$S; 0.50 H$_2$O requires C, 61.91; H, 6.28; N, 6.02%. δ(DMSO$_{d6}$): 1.95 (m,2H), 2.22 (s,3H), 2.39 (d,2H), 2.50 (m,2H), 3.20 (t,2H), 3.48 (brs,2H), 3.87 (dd,2H), 4.00 (brs,2H), 6.17 (brs,1H), 7.16 (d,1H), 7.31 (m,5H), 7.42 (m,2H).9.22 (brs,1H), 11.05 (brs,1H).

LRMS (APCI): 457 (M+H)$^+$.

EXAMPLE 50

N-Hydroxy-2-{4-[4-(3-methoxyphenyl)-3-methylphenyl]piperidin-1-ylsulphonyl}indane-2-carboxymide Obtained as a colourless solid (63%), m.p. 199–202° C., from the title compound of Preparation 130, using the procedure of Example 19, but with crystallisation of the residue from diisopropyl ether. Found: C, 66.25; H, 6.18; N, 5.18. C$_{29}$H$_{32}$N$_2$O$_5$S; 0.30 H$_2$O requires C,61.21; H, 6.25; N, 5.33%. δ(DMSO$_{d6}$): 1.55 (m,2H), 1.76 (m,2H), 2.20 (s,3H), 2.54 (m,1H), 2.89 (t,2H), 3.48 (m,2H), 3.77 (m,7H), 6.87 (m,3H), 7.07–7.35 (m,8H), 9.10 (brs,1H), 11.05 (brs,1H).

EXAMPLE 51

N-Hydroxy-1-{4-[4-(3-methoxyphenyl)-3-methylphenyl]piperidin-1-ylsulphonyl}cyclobutanecarboxymide Obtained as a colourless solid (52%), m.p. 157–160° C., from the title compound of Preparation 132, using the procedure of Example 50. Found: C, 62.79; H, 6.60; N, 5.93. C$_{24}$H$_{30}$N$_2$O$_5$S requires C, 62.86; H, 6.59; N, 6.11%. δ(DMSOdC): 1.60 (m,2H), 1.78 (m,3H), 1.93 (m,1H), 2.20 (s,3H), 2.57 (m,5H), 2.97 (t,2H), 3.72 (m,2H), 3.77 (s,3H), 6.87 (m,3H), 7.11 (s,2H), 7.15 (s,1H), 7.36 (t,1H), 9.10 (brs,1H), 10.92 (brs,1H).

LRMS (Thermospray): 459 (M+H)$^+$.

EXAMPLE 52

N-Hydroxy-4-{4-[4-(3-methoxyphenyl)-3-methylphenyl]piperidin-1-ylsulphonyl}-1-methylpiperidine-4-carboxymide Obtained as a colourless solid (13%), from the title compound of Preparation 134, using the procedure of Example 19, except that the residue was purified by flash chromatography using dichloromethane:methanol:concentrated aqueous ammonia solution (90:10:1) as eluant. δ(CDCl$_3$): 1.79 (m,2H), 1.90 (m,2H), 2.16 (m,2H), 2.27 (s,3H), 2.30 (s,3H), 2.33 (m,4H), 2.64 (m,1H), 2.91 (brd, 2H), 3.10 (t,2H), 3.83 (s,3H), 3.91 (m,2H), 6.88 (m,3H), 7.08 (m,2H), 7.18 (d,1H), 7.30 (t,1H).

LRMS (Thermospray): 502 (M+H)$^+$.

EXAMPLE 53

N-Hydroxy-3-phenyl-2(R,S)-[4-(4-phenylphenyl)-1,2,3,6-tetrahydropyridin-1-ylsulphonyl]propanamide Obtained as a colourless solid (31%), m.p. 202–205° C., from the title compound of Preparation 136, using the procedure of Example 19, except that the residue was triturated with dichloromethane. Found: C, 66.05; H, 5.82; N, 6.15. C$_{26}$H$_{26}$N$_2$O$_4$S; 0.50 H$_2$O requires C,66.22; H, 5.77; N, 5.94%. δ(DMSO$_{d6}$): 2.60 (m,2H), 3.15 (m,2H), 3.57 (m,2H), 4.03 (m,3H), 6.07 (brs,1H), 7.16–7.36 (m,6H), 7.45 (m,2H), 7.57 (m,2H), 7.65 (m,4H), 9.17 (brs,1H), 10.70 (brs,1H).

LRMS (APCI): 463 (M+H)$^+$.

EXAMPLE 54

N-Hydroxy-2-[4-(4-phenylphenyl)-1,2,3,6-tetrahydropyridin-1-ylsulphonyl]indane-2-carboxymide Obtained as a colourless solid (27%), m.p. 159–161° C., from the title compound of Preparation 138, using the procedure of Example 19, except that the residue was purified by flash chromatography using dichloromethane:methanol (98:2) as eluant, followed by trituration with diisopropyl ether. δ(DMSO$_{d6}$): 2.55 (m,2H), 3.41 (m,2H), 3.53 (d,2H); 3.77 (d,2H), 3.96 (m,2H), 6.18 (brs, 1H), 7.16 (m,2H), 7.23 (m,2H), 7.34–7.53 (m,5H), 7.65 (m,4H), 9.15 (brs,1H), 11.10 (brs,1H).

LRMS (APCI): 463 (M+H)$^+$.

EXAMPLE 55

N-Hydroxy-2-{4-[4-(3chloro-4-fluorophenyl)-3-methylphenyl]-1,2,3,6-tetrahydropyridin-1-ylsulphonyl}acetamide Obtained as a colourless solid (60%), m.p. 181–183° C. (crystallised from ether), from the title compound of Preparation 142, using the procedure of Example 17, except that tetrahydrofuran was used as a co-solvent for the reaction. Found: C, 54.65; H, 4.61; N, 6.13. C$_{20}$H$_{20}$ClFN$_2$O$_4$S requires C, 54.73; H, 4.59; N, 6.38%. δ(DMSO$_{d6}$): 2.24 (s,3H), 2.60 (m,2H), 3.47 (t,2H), 3.90 (s,2H), 3.97 (m,2H), 6.22 (brs,1H), 7.20 (d,1H), 7.30–7.40 (m,3H), 7.45 (t,1H), 7.56 (m,1H), 9.20 (brs,1H), 10.80 (brs,1H).

LRMS (APCI): 439 (M+H)$^+$.

EXAMPLE 56

N-Hydroxy-2-{4-[4-(1,3-benzodioxol-5-yl)-3-methylphenyl]-1,2,3,6-tetrahydropyridin-1-ylsulphonyl}acetamide Obtained as a colourless solid (69%), m.p. 165–167° C., from the title compound of Preparation 146, using the procedure of Example 45. Found: C, 58.60; H, 5.10; N, 6.01. $C_{21}H_{22}N_2O_6S$ requires C, 58.59; H, 5.15; N, 6.51%. δ($DMSO_{d6}$): 2.22 (s,3H), 2.59 (m,2H), 3.46 (t,2H), 3.90 (s,2H), 3.96 (m,2H), 6.04 (s,2H), 6.20 (brs,1H), 6.76 (d,1H), 6.89 (s,1H), 6.95 (d,1H), 7.15 (d,1H), 7.28 (d,1H), 7.35 (s,1H), 9.20 (brs,1H), 10.80 (brs,1H).

LRMS (APCI): 431 $(M+H)^+$.

EXAMPLE 57

N-Hydroxy-2-{4-[4-(2-fluorophenyl)-3-methylphenyl]-1,2,3,6-tetrahydropyridin-1-ylsulphonyl}acetamide Obtained as a colourless solid (32%), m.p. 160–163° C., from the title compound of Preparation 150, using the procedure of Example 17, except that tetrahydrofuran was used as a co-solvent for the reaction. δ($DMSO_{d6}$): 2.12 s,3H), 2.60 (m,2H), 3.48 (t,2H), 3.84 (s,2H), 3.98 (m,2H), 6.21 (brs,1H), 7.17 (d,1H), 7.23–7.35 (m,4H), 7.40 (s,1H), 7.42 (m,1H).

LRMS (APCI): 405 $(M+H)^+$.

EXAMPLE 58

N-Hydroxy-2-{4-[4-(3,4-dimethoxyphenyl)-3-methylphenyl]-1,2,3,6-tetrahydropyridin-1-ylsulphonyl}acetamide Obtained as a colourless solid (61%), m.p. 172–174° C., from the title compound of Preparation 151, using the procedure of Example 57. Found: C, 59.36; H, 6.08; N, 5.87. $C_{22}H_{28}N_2O_6S$ requires C, 59.18; H, 5.87; N, 6.27%. δ($DMSO_{d6}$): 2.25 (s,3H), 2.60 (m,2H), 3.48 (t,2H), 3.75 (s,3H), 3.78 (s,3H), 3.78 (s,3H), 3.90 (s,2H), 3.96 (m,2H), 6.19 (brs,1H), 6.82 (d,1H), 6.88 (s,1H), 7.00 (d,1H), 7.19 (d,1H), 7.29 (d,1H), 7.36 (s,1H), 9.20 (brs,1H), 10.80 (brs, 1H).

LRMS (APCI): 447 $(M+H)^+$.

EXAMPLE 59

N-Hydroxy-2-{4-[4-(indan-5-yl)-3-methylphenyl]-1,2,3,6-tetrahydropyridin-1-ylsulphonyl}acetamide Obtained as a colourless solid (58%), m.p. 149–152° C., from the title compound of Preparation 152, using the procedure of Example 17. 5($DMSO_{d6}$): 2.03 (m,2H), 2.22 (s,3H), 2.59 (m,2H), 2.90 (m,4H), 3.47 (m,2H), 3.90 (s,2H), 3.96 (m,2H), 6.19 (brs,1H), 7.05 (d,1H), 7.15 (m,2H), 7.23–7.30 (m,2H), 7.36 (s,1H), 9.20 (brs,1H), 10.80 (brs, 1H).

LRMS (APCI): 427 $(M+H)^+$.

EXAMPLE 60

N-Hydroxy-2-{4-[3-methyl-4-(3-trifluoromethoxyphenyl)phenyl]-1,2,3,6-tetrahydropyridin-1-ylsulphonyl}acetamide Obtained as a colourless solid (13%), m.p. 154° C. (crystallised from dichloromethane-diisopropyl ether), from the title compound of Preparation 153, using the procedure of Example 17. δ($DMSO_{d6}$): 2.23 (s,3H), 2.59 (m,2H), 3.47 (t,2H), 3.90 (s,2H), 3.96 (m,2H), 6.22 (brs,1H), 7.20 (d,1H), 7.30–7.40 (m,5H), 7.58 (t,1H), 9.20 (brs,1H), 10.80 (brs, 1H).

LRMS (Thermospray): 488 $(M+NH_4)^+$.

EXAMPLE 61

N-Hydroxy-2-[4-(4-(4-phenyl-3-trifluoromethylphenyl)-1,2,3,6-tetrahydropyridin-1-ylsulphonyl]acetamide Obtained as a colourless solid (43%), m.p. 143–145° C., from the title compound of Preparation 157, using the procedure of Example 17. Found: C, 54.63; H, 4.35; N, 5.90. $C_{20}H_{19}F_3N_2O_4S$ requires C, 54.54; H, 4.35; N, 6.36%. δ($DMSO_{d6}$): 2.66 (m,2H), 3.50 (m,2H), 3.93 (s,2H), 4.00 (m,2H), 6.38 (brs,1H), 7.30 (m,2H), 7.35–7.47 (m,4H), 7.79 (d,1H), 7.82 (s,1H), 9.20 (brs,1H), 10.80 (brs,1H).

LRMS (Thermospray): 458 $(M+NH_4)^+$.

EXAMPLE 62

N-Hydroxy-2-{4-[4-(2,2-dimethyl-1,3-benzodioxol-5-yl)-3-methylphenyl]-piperidin-1-ylsulphonyl}-2-methylpropionamide Obtained as a colourless solid (52%), m.p. 184–186° C., from the title compound of Preparation 161, using the procedure of Example 19. δ($DMSO_{d6}$): 1.47 (s,6H), 1.60 (m,2H), 1.65 (s,6H), 1.78 (m,2H), 2.20 (s,3H), 2.65 (m,1H), 3.04 (m,2H), 3.73 (m,2H), 6.68 (d,1H), 6.77 (s,1H), 6.83 (d,1H), 7.07 (s,2H), 7.12 (s,1H), 9.00 (brs,1H), 10.75 (brs, 1H).

LRMS (APCI): 489 $(M+H)^+$.

EXAMPLE 63

N-Hydroxy-2-{4-[4-(1,2-dimethylbenzimidazol-5-yl)-3-methylphenyl]piperidin-1-ylsulphonyl]-2-methylpropionamide Obtained as a colourless solid (22%), m.p. 213–215° C., from the title compound of Preparation 165, using the procedure of Example 19. δ($DMSO_{d6}$): 1.48 (s,6H), 1.62 (m,2H), 1.80 (m,2H), 2.20 (s,3H), 2.52 (s,3H), 2.67 (m,1H), 3.08 (t,2H), 3.73 (s,3H), 3.75 (m,2H), 7.08–7.15 (m,4H), 7.39 (s, 1H), 7.47 (d,1H), 9.00 (brs,1H), 11.75 (brs,1H).

LRMS (Thermospray): 485 $(M+H)^+$.

EXAMPLE 64

N-Hydroxy-2-{4-[4-(3-cyanophenyl)-3-methylphenyl]piperidin-1-ylsulphonyl}-2-methylpropionamide Palladium on barium sulfate (5%, 10 mg) was added to a stirred solution of the title compound of Preparation 168 (70 mg, 0.13 mmol) in methanol (2 ml), then the reaction mixture hydrogenated at 345 kPa (50 psi) pressure for about 20 hours. A further portion of palladium on barium sulfate (5%, 10 mg) was added and hydrogenation continued for an additional 4 days. The catalyst was removed by filtration, the solvent evaporated under reduced pressure and the residue flash chromatographed, using methanol:dichloromethane (5:95) as eluant, to give the title compound (13 mg, 23%) as a colourless amorphous solid. δ($CDCl_3$): 1.63 (s,6H), 1.63–1.95 (m,4H), 2.26 (s,3H), 2.67 (m,1H), 3.10 (m,2H), 3.96 (m,2H), 7.04–7.20 (m,3H), 7.50–7.70 (m,4H)

IR (KBr) 2240 $cm^{-1}$ for cyano.

EXAMPLE 65

N-Hydroxy-2-{4-[4-(5-ethoxypyridin-3-yl)-3-methylphenyl]piperidin-1-ylsulphonyl}-2-methylpropionamide Obtained as a colourless foam (62%), from the title compound of Preparation 172, using the procedure of Example 19, except that the residue was purified by flash chromatography, using dichloromethane:ethanol ( 95:5) as eluant. δ(DMSO$_{d6}$): 1.32 (t,3H), 1.48 (s,6H), 1.61 (m,2H), 1.79 (m,2H), 2.21 (s,3H), 2.67 (m,1H), 3.05 (t,2H), 3.75 (d,2H), 4.13 (q,2H), 7.15–7.20 (m,3H), 7.30 (s,1H), 8.10 (s,1H), 8.23 (s,1H), 8.98 (brs,1H), 10.75 (brs,1H).

LRMS (Thermospray): 462 (M+H)$^+$.

EXAMPLE 66

N-Hydroxy-2-{4-[4-(3-[2-hydroxyethoxy]phenyl)-3-methylphenyl]piperidin-1-ylsulphonyl}-2-methylpropanamide O-(7-Azabenzotriazol-1-yl)-1,1,3,3-tetramethyluronium hexafluorophosphate (510 mg, 1.15 mmol) was added to a stirred solution of the title compound of Preparation 178 (530 mg, 0.76 mmol) and N-ethyldiisopropylamine (0.20 ml, 0.9 mmol) in anhydrous dimethylformamide (4 ml), under nitrogen, at room temperature. After 15 minutes, hydroxylamine hydrochloride (188 mg, 2.2 mmol) and N-ethyldiisopropylamine (0.6 ml, 2.7 mmol) were added and the reaction mixture stirred for about 16 hours, then partitioned between ethyl acetate and aqueous phosphate buffer (pH 7). The organic phase was separated, washed with water, dried (MgSO$_4$) and evaporated under reduced pressure. The residue was dissolved in anhydrous tetrahydrofuran (15 ml), tetra-n-butylammonium fluoride (1.4 ml of a 1.0M solution in tetrahydrofuran; 1.4 mmol) added and the resulting solution stirred at room temperature for 1.5 hours, then partitioned between ethyl acetate and aqueous phosphate buffer (pH 7). The organic phase was separated, washed with water, dried (MgSO$_4$) and evaporated under reduced pressure. Purification of the residue by flash chromatography, using dichloromethane:methanol:concentrated aqueous ammonia solution (90:10:1). as eluant, followed by crystallisation from methanol-water, provided the product as a colourless solid (155 mg, 43%), m.p. 147–150° C. Found: C, 60.26; H, 6.81; N, 5.76. C$_{24}$H$_{32}$N$_2$O$_6$S requires C, 60.48; H, 6.77; N, 5.88%. δ(DMSO$_{d6}$): 1.49 (s,6H), 1.63 (m,2H), 1.80 (m,2H), 2.21 (s,3H), 2.67 (m,1H), 3.08 (t,2H), 3.74 (m,4H), 4.02 (t,2H), 4.83 (t,1H), 6.82–6.92 (m,3H), 7.10 (s,2H), 7.16 (s,1H), 7.30 (t,1H), 9.00 (brs,1H), 10.75 (brs,1H).

PREPARATION 1 t-Butyl 4-hydroxy-4-phenylphenyl)piperidin-1-carboxylate

A 2.5M solution of n-butyllithium in hexane (8 ml, 20 mmol) was added over about 10 minutes to a stirred mixture of 4-bromobiphenyl (4.66 g, 20 mmol), anhydrous ether (100 ml) and anhydrous tetrahydrofuran (10 ml), under nitrogen, at about −75° C. After a further 1 hour, a solution of t-butyl 4-oxopiperidin-1-carboxylate (3.98 g, 20 mmol) in anhydrous tetrahydrofuran (10 ml) was added at such a rate that the reaction temperature was maintained below −60° C.

The reaction mixture was stirred at about −75° C. for 3 hours and quenched with aqueous ammonium chloride solution, then the organic phase was separated, washed with water, dried (MgSO$_4$) and evaporated under reduced pressure. Crystallisation of the residue from diisopropyl ether gave the title compound (4.29 g) as a colourless solid, m.p. 144–146° C. δ(CDCl$_3$): 1.50 (s,9H), 1.78 (d,2H), 2.06 (m,2H), 3.28 (dd,2H), 4.06 (m,2H), 7.35 (t,1H), 7.43 (m,2H), 7.50–7.65 (m,6H).

LRMS (APCI): 354 (M+H)$^+$.

PREPARATION 2

4-(4-Phenylphenyl)-1,2,3,6-tetrahydropyridine

Trifluoroacetic acid (20 ml) was added to a stirred solution of the title compound of Preparation 1 (4.2 g, 11.9 mmol) in dichloromethane (20 ml) at room temperature. After a further 3 hours, the reaction mixture was evaporated under reduced pressure and the residue basified with 1M aqueous sodium hydroxide solution. The resulting mixture was extracted with dichloromethane, then the combined extracts washed with water, dried (MgSO$_4$) and evaporated under reduced pressure to yield the title compound (2.79 g) as a colourless solid. δ(CDCl$_3$): 1.53 (s,1H), 2.50 (m,2H), 3.14 (t,2H), 3.58 (m,2H), 6.20 (brs,1H), 7.34 (t,1H), 7.45 (m,4H), 7.60 (m,4H).

LRMS (Thermospray): 236 (M+H)$^+$.

PREPARATION 3

1-Benzyl-4-hydroxy4-(4-phenylphenyl)piperidine

A 1.6M solution of n-butyllithium in hexane (39 ml, 63 mmol) was added to a stirred solution of 4-bromobiphenyl (11.7 g, 50 mmol) in anhydrous tetrahydrofuran (50 ml), under nitrogen, at about −50° C., whilst ensuring that the reaction temperature was kept below −40° C. After a further 1 hour, a solution of 1-benzyl-4-oxopiperidine (10.4 g, 55 mmol) in anhydrous tetrahydrofuran (30 ml) was added at such a rate that the reaction temperature was maintained below −40° C. The cooling bath was then removed and, after a further 1 hour, the reaction mixture was partitioned between dichloromethane (400 ml) and brine (200 ml). The organic phase was separated, washed with water, dried (MgSO$_4$) and evaporated under reduced pressure, then the residue crystallised from ethyl acetate to provide the title compound (13.9 g) as a colourless solid. δ(DMSO$_{d6}$): 1.80 (d,2H), 2.52 (m,2H), 3.24 (m,4H), 4.33 (d,2H), 7.28–7.75 (m,14H), 11.30 (brs, 1H).

PREPARATION 4

1-Benzyl-4-(4-phenylphenyl)-1,2,3,6-tetrahydropyridine

A solution of the title compound of Preparation 3 (13.8 g, 40.2 mmol) and p-toluenesulphonic acid (15.3 g, 80.4 mmol) in toluene (100 ml) was heated under reflux in a Dean-Stark apparatus until water removal was complete (ca. 2 hours), then allowed to cool and diluted with water (200 ml). The resulting mixture was basified with concentrated aqueous ammonia solution and extracted with dichloromethane (4×200 ml), then the combined extracts dried (MgSO$_4$) and evaporated under reduced pressure to furnish the title compound (10.6 g) as an off-white solid. δ(CDCl$_3$): 2.57 (m,2H), 2.70 (m,2H),:3.18 (m,2H), 3.62 (s,2H), 6.10 (brs, 1H), 7.20–7.60 (m,14H).

PREPARATION 5

4-(4-Phenylphenyl)piperidine

A stirred mixture of the title compound of Preparation 4 (5.07 g, 15.6 mmol), ammonium formate (4 g, 62 mmol), palladium hydroxide on carbon (500 mg) and methanol (50 ml) was heated under reflux for 4.5 hours, allowed to cool and filtered. The filtrate was evaporated under reduced pressure and the residue partitioned between 2M aqueous sodium hydroxide solution and dichloromethane. The organic phase was separated and combined with dichloromethane extracts (3×100 ml) of the aqueous phase, then the combined dichloromethane solutions dried (MgSO$_4$) and evaporated under pressure to afford the title compound (3.5 g) as an off-white solid, m.p. 104–107° C. δ(CDCl$_3$): 1.50 (brs,1H), 1.63 (m,2H), 1.83 (m,2H), 2.62 (m,1H), 2.75 (m,2H), 3.19 (d,2H), 7.25 (m,3H), 7.40.(m,2H), 7.53 (m,4H).

PREPARATION 6 t-Butyl 4-hydroxy-4-(3-methyl-4-phenylphenyl) piperidine-1-carboxylate

Obtained as a colourless solid (60%), m.p. 142–144° C., from 4-bromo-2-methylbiphenyl (J.Amer.Chem.Soc., 1926, 48, 1372) and t-butyl 4-oxopiperidin-1-carboxylate, using the procedure of Preparation 1. δ(CDCl$_3$): 1.48 (s,9H), 1.78 (m,2H), 2.04 (m,2H), 2.30 (s,3H), 3.28 (m,2H), 4.05 (m,2H), 7.20–7.42 (m,8H).

LRMS (Thermospray): 468 (M+H)$^+$.

PREPARATION 7

4(3-Methyl-4-phenylphenyl)-1,2,3,6-tetrahydropyridine

Obtained as a colourless solid (90%) from the title compound of Preparation 6, using the procedure of Preparation 2. δ(CDCl$_3$): 1.85 (s,1H), 2.28 (s,3H), 2.50 (m,2H), 3.14 (t,2H), 3.57 (m,2H), 6.18 (brs, 1H), 7.20–7.42 (m,8H).

LRMS (APCI): 250 (M+H)$^+$.

PREPARATION 8

Methyl 2-[4-(4-phenylphenyl)-1,2,3,6-tetrahydropyridin-1-ylsulphonyl]acetate

A solution of methyl chlorosulphonylacetate (0.35 g, 2 mmol) in dichloromethane (2 ml) was added dropwise to a stirred solution of the title compound of Preparation 2 (470 mg, 2 mmol) and 1,8-diazabicyclo[5.4.0]undec-7-ene (0.3 ml, 2 mmol) in dichloromethane (8 ml) at about 0° C, the cooling bath removed and the reaction mixture stirred at room temperature for 4 hours, then diluted with dichloromethane. The resulting mixture was washed with 0.1 M hydrochloric acid, dried (MgSO$_4$) and evaporated under reduced pressure. The residue was purified by flash chromatography, using dichloromethane as eluant, followed by crystallisation from diisopropyl ether, to give the title compound (250 mg) as a colourless solid, m.p. 182–183° C. Found: C, 64.32; H, 5.59; N, 3.77. C$_{20}$H$_{21}$NO$_4$S requires C, 64.66; H, 5.70; N, 3.77%. δ(CDCl$_3$): 2.66 (m,2H), 3.62 (t,2H), 3.78 (s,3H), 3.99 (s,2H), 4.08 (m,2H), 6.08 (brs, 1H), 7.32 (m,1H), 7.38–7.44 (m,4H), 7.53–7.60 (m,4H).

LRMS (APCI): 372 (M+H)$^+$.

PREPARATION 9

Methyl 2-[4-(3-methyl-4-phenylphenyl)-1,2,3,6-tetrahydropyridin-1-ylsulphonyl]acetate Obtained as a colourless solid (30%), m.p. 104–105° C., from the title compound of Preparation 7 and methyl chlorosulphonylacetate, using the procedure of Preparation 8. Found: C, 65.18; H, 6.03; N, 3.59. C$_{21}$H$_{23}$NO$_4$S requires C, 65.43; H, 6.01; N, 3.63%. δ(CDCl$_3$): 2.28 (s,3H), 2.68 (m,2H), 3.64 (t,2H), 3.81 (s,3H), 4.02 (s,2H), 4.10 (m,2H), 6.08 (brs,1H), 7.20–7.47 (m,8H).

LRMS (Thermospray): 386 (M+H)$^+$.

PREPARATION 10

Methyl 2-[4-(4-phenylphenyl)piperidin-1-ylsulphonyl]acetate

Obtained as a colourless solid (27%), m.p. 169–170° C., from the title compound of Preparation 5 and methyl chlorosulphonylacetate, using the procedure of Preparation 8. Found: C, 63.99; H, 6.18; N, 3.69. C$_{20}$H$_{23}$NO$_4$S requires C, 64.32; H, 6.21; N, 3.75. δ(CDCl$_3$): 1.83 (m,2H), 1.95 (m,2H), 2.68 (m,1H), 3.00 (t,2H), 3.80 (s,3H), 3.95 (s,2H), 3.97 (m,2H), 7.20–7.35 (m,3H), 7.40 (t,2H), 7.50–7.60 (m,4H).

PREPARATION 11

Methyl 2-(4-phenyl-1,2,3,6-tetrahydropyridin-1-ylsulphonyl)acetate

Obtained as a colourless solid (20%), m.p. 93–94° C., from 4-phenyl-1,2,3,6-tetrahydropyridine and methyl chlorosulphonylacetate, using the procedure of Preparation 8. Found: C, 56.86; H, 5.79; N, 4.76, C$_{14}$H$_{17}$NO$_4$S requires C, 56.93; H, 5.80; N, 4.74%. δ(CDCl$_3$): 2.62 (m,2H), 3.60 (t,2H), 3.78 (s,3H), 3.99 (s,2H), 4.05 (m,2H), 6.00 (brs,1H), 7.22–7.35 (m,5H).

PREPARATION 12

Methyl 2-(4-phenylpiperidin-1-ylsulphonyl)acetate

Obtained as a colourless solid (35%), m.p. 98–100° C., from 4-phenylpiperidine and methyl chlorosulphonylacetate, using the procedure of Preparation 8. Found: C, 56.43; H, 6.41; N, 4.64. C$_{14}$H$_{19}$NO$_4$S requires C, 56.55; H, 6.44; N, 4.71%. δ(CDCl$_3$): 1.80 (m,2H), 1.90 (m,2H), 2.60 (m,1H), 2.97 (m,2H), 3.80 (s,3H), 3.92 (s,2H), 3.93 (m,2H), 7.15–7.33 (m,5H).

PREPARATION 13

Methyl 2-(4-benzylpiperidin-1-ylsulphonyl)acetate

Obtained as an amorphous solid (24%) from 4-benzylpiperidine and methyl chlorosulphonylacetate, using the procedure of Preparation 8, but with an elution gradient of dichloromethane:methanol (100:0 to 95:5) for the chromatographic purification step. δ(CDCl$_3$): 1.30 (m,2H), 1.62 (m,1H), 1.70 (m,2H), 2.54 (d,2H), 2.78 (t,2H), 3.73 (s,3H), 3.76 (m,2H), 3.88 (s,2H), 7.08 (d,2H), 7.17 (t,1H), 7.24 (m,2H).

LRMS (APCI): 312 (M+H)$^+$.

PREPARATION 14

Methyl 2(R,S)-[4-(4-phenylphenyl)-1,2,3,6-tetrahydropyridin-1l-ylsulphonyl]pent-4-enoate 60% Sodium hydride in a mineral oil dispersion (21 mg, 0.53 mmol) was added to a stirred solution of the title compound of Preparation 8 (180 mg, 0.48 mmol) in a mixture of anhydrous tetrahydrofuran (1 ml) and anhydrous dimethylformamide (1 ml), under nitrogen, at room temperature. After 30 minutes, allyl bromide (0.05 ml, 0.53 mmol) was added and stirring continued for a further 2 hours, then the resulting mixture was partitioned between ethyl acetate and aqueous phosphate buffer (pH 7). The organic phase was separated, washed with water, dried (MgSO$_4$) and evaporated under reduced pressure, then the residue triturated with diisopropyl ether to yield the title compound (170 mg) as a colourless solid. δ(CDCl$_3$): 2.60–2.85 (m,4H), 3.55–3.77 (m,2H), 3.79 (s,3H), 4.03 (dd,1H), 4.12 (m,2H), 5.10–5.22 (m,2H), 5.74 (m,1H), 6.08 (brs, 1H), 7.36 (m,1H), 7.43 (m,4H), 7.60 (m,4H).

LRMS (APCI): 411 (M+H)$^+$.

PREPARATION 15

2(R,S)-[4-(4-Phenylphenyl)-1,2,3,6-tetrahydropyridin-1l-ylsulphonyl]pent4-enoic acid 1M Aqueous sodium hydroxide solution (1.2 ml, 1.2 mmol) was added to a stirred solution of the title compound of Preparation 14 (160 mg, 0.39 mmol) in a mixture of tetrahydrofuran (5 ml) and methanol (10 ml). The resulting solution was heated at 50° C. for 3 hours, then evaporated under reduced pressure and the residue dissolved in water. This aqueous solution was acidified with concentrated hydrochloric acid and the resulting emulsion extracted with ethyl acetate. The combined extracts were dried (MgSO$_4$) and evaporated under reduced pressure, then the residue purified by flash chromatography, using an elution gradient of ethyl acetate:methanol:glacial acetic acid (100:0:0 to 97:3:0 to 96:3:1), followed by trituration with hexane, to provide the title compound (90 mg) as a colourless, amorphous solid. δ(CDCl$_3$): 2.60–2.87 (m,4H), 3.60–3.72 (m,2H), 4.05 (dd,1H), 4.12 (s,2H), 5.10–5.23 (m,2H), 5.79 (m,1H), 6.06 (brs,1H), 7.30–7.43 (m,5H), 7.50–7.60 (m,4H).

LRMS (Thermospray): 415 (M+NH$_4$)$^+$.

PREPARATION 16

Methyl 2(R,S)-[4-(3-methyl4phenylphenyl)-1,2,3,6-tetrahydropyridin-1-ylsulphonyl]pent4-enoate Obtained as a solid (67%) from the title compound of Preparation 9 and allyl bromide, using the procedure of Preparation 14, but with flash chromatography, employing an elution gradient of hexane:ethyl acetate (100:0 to 80:2)), as the purification step. δ(CDCl$_3$): 2.30 (s,3H), 2.68 (m,2H), 2.85 (m,2H), 3.56 (m,1H), 3.70 (m,1H), 3.80 (s,3H), 4.03 (dd,1H), 4.10 (m,2H), 5.10–5.22 (m,2H), 5.73 (m,1H), 6.06 (brs,1H), 7.20–7.45 (m,8H).

LRMS (Thermospray): 426 (M+H)$^+$.

PREPARATION 17

2(R,S)-[4-(3-Methyl-4-phenylphenyl)-1,2,3,6-tetrahydropyridin-1-yl-ylsulphonyl]pent-4-enoic acid Obtained as an amorphous solid (46%) from the title compound of Preparation 16, using the procedure of Preparation 15. δ(CDCl$_3$): 2.30 (s,3H), 2.66 (m,2H), 2.87 (m,2H), 3.60 (m,1H), 3.70 (m,1H), 4.03 (dd,1H), 4.12 (m,2H), 5.13–5.25 (m,2H), 5.78 (m,1H), 6.04 (brs,1H), 7.20–7.43 (m,8H).

LRMS (Thermospray): 368 (M+H—CO$_2$)$^+$.

PREPARATION 18

Methyl 5-phenyl-2(R,S)-[4-(4-phenylphenyl)-1,2,3,6-tetrahydropyridin-1-ylsulphonyl]pentanoate Obtained as a colourless solid (65%), m.p. 146–148° C., from the title compound of Preparation 8 and 1-bromo-3-phenylpropane, using the procedure of Preparation 14. δ(CDCl$_3$): 1.70 (m,2H), 2.15 (m,2H), 2.64 (m,4H), 3.52 (m,1H), 3.63 (m,1H), 3.79 (s,3H), 3.98 (dd,1H), 4.06 (m,2H), 6.05 (m,1H), 7.10–7.50 (m,10H), 7.60 (m,4H).

LRMS (Thermospray): 490 (M+H)$^+$.

PREPARATION 19

2-Methyl-2-[4-(4-phenylphenyl)-1,2,3,6-tetrahydropyridin-1-ylsulphonyl]propanoic acid 60% Sodium hydride in a mineral oil dispersion (48 mg, 1.2 mmol) was added to a stirred solution of the title compound of Preparation 8 (150 mg, 0.4 mmol) in a mixture of anhydrous tetrahydrofuran (3 ml) and anhydrous dimethylformamide (1 ml), under nitrogen, at room temperature. After 30 minutes, methyl p-toluenesulphonate (220 mg, 1.2 mmol) was added and stirring continued for a further 20 hours, then the resulting mixture was partitioned between ethyl acetate and water. The aqueous phase was acidified with 2M hydrochloric acid and extracted with dichloromethane (3×50 ml). The combined extracts were dried (MgSO$_4$) and evaporated under reduced pressure, then the residue purified by flash chromatography, using dichloromethane:methanol:glacial acetic acid (89:10:1) as eluant, to furnish the title compound (60 mg) as a pale yellow, amorphous solid. δ(CDCl$_3$): 1.70 (s,6H), 2.63 (m,2H), 3.67 (m,2H), 4.17 (m,2H), 6.08 (brs,1H), 7.25–7.70 (m,9H).

PREPARATION 20

Methyl 1-[4-(3-methyl-4-phenylphenyl)-1,2,3,6-tetrahydropyridin-1-ylsulphonyl] cyclopentanecarboxylate 60% Sodium hydride in a mineral oil dispersion (43 mg, 1.07 mmol) was added to a stirred solution of the title compound of Preparation 9 (380 mg, 0.99 mmol) in anhydrous dimethylformamide (5 ml), under nitrogen, at room temperature. After 30 minutes, 1,4-diiodobutane (0.14 ml, 1.06 mmol) was added and stirring continued for 18 hours, then more 60% sodium hydride dispersion (43 mg, 1.07 mmol) was added and stirring continued for a further 4 hours. The resulting mixture was partitioned between ethyl acetate and water, then the organic phase separated, washed with water, dried (MgSO$_4$) and evaporated under reduced pressure. The residue was purified by flash chromatography, using hexane:ethyl acetate (9:1) as eluant, to afford the title compound (340 mg) as an amorphous solid. δ(CDCl$_3$): 1.64 (m,2H), 1.88 (m,2H), 2.28 (s,3H), 2.37 (m,2H), 2.52 (m,2H), 2.63 (m,2H), 3.60 (t,2H), 3.80 (s,3H), 4.10 (m,2H), 6.03 (brs,1H), 7.20–7.43 (m,8H).

LRMS (Thermospray): 440 (M+H)$^+$.

PREPARATION 21

1-[4-(3-Methyl-4-phenylphenyl)-1,2,3,6-tetrahydropyridin-1-ylsulphonyl] cyclopentanecarboxylic acid Obtained as a solid (54%) from the title compound of Preparation 20, using the procedure of Preparation 15, but with an elution gradient of hexane:ethyl acetate (75:25 to 0:100) for the chromatographic purification step. δ(CDCl$_3$): 1.65 (m,2H), 1.88 (m,2H), 2.27 (s,3H), 2.39 (m,2H), 2.50 (m,2H), 2.63 (m,2H), 3.64 (t,2H), 4.12 (m,2H), 6.03 (brs, 1H), 7.20–7.43 (m,8H).

LRMS (Thermospray): 426 (M+H)$^+$.

PREPARATION 22

Methyl 2-ethyl-2-[4-(4-phenylphenyl)-1,2,3,6-tetrahydropyridin-1-yl-ylsulphonyl]butanoate This was conducted as for Preparation 19 and on the same molar scale, using the title compound of Preparation 8 and ethyl iodide. However, in this case, no concomitant ester hydrolysis was apparent and therefore the required product was isolated from the organic phase during work-up and purified by flash chromatography, using dichloromethane as eluant, to give the title compound (125 mg) as a white amorphous solid. $\delta$(CDCl$_3$): 1.04 (t,6H), 2.08–2.26 (m,4H), 2.66 (m,2H), 3.60 (m,2H), 3.80 (s,3H), 4.10 (m,2H), 6.08 (brs,1H), 7.35 (m,1H), 7.43 (m,4H), 7.60 (m,4H).

PREPARATION 23

2-Ethyl-2-[4-(4-phenylphenyl)-1,2,3,6-tetrahydroyridin-1-ylsulphonyl]-butanoic acid 1M Aqueous sodium hydroxide solution (1.5 ml, 1.5 mmol) was added to a stirred solution of the title compound of Preparation 22 (120 mg, 0.28 mmol) in a mixture of tetrahydrofuran (5 ml) and methanol (2 ml). The resulting mixture was heated under reflux for 70 hours, allowed to cool to room temperature, acidified with 2M hydrochloric acid and extracted with dichloromethane (3×20 ml). The combined extracts were dried (MgSO$_4$) and evaporated under reduced pressure to yield the title compound (95 mg) as a pale yellow, amorphous solid. $\delta$(CDCl$_3$): 1.10 (t,6H), 2.10–2.28 (m,4H), 2.64 (m,2H), 3.65 (m,2H), 4.15 (m,2H), 6.08 (brs,1H), 7.35 (m,1H), 7.43 (m,4H), 7.58 (m,4H).

PREPARATION 24

Methyl 2(R,S)-[4-(4-phenylphenyl)-1,2,3,6-tetrahydropyridin-1-ylsulphonyl]hexanoate This was conducted essentially as for Preparation 14, using the title compound of Preparation 8 and n-butyl iodide, but employing 1.0 mol.equiv. of sodium hydride, 1-methylpyrrolidin-2-one as solvent and an alkylation reaction time of 70 hours, to provide the title compound (78%) as a colourless solid, m.p. 152–154° C. Found: C, 67.09; H, 6.76; N, 3.22. C$_{24}$H$_{29}$NO$_4$S requires C, 67.42; H, 6.84; N, 3.28%. $\delta$(CDCl$_3$): 0.90 (t,3H), 1.30 (m,4H), 2.05 (m,1H), 2.15 (m,1H), 2.60–2.75 (m,2H), 3.55 (m,1H), 3.70 (m,1H), 3.80 (s,3H), 3.95 (dd,1H), 4.10 (m,2H), 6.08 (brs, 1H), 7.35 (m,1H), 7.43 (m,4H), 7.58 (m,4H). LRMS (Thermospray): 428 (M+H)$^+$.

PREPARATION 25

2(R,S)-[4-(4-Phenylphenyl)-1,2,3,6-tetrahydropyridin-1-ylsulphonyl]-hexanoic acid 1M Aqueous sodium hydroxide solution (1.5 ml, 1.5 mmol) was added to a stirred solution of the title compound of Preparation 24 (220 mg, 0.51 mmol) in a mixture of 1,4-dioxan (3 ml) and methanol (10 ml). The resulting mixture was heated under reflux for 45 minutes, diluted with water and acidified with concentrated hydrochloric acid, then the precipitate collected and dried under vacuum to furnish the title compound (200 mg) as a colourless, crystalline solid, m.p. 180–182° C. Found: C, 65.64; H, 6.42; N, 3.30. C$_{23}$H$_{27}$NO$_4$S; 0.50 H$_2$O requires C, 65.38; H, 6.68; N, 3.32%. $\delta$(DMSO$_{d6}$): 0.83 (t,3H), 1.27 (m,4H), 1.81 (m,1H), 1.93 (m,1H), 2.58 (m,2H), 3.50 (m,2H), 4.00 (m,2H), 4.05 (dd,1H), 6.22 (brs, 1H), 7.33 (m,1H), 7.43 (m,2H), 7.52 (m,2H), 7.64 (m,4H), 13.30 (brs,1H).

LRMS (Thermospray): 387 (M+NH$_4$—CO$_2$)$^+$.

PREPARATION 26

Methyl 4-methyl-2(R,S)-[4-(4-phenylphenyl)-1-1,2,3,6-tetrahydropyridin-1-ylsulphonyl]pent4-enoate Obtained as a solid (79%), m.p. 149–151 ° C. after crystallisation from diisopropyl ether, from the title compound of Preparation 8 and 3-bromo-2-methylprop-1-ene, using the procedure of Preparation 14. $\delta$(CDCl$_3$): 1.77 (s,3H), 2.60–2.75 (m,3H), 2.80 (dd,1H), 3.57 (m,1H), 3.70 (m,1H), 3.78 (s,3H), 4.10 (m,2H), 4.18 (dd,1H), 4.75 (s,1H), 4.82 (s,1H), 6.10 (brs,1H), 7.35 (m,1H), 7.44 (m,4H), 7.60 (m,4H).

LRMS (Thermospray): 426 (M+H)$^+$.

PREPARATION 27

4-Methyl-2(R,S)-[4-(4-phenylphenyl)-1,2,3,6-tetrahydropyridin-1-ylsulphonyl]pent-4enoic acid Obtained as a colourless solid (94%), m.p. 153–155° C., from the title compound of Preparation 26, using the procedure of Preparation 15. $\delta$(CDCl$_3$): 1.79 (s,3H), 2.65 (m,2H), 2.75 (dd,1H), 2.90 (dd,1H), 3.60 (m,1H), 3.70 (m,1H), 4.13 (m,2H), 4.20 (dd,1H), 4.80 (s,1H), 4.88 (s,1H), 6.08 (s,1H), 7.35 (m,1H), 7.44 (m,4H), 7.60 (m,4H).

LRMS (Thermospray): 368 (M+H—CO$_2$)$^+$.

PREPARATION 28

Methyl 2(R,S)-methyl-2-[4-(3-methyl-4-phenylphenyl)-1,2,3,6-tetrahydropyridine-1-ylsulphonyl]pent-4-enoate 60% Sodium hydride in a mineral oil dispersion (70 mg, 1.75 mmol) was added to a stirred solution of the title compound of Preparation 9 (600 mg, 1.56 mmol) in anhydrous dimethylformamide (5 ml), under nitrogen, at room temperature. After 20 minutes, allyl bromide (0.145 ml, 1.72 mmol) was added and stirring continued for 2 hours, then more 60% sodium hydride dispersion (70 mg, 1.75 mmol) was added followed, after 20 minutes, by methyl iodide (0.11 ml, 1.72 mmol). The reaction mixture was stirred for a further 20 hours, then partitioned between ethyl acetate and water. The organic phase was separated, dried (MgSO$_4$) and evaporated under reduced pressure, then the residue purified by flash chromatography, using hexane:ethyl acetate (92.5:7.5) as eluant, to afford the title compound (263 mg) as a colourless gum. $\delta$(CDCl$_3$): 1.62 (s,3H), 2.30 (s,3H), 2.59 (m,1H), 2.66 (m,2H), 3.14 (m,1H), 3.62 (m,2H), 3.80 (s,3H), 4.10 (m,2H), 5.20 (m,2H), 5.62 (m,1H), 6.08 (brs, 1H), 7.20–7.44 (m,8H).

LRMS (Thermospray): 440 (M+H)$^+$.

PREPARATION 29

2(R,S)-Methyl-2-[4-(3-methyl-4-phenylphenyl)-1,2,3,6-tetrahydropyridin-1-ylsulphonyl]pent4-enoic acid Obtained as a colourless gum (90%) from the title compound of Preparation 28, using the procedure of Preparation 15, but with a reaction duration of 24 hours. $\delta$(CDCl$_3$): 1.63 (s,3H), 2.30.(s,3H), 2.62 (m,3H), 3.13 (m,1H), 3.68 (m,2H), 4.18 (m,2H), 5.22 (m,2H), 5.70 (m,1H), 6.07 (brs,1H), 7.17–7.45 (m,8H).

LRMS (Thermospray): 382 (M+H—CO$_2$)$^+$, 426 (M+H)$^+$.

PREPARATION 30

1-Benzhydryl-3-(4-phenylphenoxy)azetidine

Potassium carbonate (2.39 g, 17.4 mmol) was added to a stirred mixture of 1-benzhydryl-3-methanesulphonyloxyazetidine (J.Org.Chem., 1972, 37, 3953; 5 g, 15.8 mmol), 4-phenylphenol (2.95 g, 17.4 mmol)

and anhydrous dimethylformamide (65 ml), then the resulting mixture heated under reflux for 4 hours, allowed to cool and partitioned between ethyl acetate and water. The organic phase was separated, washed with saturated brine, dried (MgSO$_4$) and evaporated under reduced pressure, then the residue purified by flash chromatography, using hexane-:ethyl acetate (95:5) as eluant, to give the title compound (1.32 g) as a colourless, amorphous solid. δ(CDCl$_3$): 3.17 (dd,2H), 3.75 (dd,2H), 4.43 (s,2H), 4.83 (m,1H), 6.81 (d,1H), 7.16–7.55 (m,17H).

LRMS (Thermospray): 392 (M+H)$^+$.

PREPARATION 31

3-(4-Phenylphenoxy)azetidine

A stirred mixture of the title compound of Preparation 30 (1.03 g, 2.63 mmol), 10% palladium hydroxide on activated carbon (100 mg), ethanol (100 ml), ethyl acetate (20 ml) and glacial acetic acid (10 ml) was hydrogenated at 345 kPa (50 psi) and 50° C. for 20 hours, then filtered. The filter pad was washed with ethanol and the combined washings and filtrate evaporated under reduced pressure, then the residue was basified with 2M aqueous sodium hydroxide solution. This mixture was extracted with ethyl acetate and the combined extracts dried (MgSO$_4$) and evaporated under reduced pressure to yield the title compound containing 1 mol.equiv. of diphenylmethane* (456 mg) as a colourless, amorphous solid. δ(CDCl$_3$): 1.75 (brs,1H), 3.83 (m,2H), 3.94 (m,2H), 3.98 (s,2H)*, 6.82 (d,2H), 7.20–7.55 (m,17H)*.

LRMS (Thermospray): 226 (M+H)$^+$.

PREPARATION 32

Methyl 2-[3-(4-phenylphenoxy)azetidin-1l-ylsulphonyl]acetate

Obtained as a colourless, amorphous solid (22%) from the title compound of Preparation 31 and methyl chlorosulphonylacetate, using the procedure of Preparation 8. δ(CDCl$_3$): 3.81 (s,3H), 4.07 (s,2H), 4.23 (dd,2H), 4.42 (dd,2H), 4.98 (m,1H), 6.80 (d,2H), 7.34 (m,1H), 7.42 (m,2H), 7.54 (m,4H).

LRMS (APCI): 362 (M+H)$^+$.

PREPARATION 33 t-Butyl 4-(4-bromo-3-methylphenyl)-4-hydroxypiperidine-1-carboxylate

A. A 2.5M solution of n-butyllithium in hexane (3.8 ml, 9.4 mmol) was added over about 10 minutes to a stirred mixture of 2,5-dibromotoluene (2.35 g, 9.4 mmol) in anhydrous ether (50 ml), under nitrogen, at about −75° C. After a further 1 hour, a solution of t-butyl 4-oxopiperidine-1-carboxylate (1.7 g, 8.5 mmol) in anhydrous tetrahydrofuran (5 ml) was added at such a rate that the reaction temperature was maintained below −60° C.

The reaction mixture was stirred at about −75° C. for 1 hour, allowed to warm to about 0° C. and quenched with aqueous ammonium chloride solution. The organic phase was separated, washed with water, dried (MgSO$_4$) and evaporated under reduced pressure. The residue was purified by flash chromatography, using ether:hexane (50:50) as eluant, to provide two isomeric products.

The less polar isomer (0.6 g, 20%) was isolated as a colourless foam and identified as t-butyl 4-(4-bromo-2-methylphenyl)4-hydroxypiperidine-1-carboxylate. δ(CDCl$_3$): 1.46 (s,9H), 1.55 (s,1H), 1.82–2.03 (m,4H), 2.58 (s,3H), 3.23 (m,2H), 4.01 (m,2H), 7.20–7.33 (m,3H).

LRMS (Thermospray): 369/371 (M+H)$^+$.

The more polar isomer, was collected as a 4:1 mixture of the title compound:t-butyl 4-oxopiperidine-1-carboxylate (2.15 g), a portion of which was crystallised from diisopropyl ether to furnish the pure title compound (570 mg) as a colourless solid, m.p. 102–103° C. Found: C, 55.14; H, 6.58; N,3.76. C$_{17}$H$_{24}$BrNO$_3$ requires C, 55.14; H, 6.53; N, 3.78%. δ(CDCl$_3$): 1.48 (s,9H), 1.51 (s,1H), 1.70 (d,2H), 1.96 (m,2H), 2.40 (s,3H), 3.22 (t,2H), 4.02 (m,2H), 7.15 (dd,1H), 7.36 (d,1H), 7.50 (d,1H).

LRMS (Thermospray): 369/371 (M+H)$^+$.

B. A 2.5M solution of n-butyllithium in hexane (38 ml, 94 mmol) was added over about 10 minutes to a stirred mixture of 2-bromo-5-iodo-toluene (28 g, 94 mmol) in anhydrous ether (500 ml), under nitrogen, at about −75° C. After a further 15 minutes, a solution of t-butyl 4-oxopiperidine-1-carboxylate (17 g, 85 mmol) in anhydrous tetrahydrofuran (50 ml) was added at such a rate that the reaction temperature was maintained below −60° C.

The reaction mixture was stirred at about −75° C. for 1 hour, allowed to warm to 0° C. and quenched with aqueous ammonium chloride solution. The organic phase was separated, washed with water, dried (MgSO$_4$) and evaporated under reduced pressure. The residue was dissolved in pentane and the resulting solution cooled to 0° C., when the title compound crystallised. It was collected and dried to afford a colourless solid (20.1 g, 64%), identical with that obtained in Preparation 33A.

PREPARATION 34 t-Butyl 4-(4-bromophenyl)-4-hydroxypiperidine-1-carboxylate

Obtained as an amorphous solid (74%) from 1,4-dibromobenzene and t-butyl 4-oxopiperidine-1-carboxylate, using the procedure of Preparation 33. δ(CDCl$_3$): 1.50 (s,9H), 1.69 (m,2H), 1.95 (m,2H), 3.22 (t,2H), 4.02 (m,2H), 7.34 (d,2H), 7.47 (d,2H).

LRMS (Thermospray): 357 (M+H)$^+$.

PREPARATION 35

4-(4-Bromo-3-methylphenyl)-1,2,3,6-tetrahydropyridine

Trifluoroacetic acid (100 ml) was added to a stirred solution of the title compound of Preparation 33 (20 g) in dichloromethane (100 ml) at room temperature. After a further 18 hours, the reaction mixture was evaporated under reduced pressure and the residue basified with 2M aqueous sodium hydroxide solution to pH>12. The resulting mixture was extracted with ether, then the combined extracts washed with water, dried (MgSO$_4$) and evaporated under reduced pressure to give the title compound (13.6 g) as a low melting solid. δ(CDCl$_3$): 1.60 (brs,1H), 2.40 (m,5H), 3.10 (t,2H), 3.52 (m,2H), 6.10 (brs,1H), 7.05 (dd,1H), 7.22 (d,1H), 7.46 (d,1H).

LRMS (Thermospray): 251/253 (M+H)$^+$.

PREPARATION 36

4-(4-Bromophenyl)-1,2,3,6-tetrahydropyridine

Obtained as a solid (87%), m.p. 76–78° C., from the title compound of Preparation 34 and trifluoroacetic acid, using the procedure of Preparation 35. δ(CDCl₃): 2.43 (m,2H), 3.12 (t,2H), 3.53 (m,2H), 6.13 (s,1H), 7.25 (d,2H), 7.44 (d,2H).

LRMS (Thermospray): 239 (M+H)⁺.

PREPARATION 37

Methyl 2-[4-(4-bromo-3-methylphenyl)-1,2,3,6-tetrahydropyridin-1-ylsulphonyl]acetate N,O-Bis(trimethylsilyl)acetamide (0.9 ml, 4.0 mmol) was added to a stirred solution of the title compound of Preparation 35 (2 g, 7.9 mmol) in anhydrous tetrahydrofuran (40 ml), under nitrogen, at room temperature. A solution of methyl chlorosulphonylacetate (1.64 g, 9.5 mmol) in anhydrous tetrahydrofuran (15 ml) was then added and the reaction mixture stirred at room temperature for 18 hours. The resulting mixture was evaporated under reduced pressure, the residue partitioned between ethyl acetate and aqueous sodium bicarbonate solution, then the organic phase separated, washed with water, dried (MgSO₄) and evaporated under reduced pressure. The residue was purified by flash chromatography, using dichloromethane as eluant, followed by crystallisation from diisopropyl ether, to yield the title compound (1.65 g, 55%) as a colourless solid, m.p. 110–112° C. Found: C, 46.32; H, 4.62; N,3.55. $C_{15}H_{18}BrNO_4S$ requires C, 46.40; H, 4.67; N, 3.61%. δ(CDCl₃): 2.40 (s,3H), 2.60. (m,2H), 3.60 (t,2H), 3.80 (s,3H), 4.01 (s,2H), 4.07 (m,2H), 6.02 (brs,1H), 7.02 (dd, 1H), 7.21.(d,1H), 7.50 (d,1H).

LRMS (Thermospray): 404/406. (M+NH₄)⁺.

PREPARATION 38

Methyl 2-[4-(4-bromophenyl)-1,2,3,6-tetrahydropyridin-1-ylsulphonyl]acetate

Obtained as a colourless solid (32%), m.p. 100–102° C., from the title compound of Preparation 36 and methyl chlorosulphonylacetate, using the procedure of Preparation 37. Found: C, 44.95; H, 4.26; N, 3.65. $C_{14}H_{16}BrNO_4S$ requires C, 44.93; H, 4.31; N, 3.74%. δ(DMSO$_{d6}$): 2.47 (m,2H), 3.46 (t,2H), 3.70 (s,3H), 3.94 (m,2H), 4.37 (s,2H), 6.03 (s,1 H), 7.40 (d,2H), 7.55 (d,2H).

LRMS (Thermospray): 393 (M+NH₄)⁺.

PREPARATION 39

Methyl 4-[4-(4-bromo-3-methylphenyl)-1,2,3,6-tetrahydropyridin-1-ylsulphonyl]-tetrahydropyran-4-carboxylate Bis-2-iodoethyl ether (3.9 g, 12 mmol) was added to a stirred mixture of the title compound of Preparation 37 (3.6 g, 9.3 mmol), anhydrous potassium carbonate (3.8 g, 27.8 mmol) and anhydrous dimethylsulfoxide (50 ml), under nitrogen, at room temperature. After 18 hours, the reaction mixture was partitioned between ether and water, then the organic phase washed with water, dried (MgSO₄) and evaporated under reduced pressure. The residue was purified by flash chromatography, using dichloromethane: methanol (99:1) as eluant, followed by crystallisation from diisopropyl ether, to provide the title compound (3.43 g, 80%) as a colourless solid, m.p. 128–130° C. Found: C, 49.92; H, 5.40; N, 2.90. $C_{19}H_{24}BrNO_5S$ requires C,49.78; H, 5.28; N, 3.06%. δ(CDCl₃): 2.23 (m,2H), 2.40 (s,3H), 2.42 (m,2H), 2.58 (m,2H), 3.30 (m,2H), 3.58 (m,2H), 3.87 (s,3H), 4.00–4.10 (m,4H), 6.00 (brs,1H), 7.02 (dd,1H), 7.21 (d,1H), 7.49 (d,1H).

LRMS (Thermospray): 477 (M+NH₄)⁺.

PREPARATION 40

Methyl 2-[4-(4-bromo-3-methylphenyl)-1,2,3,6-tetrahydropyridin-1-ylsulphonyl]-2-methylpropanoate Iodomethane (2 ml, 32.1 mmol) was added to a stirred mixture of the title compound of Preparation 37 (5 g, 12.9 mmol), anhydrous potassium carbonate (5.4 g, 39.1 mmol) and anhydrous dimethylsulfoxide (50 ml), under nitrogen, at room temperature. After 24 hours, the reaction mixture was partitioned between ether and water, then the organic phase washed with water, dried (MgSO₄) and evaporated under reduced pressure. The residue was purified by flash chromatography, using an elution gradient of ether:pentane (40:60 to 100:0), followed by crystallisation from diisopropyl ether, to furnish the title compound (4.7 g, 87%) as a colourless solid, m.p. 100–101° C. Found: C, 49.00; H, 5.33; N, 3.28. $C_{17}H_{22}BrNO_4S$ requires C, 49.04; H, 5.33; N,3.36%. δ(CDCl₃): 1.67 (s,6H), 2.40 (s,3H), 2.58 (m,2H), 3.60 (t,2H), 3.80 (s,3H), 4.08 (m,2H), 6.00 (brs,11H), 7.03 (dd,1H), 7.21 (d,1H), 7.49 (d,1H).

PREPARATION 41

Methyl 2-{4-[4-(3-ethoxyphenyl)-3-methylphenyl]-1,2,3,6-tetrahydropyridin-1-ylsulphonyl}acetate To a solution of the title compound of Preparation 37 (776 mg, 2 mmol) in degassed 1,2-dimethoxyethane (20 ml) was added 3-ethoxyphenylboronic acid (430 mg, 2.6 mmol), cesium fluoride (790 mg, 5.2 mmol), tri-o-tolylphosphine (61 mg, 0.2 mmol) and tris(dibenzylideneacetone) dipalladium(0) (91 mg, 0.1 mmol), then the reaction mixture heated under reflux for about 3 hours under nitrogen. The resulting mixture was allowed to cool to room temperature, then diluted with dichloromethane and washed with water. The organic phase was dried (MgSO₄) and evaporated under reduced pressure, then the residue purified by flash chromatography, using dichloromethane as eluant, followed by crystallisation from diisopropyl ether, to afford the title compound (665 mg, 78%) as a colouress solid, m.p. 79–81° C. Found: C, 64.40; H, 6.37; N, 3.17. $C_{23}H_{27}NO_5S$ requires C,64.31; H, 6.34; N, 3.26%. δ(CDCl₃): 1.43 (t,3H), 2.31 (s,3H), 2.70 (m,2H), 3.63 (t,2H), 3.82 (s,3H), 4.03 (s,2H), 4.10 (m,4H), 6.08 (brs,1H), 6.84–6.93 (m,3H), 7.20–7.37 (m,4H).

LRMS (Thermospray): 447 (M+NH₄)⁺.

PREPARATION 42

4-Bromo-2-methoxylbiphenyl n-Amyl nitrite (8.1 ml, 60 mmol) was slowly added to a stirred mixture of 4-bromo-2-methoxyaniline (J.Med.Chem., 1989, 32, 1936; 8.1 g, 60 mmol) and benzene (175 ml), under nitrogen, at about 50° C. When the addition was complete, the reaction mixture was heated under reflux for about 3 hours, then allowed to cool to room temperature and evaporated under reduced pressure. The residue was azeotroped with tetrahydrofuran, then with ethyl acetate, and purified by flash chromatography, using an elution gradient of hexane:ethyl acetate (100:0 to 95:5) to give the title compound (1.66 g) as a colourless solid, m.p. 50–52° C. δ(CDCl₃): 3.77 (s,3H), 7.08 (s,1H), 7.14 (s,2H), 7.30 (m,1H), 7.36–7.41 (m,2H), 7.41–7.49 (m,2H).

PREPARATION 43 t-Butyl 4-hydroxy-4-(3-methoxy-4-phenylphenyl) piperidine-1-carboxylate

A 2.5M solution of n-butyllithium in hexane (4.4 ml, 11 mmol) was added over about 10 minutes to a stirred mixture of the title compound of Preparation 42 (2.6 g, 10 mmol) in anhydrous tetrahydrofuran (30 ml), under nitrogen, at about −75° C. After a further 1 hour, a solution of t-butyl 4-oxopiperidine-1-carboxylate (2.2 g, 11 mmol) in anhydrous tetrahydrofuran (10 ml) was added at such a rate that the reaction temperature was maintained below −60° C., The reaction mixture was stirred at about −75° C. for 1 hour, then slowly warmed to room temperature and quenched with aqueous sodium chloride solution. The organic phase was separated, washed with water, dried ($MgSO_4$) and evaporated under reduced pressure. Purification of the residue by flash chromatography, using hexane:ethyl acetate (3:1) as eluant, yielded the title compound (3.4 g) as a colourless semi-solid. $\delta(CDCl_3)$: 1.50 (s,9H), 1.78 (m,2H), 2.04 (m,2H), 3.27 (m,2H), 3.83 (s,3H), 4.08 (m,2H), 7.09 (d,1H), 7.16 (s,1H), 7.27–7.37 (m,2H), 7.40 (m,2H), 7.52 (d, 2H).

PREPARATION 44

4-(3-Methoxy-4-phenylphenyl)-1,2,3,6-tetrahydropyridine

Trifluoroacetic acid (20 ml) was added to a stirred solution of the title compound of Preparation 43 (3.4 g, 11.9 mmol) in dichloromethane (20 ml) at room temperature. After a further 72 hours, the reaction mixture was evaporated under reduced pressure and the residue basified with 1M aqueous sodium hydroxide solution. The resulting mixture was extracted with dichloromethane, then the combined extracts washed with water, dried ($MgSO_4$) and evaporated under reduced pressure to provide the title compound (2.79 g) as a pale yellow viscous oil. $\delta(CDCl_3)$: 1.73.(s,1H), 2.51 (m,2H), 3.14 (t,2H), 3.57 (m,2H), 3.83 (s,3H), 6.19 (s,1H), 7.01 (s,1H), 7.05 (d,2H), 7.27–7.37 (m,2H), 7.40 (t,2H), 7.52 (d, 2H).

LRMS (Thermospray): 266 $(M+H)^+$.

PREPARATION 45

Methyl 2-[4-(3-methoxy-4-phenylphenyl)-1,2,3,6-tetrahydropyridin-1-ylsulphonyl]acetate N,O-Bis(trimethylsilyl)acetamide (1.0 ml, 4.4 mmol) was added dropwise to a stirred solution of the title compound of Preparation 44 (1.95 g, 7.3,mmol) in anhydrous tetrahydrofuran (40 ml) at room temperature. The reaction mixture was stirred at room temperature for 1 hour, then a solution of methyl chlorosulphonylacetate (1.5 g, 8.8 mmol) in tetrahydrofuran (10 ml) was added. The resulting mixture was stirred at room temperature for about 1.5 hours and then saturated aqueous sodium bicarbonate solution (50 ml) added. The mixture was extracted with dichloromethane (3×100 ml), then the combined extracts dried ($MgSO_4$) and evaporated under reduced pressure. The residue was purified by flash chromatography, using dichloromethane as eluant, to furnish the title compound (1.0 g) as a pale yellow solid solid, m.p. 92–95° C. Found: C, 62.24; H, 5.70; N, 3.42. $C_{21}H_{23}NO_5S$ requires C, 62.82; H, 5.77; N, 3.49%. $\delta(CDCl_3)$: 2.73 (m,2H), 3.67 (t,2H), 3.84 (s,3H), 3.86 (s,3H), 4.06 (s,2H), 4.08 (m,2H), 6.12 (s,1H), 6.98 (s,1H), 7.04 (d,2H), 7.27–7.37 (m,2H), 7.44 (t,2H), 7.56 (d,2H).

LRMS (Thermospray): 402 $(M)^+$.

PREPARATION 46 t-Butyl 4-(3-fluoro-4-phenylphenyl)-4-hydroxypiperidine-1-carboxylate

Obtained as a colourless oil (67%), from 4-bromo-3-fluorobiphenyl and t-butyl 4-oxopiperidine1-carboxylate, using the procedure of Preparation 43. $\delta(CDCl_3)$: ): 1.50 (s,9H), 1.78 (m,2H), 2.03 (m,2H), 3.26 (t,2H), 4.05 (m,2H), 7.27–7.51 (m,6H), 7.57 (d, 2H).

PREPARATION 47

4-(3-Fluoro-4-phenylphenyl)-1,2,3,6-tetrahydropyridine

Obtained as a colourless solid (90%), m.p. 79–82° C., from the title compound of Preparation 46 and trifluoroacetic acid, using the procedure of Preparation 44. $\delta(CDCl_3)$: 1.85 (s,1H), 2.49 (m,2H), 3.13 (t,2H), 3.58 (m,2H), 6.24 (brs, 1H), 7.12–7.27 (m,2H), 7.35–7.52 (m,4H), 7.59 (d,2H).

LRMS (Thermospray): 253 $(M)^+$.

PREPARATION 48

Methyl 2-[4-(3-fluoro-4-phenylphenyl)-1,2,3,6-tetrahydropyridin-1-ylsulphonyl]acetate Obtained as a colourless solid (38%), from the title compound of Preparation 47 and methyl chlorosulphonylacetate, using the procedure of Preparation 45. $\delta(DMSO_{d6})$: 2.60 (m,2H), 3.47 (t,2H), 3.68 (s,3H), 3.96 (s,2H), 4.37 (s,2H), 6.33 (brs,1H), 7.34–7.57 (m,8H).

LRMS (Thermospray): 407 $(M+NH_4)^+$.

PREPARATION 49

Methyl 2-[4-(3-methoxy-4-phenylphenyl)-1,2,3,6-tetrahydropyridin-1-ylsulphonyl]-2-methylpropanoate Iodomethane (0.2 ml, 3.4 mmol) was added to a stirred mixture of the title compound of Preparation 45 (0.54 g, 1.4 mmol), anhydrous potassium carbonate (0.56 g, 4.1 mmol) and anhydrous dimethylsulphoxide (5 ml), then the reaction mixture stirred at room temperature for about 16 hours. The resulting mixture was partitioned between ethyl acetate and water, then the organic phase washed with water, dried ($MgSO_4$) and evaporated under reduced pressure to afford the title compound (540 mg) as a pale yellow oil. $\delta(CDCl_3)$: 1.69 (s,6H), 2.67 (m,2H), 3.64 (t,2H), 3.82 (s,3H), 3.84 (s,3H), 4.14 (m,2H), 6.09 (s,1H), 6.98 (s,1H), 7.03 (d,2H), 7.27–7.37 (m,2H), 7.42 (t,2H), 7.54 (d,2H).

LRMS (Thermospray): 430 $(M+H)^+$.

PREPARATION 50

2-[4-(3-Methoxy-4-phenylphenyl)-1,2,3,6-tetrahydropyridin-1-ylsulphonyl]-2-methylpropanoic acid 1M Aqueous sodium hydroxide solution (1.2 ml, 1.2 mmol) was added to a stirred solution of the title compound of Preparation 49 (250 mg, 0.58 mmol) in methanol (5 ml). The resulting solution was heated at 50° C. for about 2 hours, then allowed to cool to room temperature and poured into ethyl acetate. This mixture was washed with 2M hydrochloric acid, then the organic phase dried ($MgSO_4$) and evaporated under reduced pressure to give the title compound (210 mg) as a pale yellow, semi-solid. $\delta(CDCl_3)$: 1.69 (s,6H), 2.67 (m,2H), 3.64 (t,2H), 3.83 (s,3H), 4.17 (m,2H), 6.08 (s,1H), 6.97 (s,1H), 7.03 (d,2H), 7.27–7.36 (m,2H), 7.40 (t,2H), 7.53 (d,2H).

LRMS (Thermospray): 433 $(M+NH_4)^+$.

PREPARATION 51

4-Bromo-2-methoxyphenyldiazonium tetrafluoroborate

A solution of 4-bromo-2-methoxyaniline (J. Med.Chem., 1989, 32, 1936; 17.9 g, 88.6 mmol) in anhydrous ether (350 ml) was added over about 1 hour to boron trifluoride etherate (27 ml, 212 mmol) at −15° C. The resulting solution was stirred at −15° C. for about 5 minutes and then a solution of t-butyl nitrite (11.4 ml, 106 mmol) in anhydrous ether (100 ml) was added slowly, keeping the internal temperature at around −15° C. The reaction mixture was stirred at −15° C. for a further 15 minutes and then at 4° C. for about 4 hours. Pentane was added and the resulting precipitate collected, washed with pentane and dried under reduced pressure to yield the title compound (20.1 g) as a purple solid. δ(CD$_3$CN): 4.20 (s,3H), 7.58 (d,1H), 7.80 (s,1H), 8.16 (d,1H).

LRMS (Thermospray): 301 (M)$^+$.

PREPARATION 52

4-(3-Ethoxyphenyl)-3-methoxybromobenzene

Anhydrous 1,4-dioxan (80 ml) was added to a mixture of the title compound Preparation 51 (8.0 g, 26.6 mmol), 3-ethoxyphenylboronic acid (5.3 g, 31.9 mmol) and palladium(II) acetate (0.35 g, 1.3 mmol) and the reaction mixture stirred at room temperature for about 16 hours. The resulting mixture was diluted with water (100 ml) and ether (100 ml), filtered and the filtrate extracted with ether (2×100 ml). The combined extracts were dried (MgSO$_4$) and then evaporated under reduced pressure. Purification of the residue by flash chromatography, using pentane:ether (20:1) as eluant, provided the title compound (6.9 g) as a colourless oil. δ(CDCl$_3$): 1.45 (t,3H), 3.83 (s,3H), 4.10 (q,2H), 6.89 (d,1H), 7.06 (d,2H), 7.10–7.24 (m,3H), 7.27–7.38 (m,1H).

LRMS (APCI): 308 (M+H)$^+$.

PREPARATION 53 t-Butyl 4-[4-(3-ethoxyphenyl)-3-methoxyphenyl]-4-hydroxypiperidine-1-carboxylate Obtained as a colourless oil (60%), from the title compound of Preparation 52 and t-butyl 4-oxopiperidine-1-carboxylate, using the procedure of Preparation 43. δ(CDCl$_3$): 1.44 (t,3H), 1.50 (s,9H), 1.79 (m,2H), 2.03 (m,2H), 3.27 (t,2H), 3.83 (s,3H), 4.06 (m,4H), 6.86 (d,1H), 7.08 (m,3H), 7.15 (s, 1H), 7.31 (m,2H).

PREPARATION 54

4-[4-(3-Ethoxyphenyl)-3-methoxyphenyl]-1,2,3,6-tetrahydropyridine

Obtained as a pale yellow viscous oil (91%), from the title compound of Preparation 53 and trifluoroacetic acid, using the procedure of Preparation 44. δ(CDCl$_3$): 1.44 (t,3H), 2.53 (m,2H), 3.16 (t,2H), 3.58 (s,2H), 3.83 (s,3H), 4.07 (q,2H), 6.19 (brs,1H), 6.86 (d,1H), 7.00 (s,1H), 7.07 (m,3H), 7.31 (m,2H).

LRMS (Thermospray): 310 (M+H)$^+$.

PREPARATION 55

Methyl 2-{4-[4-(3-ethoxyphenyl)-3-methoxyphenyl]-1,2,3,6-tetrahydropyridin-1-ylsulphonyl}acetate Obtained as a yellow semi-solid (22%), from the title compound of Preparation 54 and methyl chlorosuphonylacetate, using the procedure of Preparation 45. δ(CDCl$_3$): 1.43 (t,3H), 2.69 (m,2H), 3.65 (t,2H), 3.81 (s,3H), 3.84 (s,3H), 4.04 (s,2H), 4.08 (m,4H), 6.10 (brs,1H), 6.87 (d,1H), 6.96 (s,1H), 7.02 (d,1H), 7.09 (m,2H), 7.31 (m,2H).

LRMS (Thermospray): 446 (M+H)$^+$.

PREPARATION 56

Methyl 2-{4-[4-(3-ethoxyphenyl)phenyl]-1,2,3,6-tetrahydropyridin-1-ylsulphonyl}acetate To a solution of the title compound of Preparation 38 (250 mg, 0.7 mmol) in 1,2-dimethoxyethane (8 ml) was added 3-ethoxyphenylboronic acid (168 mg, 1.0 mmol), cesium fluoride (226 mg, 1.5 mmol), tri-o-tolylphosphine (21 mg, 0.07 mmol) and tris(dibenzylideneacetone)dipalladium(0) (31 mg, 0.035 mmol), then the reaction mixture heated under reflux for about 4 hours under nitrogen. The resulting mixture was allowed to cool to room temperature, then diluted with ethyl acetate and washed with saturated aqueous sodium bicarbonate solution. The organic phase was dried (MgSO$_4$) and evaporated under reduced pressure, then the residue triturated with hexane-ether to furnish the title compound (222 mg) as a pale yellow solid, m.p. 120–122° C. Found: C,64.25; H, 6.01; N, 2.99. C$_{22}$H$_{25}$NO$_5$S requires C, 63.60; H,6.06; N, 3.37%. δ(DMSO$_{d6}$): 1.32 (t,3H), 2.62 (m,2H), 3.50 (t,2H), 3.71 (s,3H), 3.98.<d,2H), 4.10 (q,2H), 4.37 (s,2H), 6.27 (brs,1H), 6.91 (d,1H), 7.18 (s,1H), 7.22 (d,1H), 7.36 (t,1H), 7.52 (d,2H), 7.66 (d,2H).

LRMS (Thermospray): 433 (M+NH$_4$)$^+$.

PREPARATION 57

4-Bromo-2-methylphenyidiazonium tetrafluoroborate

Obtained as a yellow solid (93%), from 4-bromo-2-methylaniline and t-butyl nitrite, using the procedure of Preparation 51. δ(CD$_3$CN): 2.70 (s,3H), 7.93 (d,1H), 8.04 (s,1H), 8.50 (d,1H).

PREPARATION 58

4-(3-Methoxyphenyl)-3-methylbromobenzene

Obtained as a pale yellow oil (25%), from the title compound of Preparation 57 and 3-methoxyphenylboronic acid, using the procedure of Preparation 52. δ(CDCl$_3$): 2.15 (s,3H), 3.84 (s,3H), 6.79–6.94 (m,3H), 7.09 (s,1H), 7.33 (d,1H), 7.37 (d,1H), 7.43 (s,1H).

PREPARATION 59 t-Butyl 4-hydroxy-4-[4-(3-methoxyphenyl)-3-methylphenyl]piperidine-1-carboxylate Obtained as a colourless oil (63%), from the title compound of Preparation 58 and t-butyl 4-oxopiperidine-1-carboxylate, using the procedure of Preparation 43. δ(CDCl$_3$): 1.50 (s,9H), 1.79 (m,2H), 2.04 (m,2H), 2.19 (s,3H), 3.27 (t,2H), 3.83 (s,3H), 4.06 (m,2H), 6.85 (s,1H), 6.90 (d,2H), 7.26 (m, 1H), 7.34 (t,2H), 7.38 (s,1H).

LRMS (Thermospray): 399 (M+H)$^+$.

PREPARATION 60

4-[4-(3-Methoxyphenyl)-3-methylphenyl]-1,2,3,6-tetrahydropyridine

Obtained as a pale yellow semi-solid (93%), from the title compound of Preparation 59 and trifluoroacetic acid, using the procedure of Preparation 44. δ(CDCl$_3$), 2.30 (s,3H), 2.42 (s,2H), 3.15 (t,2H), 3.57 (s,2H), 3.83 (s,3H), 6.18 (brs,1H), 6.90 (m,3H), 7.16–7.36 (m, 4H).

LRMS (Thermospray): 280 (M+H)$^+$.

PREPARATION 61

Methyl 2-{4-[4-(3-methoxyphenyl)-3-methylphenyl]-1,2,3,6-tetrahydropyridin-1-ylsulphonyl}acetate A solution of methyl chlorosulphonylacetate (0.65 g, 3.7 mmol) in dichloromethane (10 ml) was added dropwise to a stirred solution of the title compound of Preparation 60 (0.92 g, 3.3 mmol) and 1,8-diazabicyclo[5.4.0]undec-7-ene (0.76 g, 4.9 mmol) in dichloromethane (20 ml) at about 0° C., the cooling bath removed and the reaction mixture stirred at room temperature for 4 hours, then diluted with dichloromethane. The resulting mixture was washed with 0.1 M hydrochloric acid, dried ($MgSO_4$) and evaporated under reduced pressure, then the residue purified by flash chromatography, using dichloromethane as eluant, to afford the title compound (250 mg) as a colourless solid, m.p. 83–85° C. $\delta(CDCl_3)$: 2.30 (s,3H), 2.69 (m,2H), 3.66 (t,2H), 3.85 (s,3H), 3.86 (s,3H), 4.03 (s,2H), 4.11 (m,2H), 6.09 (brs,1H), 6.83–6.97(m,3H), 7.17–7.35 (m, 4H).

LRMS (Thermospray): 416 $(M+H)^+$.

PREPARATION 62

3-Ethylphenylboronic acid n-Butyllithium (11 ml of a 2.5M solution in hexane, 28 mmol) was added to a stirred solution of 3ethylbromobenzene (Chem. Pharm. Bull., 1968, 16, 2456; 4.6 g, 25 mmol) in anhydrous tetrahydrofuran (50 ml), whilst keeping the internal temperature below −60° C. The mixture was stirred at about −70° C. for 1 hour, then trimethylborate (4.4 ml, 38 mmol) added dropwise, again whilst keeping the internal temperature below −60° C. The reaction mixture was stirred at −70° C. for 30 minutes, then slowly allowed to warm to room temperature. 2M Hydrochloric acid was added, the mixture was extracted with dichloromethane (3×50 ml) and the combined extracts concentrated under reduced pressure The residue was dissolved in ether (50 ml), the solution extracted with 1M aqueous sodium hydroxide solution (2×30 ml) and the aqueous phase acidified with 2M hydrochloric acid, then extracted with ether (3×50 ml). The combined extracts were dried ($MgSO_4$) and evaporated under reduced pressure to give the title compound as a white solid (0.9 g, 24%). $\delta(DMSO_{d6})$: 1.17 (t,3H), 2.57 (q,2H), 7.22 (t,2H), 7.57 (t,1H), 7.61 (s,1H), 7.93 (s,2H).

PREPARATION 63

Methyl 2-{4-[4-(3-ethylphenyl)-3-methylphenyl]-1,2,3,6-tetrahydropyridin-1-ylsulphonyl}acetate Obtained as a yellow solid (75%), m.p. 58–60° C., from the title compounds of Preparation 62 and Preparation 37, using the procedure of Preparation 41. $\delta(CDCl_3)$: 1.27 (t,3H), 2.50 (s,3H), 2.68 (m,4H), 3.64 (t,2H), 3.82 (s,3H), 4.03 (s,2H), 4.10 (s,2H), 6.08 (brs,1H), 7.14–7.37 (m,7H).

LRMS (Thermospray): 431 $(M+NH_4)^+$.

PREPARATION 64

Methyl 4-{4-[4-(3-methoxyphenyl)-3-methylphenyl]-1,2,3,6-tetrahydropyridin-1-ylsulphonyl}tetrahydropyran-4-carboxylate Obtained as a glassy solid (20%), from the title compound of Preparation 61 and bis-2-iodoethyl ether, using the procedure of Preparation 39. $\delta(CDCl_3)$: 2.20–2.34 (m,5H), 2.45 (m,2H), 2.67 (m,2H), 3.33 (t,2H), 3.62 (m,2H), 3.83 (s,3H), 3.89 (s,3H), 4.01 (m,2H), 4.10 (m,2H), 6.05 (brs,1H), 6.91 (m,3H), 7.23–7.36 (m,4H).

LRMS (APCI): 486 $(M+H)^+$.

PREPARATION 65

4-{4-[4-(3-Methoxyphenyl)-3-methylphenyl]-1,2,3,6-tetrahydropyridin-1-ylsulphonyl}tetrahydropyran-4-carboxylic acid Obtained as a pale yellow solid (93%), m.p. 180–190° C., from the title compound of Preparation 64, using the procedure of Preparation 50. $\delta(CDCl_3)$: 2.20–2.33 (m,5H), 2.43 (m,2H), 2.65 (m,2H), 3.43 (t,2H), 3.67 (m,2H), 3.82 (s,3H), 4.04 (m,2H), 4.14 (m,2H), 6.04 (brs,1H), 6.88 (m,3H), 7.21–7.36 (m,4H).

PREPARATION 66

Methyl 4-{4-[4-(3-methoxyphenyl)-3-methylphenyl]piperidin-1-ylsulphonyl}-tetrahydropyran-4-carboxylate A stirred mixture of the title compound of Preparation 64 (315 mg, 0.65 mmol), ammonium formate (200 mg, 3.2 mmol), 10% palladium on carbon (50 mg) and methanol (5 ml) was heated under reflux for 1.5 hours, then allowed to cool and filtered. The filtrate was evaporated under reduced pressure and the residue partitioned between ether and water. The organic phase was dried ($MgSO_4$) and evaporated under reduced pressure, then the residue crystallised from methanol to yield the title compound (215 mg) as a white solid, m.p. 137–139° C. $\delta(CDCl_3)$: 1.75–1.94 (m,4H), 2.19 (d,1H), 2.22 (d,1H), 2.27 (s,3H), 2.43 (m,2H), 2.66 (m,1H), 3.07 (t,2H), 3.32 (t,2H), 3.83 (s,3H), 3.90 (s,3H), 3.96 (m,2H), 4.00 (d,1H), 4.02 (d,1H), 6.87 (m,3H), 7.08 (m,2H), 7.19 (d,1H), 7.32 (m,1H).

LRMS (APCI): 486 $(M+H)^+$.

PREPARATION 67

4-{-4-[4-(3-Methoxyphenyl)-3-methylphenyl]piperidin-1-ylsulphonyl}tetrahydropyran-4-carboxylic acid Obtained as a white solid (84%), m.p. 225–228° C., from the title compound of Preparation 66, using the procedure of Preparation 50, but with a mixture of methanol (5 ml) and tetrahydrofuran (10 ml) as solvent. Found: C, 63.04; H, 6.59; N, 2.91. $C_{25}H_{31}NO_6S$ requires C, 63.40; H, 6.60; N, 2.96%. $\delta(DMSO_{d6})$: 1.60 (m,2H), 1.80 (m,2H), 1.93 (dt,2H), 2.20 (s,3H), 2.24 (m,2H), 2.68 (m,1H), 3.05 (t,2H), 3.20 (t,2H), 3.75 (s,3H), 3.77 (m,2H), 3.88 (d,1H), 3.92 (d,1H), 6.86 (m,3H), 7.11 (m,3H), 7.31 (m,1H), 13.80 (brs,1H).

LRMS (APCI): 474 $(M)^+$.

PREPARATION 68

3-Methoxy-4-(3-methoxyphenyl)bromobenzene

Obtained as a pale yellow oil (78%), from the title compound of Preparation 51 and 3-methoxyphenylboronic acid, using the procedure of Preparation 52. Found: C, 57.77; H, 4.51. $C_{14}H_{13}BrO_2$ requires C, 57.36; H, 4.47. $\delta(CDCl_3)$: 3.82 (s,3H), 3.86 (s,3H), 6.91 (d,1H), 7.03–7.39 (m,6H).

LRMS (Thermospray): 311 $(M+NH_4)^+$.

PREPARATION 69 t-Butyl 4-hydroxy-4-[3-methoxy-4-(3-methoxyphenyl)phenyl]piperidine-1-carboxylate Obtained as a colourless oil (67%), from the title compound of Preparation 68 and t-butyl 4-oxopiperidine-1- carboxylate, using the procedure of Preparation 43. δ(CDCl$_3$): 1.50 (s,9H), 1.79 (m,2H), 2.06 (m,2H), 3.28 (t,2H), 3.83 (s,6H), 4.06 (m,2H), 6.88 (d,1H), 7.08 (m,3H), 7.14 (s, 1H), 7.32 (m,2H).

LRMS (Thermospray): 436 (M+Na)$^+$.

PREPARATION 70

4-[3-Methoxy-4-(3-methoxyphenyl)phenyl]-1,2,3,6-tetrahydropyridine

A stirred solution of the title compound of Preparation 69 (6.7 g, 16.2 mmol) and p-toluenesulphonic acid (6.17 g, 32.5 mmol) in toluene (70 ml) was heated under reflux in a Dean-Stark apparatus until water removal was complete (ca. 4 hours), then allowed to cool and diluted with ethyl acetate (100 ml). The resulting mixture was washed with 1M aqueous sodium hydroxide solution (3×50 ml), then the organic phase dried (MgSO$_4$) and evaporated under reduced pressure to provide the title compound (3.3 g) as a yellow oil. δ(CDCl$_3$): 1.80 (brs,1H), 2.50 (m,2H), 3.14 (t,2H), 3.57 (m,2H), 3.84 (s,6H), 6.20 (brs,1H), 6.88 (d,1H), 6.98–7.36 (m, 6H).

LRMS (Thermospray): 296 (M+H)$^+$.

PREPARATION 71

Methyl 2-{4-[3-methoxy-4-(3-methoxyphenyl)phenyl]-1,2,3,6-tetrahydropyridin-1-ylsulphonyl}acetate Obtained as a yellow semi-solid (40%), from the title compound of Preparation 70 and methyl chlorosulphonylacetate, using the procedure of Preparation 45. Found: C, 58.87; H, 5.65; N, 3.11. C$_{22}$H$_{25}$NO$_6$S; 1.00 H$_2$O requires C, 58.78; H, 6.05; N, 3.12%. δ(CDCl$_3$): 2.71 (m,2H), 3.64 (t,2H), 3.81 (s,3H), 3.84 (s,6H), 4.02 (s,2H), 4.11 (m,2H), 6.10 (brs,1H), 6.88 (d,1H), 6.97 (s,1H), 7.02 (d,1H), 7.12 (m,2H), 7.32 (m,2H).

LRMS (Thermospray): 449 (M+H)$^+$.

PREPARATION 72

Methyl 2-{4-[3-methoxy-4-(3-methoxyphenyl)phenyl]-1,2,3,6-tetrahydropyridin-1-ylsulphonyl}-2-methylpropanoate Obtained as a colourless semi-solid (40%), from the title compound of Preparation 71 and iodomethane, using the procedure of Preparation 49. Found: C, 62.30; H, 6.29; N, 3.00. C$_{24}$H$_{29}$NO$_6$S requires C, 62.73; H, 6.36; N, 3.05%. δ(CDCl$_3$): 1.68 (s,6H), 2.67 (m,2H), 3.64 (t,2H), 3.82 (s,3H), 3.84 (s,3H), 3.85 (s,3H), 4.13 (m,2H), 6.07 (brs,1H), 6.88 (d,1H), 6.97 (s,1H), 7.02 (d,1H), 7.13 (m,2H), 7.31 (m,2H).

LRMS (Thermospray): 460 (M+H)$^+$.

PREPARATION 73

Methyl 2-{4-[3-methoxy-4-(3-methoxyphenyl)phenyl]piperidin-1-ylsulphonyl}2-methylpropanoate Obtained as a colourless solid (80%), m.p. 140–142° C., from the title compound of Preparation 72, using the procedure of Preparation 66. Found: C, 62.31; H, 6.87; N, 2.91. C$_{24}$H$_{31}$NO$_6$S requires C, 62.45; H,.6.77; N, 3.03%. δ(CDCl$_3$): 1.66 (s,6H), 1.87 (m,4H), 2.49 (m,1H), 3.09 (t,2H), 3.82 (s,6H), 3.84 (s,3H), 3.93 (m,2H), 6.81 (s,1H), 6.86 (d,2H), 7.08 (m,2H), 7.29 (m,2H).

LRMS (Thermospray): 462 (M+H)$^+$.

PREPARATION 74

2-{4-[3-Methoxy4-(3-methoxyphenyl)phenyl]piperidin-1-ylsulphonyl}2-methylpropanoic acid Obtained as a colourless solid (80%), m.p. 164–165° C., from the title compound of Preparation 73, using the procedure of Preparation 50. Found: C, 61.64; H, 6.53; N, 3.06. C$_{23}$H$_{29}$NO$_6$S requires C, 61.73; H, 6.53; N, 3.13%. δ(CDCl$_3$): 1.69 (s,6H), 1.87 (m,4H), 2.69 (m,1H), 3.10 (t,2H), 3.81 (s,3H), 3.82 (s,3H), 4.02 (m,2H), 6.80 (s,1H), 6.87 (m,2H), 7.07 (m,2H), 7.27 (m,2H).

LRMS (Thermospray): 465 (M+NH$_4$)$^+$.

PREPARATION 75

Methyl 2-{4-[4-(3-ethoxyphenyl)-3-methoxyphenyl]-1,2,3,6-tetrahydropyridin-1-ylsulphonyl}-2-methylpropanoate Obtained as a pale yellow oil (29%), from the title compound of Preparation 55 and iodomethane, using the procedure of Preparation 49. Found: C, 62.99; H, 6.64; N, 2.88. C$_{25}$H$_{31}$NO$_6$S requires C, 63.40; H, 6.60; N, 2.96%. δ(CDCl$_3$): 1.43 (t,3H), 1.67 (s,6H), 2.66 (m,2H), 3.63 (t,2H), 3.81 (s,3H), 3.83 (s,3H), 4.07 (q,2H), 4.13 (m,2H), 6.07 (brs,1H), 6.87 (d,1H), 6.96 (s,1H), 7.02 (d,1H), 7.10 (m,2H), 7.31 (m,2H).

LRMS (Thermospray): 474 (M+H)$^+$.

PREPARATION 76

Methyl 2-{4-[4-(3-ethoxyphenyl)-3-methoxyphenyl]piperidin-1-ylsulphonyl}-2-methylpropanoate Obtained as a colourless semi-solid (83%) from the title compound of Preparation 75, using the procedure of Preparation 66. Found: C, 62.86; H, 7.12; N, 2.68. C$_{25}$H$_{33}$NO$_6$S requires C, 63.14; H, 6.99; N, 2.95%. δ(CDCl$_3$): 1.43 (t,3H), 1.67 (s,6H), 1.86 (m,4H), 2.70 (m,1H), 3.09 (t,2H), 3.82 (s,6H), 3.97 (m,2H), 4.06 (q,2H), 6.80 (s,1H), 6.86 (m,2H), 7.08 (m,2H), 7.27 (m,2H).

LRMS (Thermospray): 476 (M+H)$^+$.

PREPARATION 77

2-{4-[4-(3-Ethoxyphenyl)-3-methylphenyl]piperidin-1-ylsulphonyl}-2methyl-propanoic acid Obtained as a colourless solid (95%), from the title compound of Preparation 76, using the procedure of Preparation 50. Found: C, 61.92; H, 7.00; N, 2.72. C$_{24}$H$_{31}$NO$_6$S requires C, 62.45; H, 6.77; N, 3.03%. δ(CDCl$_3$): 1.42 (t,3H), 1.70 (s,6H), 1.87 (m,4H), 2.70 (m,1H), 3.11 (t,2H), 3.80 (s,3H), 4.04 (m,4H), 6.80 (s,1H), 6.85 (d,2H), 7.08 (m,2H), 7.27 (m,2H).

LRMS (Thermospray): 479 (M+NH$_4$)$^+$.

PREPARATION 78

Methyl 4-{4-[4-(3-ethoxyphenyl)-3-methylphenyl]-1,2,3,6-tetrahydropyridin-1-ylsulphonyl}tetrahydropyran-4-carboxylate Obtained as a colourless foam (86%), from the title compound of Preparation 39 and 3-ethoxyphenylboronic acid, using the procedure of Preparation 41, but with methanol:dichloromethane (1:99) as eluant. δ(CDCl$_3$): 1.42

(t,3H), 2.22 (m,2H), 2.28 (s,3H), 2.44 (d,2H), 2.65 (m,2H), 3.34 (dd,2H), 3.60 (m,2H), 3.90 (s,3H), 4.00–4.15 (m,6H), 6.03 (brs,1H), 6.83–6.92 (m,3H), 7.20–7.36 (m,4H).

LRMS (Thermospray): 500 (M+H)$^+$.

PREPARATION 79

4-{4-[4-(3-Ethoxyphenyl)-3-methylphenyl]-1,2,3,6-tetrahydropyridin-1-ylsulphonyl}tetrahydropyran-4-carboxylic acid 1M Aqueous sodium hydroxide solution (2.3 ml, 2.3 mmol) was added to a stirred solution of the title compound of Preparation 78 (290 mg, 0.58 mmol) in a mixture of methanol (10 ml) and 1,4-dioxan (2 ml). The resulting solution was heated at 80° C. for about 5 hours, then allowed to cool to room temperature and evaporated under reduced pressure. The residue was partitioned between 1M hydrochloric acid and ethyl acetate, then the organic phase dried (MgSO$_4$) and evaporated under reduced pressure. The residue was crystallised from diisopropyl ether to furnish the title compound (220 mg) as a colourless solid, m.p. 203–205° C. Found: C, 64.14; H, 6.47; N, 2.87. C$_{26}$H$_{31}$NO$_6$S requires C, 64.31; H, 6.44; N, 2.89%. δ(CDCl$_3$): 1.43 (t,3H), 2.27 (m,2H), 2.29 (s,3H), 2.42 (d,2H), 2.68 (m,2H), 3.42 (dd,2H), 3.67 (m,2H), 4.00–4.18 (m,6H), 6.04 (brs,1H), 6.82–6.93 (m,3H), 7.20–7.35 (m,4H).

LRMS (Thermospray): 486 (M+H)$^+$.

PREPARATION 80

Methyl 2-{4-[4-(3-ethoxyphenyl)-3-methylphenyl]-1,2,3,6-tetrahydropyridin-1-ylsulphonyl}-2-methylpropanoate Obtained as a colourless solid (80%), m.p. 75–76° C., from the title compound of Preparation 41 and iodomethane, using the procedure of Preparation 40. Found: C, 65.55; H, 6.82; N, 2.98. C$_{25}$H$_{31}$NO$_5$S requires C, 65.62; H, 6.83; N, 3.06%. δ(CDCl$_3$): 1.43 (t,3H), 1.68 (s,6H), 2.28 (s,3H), 2.65 (m,2H), 3.62 (m,2H), 3.81 (s,3H), 4.06 (q,2H), 4.12 (m,2H), 6.06 (brs,1H), 6.83–6.92 (m,3H), 7.20–7.35 (m,4H).

LRMS (Thermospray): 458 (M+H)$^+$.

PREPARATION 81

2-{4-[4-(3-Ethoxyphenyl)-3-methylphenyl]-1,2,3,6-tetrahydropyridin-1-ylsulphonyl}-2-methylpropanoic acid Obtained as a colourless amorphous solid (50%), from the title compound of Preparation 80, using the procedure of Preparation 79, but with purification by flash chromatography using methanol:dichloromethane (2:98). δ(CDCl$_3$): 1.43 (t,3H), 1.68 (s,6H), 2.25 (s,3H), 2.60 (m,2H), 3.62 (m,2H), 4.05 (q,2H), 4.15 (m,2H), 6.03 (brs,1H), 6.78–6.90 (m,3H), 7.20–7.35 (m,4H).

LRMS (APCI): 444 (M+H)$^+$.

PREPARATION 82

Methyl 2-{4-[4-(3-ethoxyphenyl)-3-methylphenyl]piperidin-1-ylsulphonyl}acetate

Obtained as a colourless amorphous solid (99%), from the title compound of Preparation 41, using the procedure of Preparation 66. δ(CDCl$_3$): 1.43 (t,3H), 1.85 (m,2H), 1.97 (m,2H), 2.28 (s,2H), 2.67 (m,1H), 3.01 (m,2H), 3.84 (s,3H), 3.98 (s,2H), 4.01 (m,2H), 4.05 (q,2H), 6.80–6.90 (m,3H), 7.05–7.34 (m,4H).

LRMS (Thermospray): 432 (M+H)$^+$.

PREPARATION 83

Methyl 2-{4-[4-(3-ethoxyphenyl)-3-methylphenyl]piperidin-1-ylsulphonyl}-2-methylpropanoate Obtained as a colourless gum (91%), from the title compound of Preparation 82 and iodomethane, using the procedure of Preparation40. δ(CDCl$_3$): 1.42 (t,3H), 1.67 (s,6H), 1.80–1.95 (m,4H), 2.29 (s,3H), 2.67 (m, 1H), 3.10 (m,2H), 3.82 (s,3H), 3.97 (m,2H), 4.06 (q,2H), 6.82–6.90 (m,3H), 7.06–7.35 (m,4H).

LRMS (Thermospray): 460 (M+H)$^+$.

PREPARATION 84

2-{4-[4-(3-Ethoxyphenyl)-3-methylphenyl]piperidin-1-ylsulphonyl}-2-methyl-propanoic acid Obtained as a colourless solid (72%), m.p. 125–128° C., from the title compound of Preparation 83, using the procedure of Preparation 79, except that the crude product was flash chromatographed using methanol: dichloromethane (3:97), before crystallisation from diisopropyl ether. Found: C, 64.14; H, 7.01; N, 3.06. C$_{24}$H$_{31}$NO$_5$S requires C, 64.69; H, 7.01; N, 3.14%. δ(CDCl$_3$): 1.41 (t,3H), 1.68 (s,6H), 1.77–1.97 (m,4H), 2.26 (s,3H), 2.66 (m,1H), 3.10 (m,2H), 4.00–4.10 (m,4H), 6.80–6.90 (m,3H), 7.03–7.35 (m,4H).

LRMS (APCI): 446 (M+H)$^+$.

PREPARATION 85

Methyl 2-{4-[3-methyl-4-(pyridin-2-yl)phenyl]-1,2,3,6-tetrahydropyridin-1-ylsulphonyl}acetate A stirred solution of the title compound of Preparation37 (206 mg, 0.53 mmol), 2-(tri-n-butylstannyl)pyridine (Tetrahedron, 1997 53, 859; 295 mg, 0.80 mmol), tri-o-tolylphosphine (50 mg, 0.16 mmol), palladium(II) acetate (12 mg, 0.05 mmol) and triethylamine (0.2 ml, 1.44 mmol) in anhydrous acetonitrile (6 ml), under nitrogen, was heated under reflux for 6 hours. Additional portions of tri-o-tolylphosphine (50 mg, 0.16 mmol) and palladium(II) acetate (12 mg, 0.05 mmol) were added, then reflux continued for a further 24 hours. The resulting, cool mixture was partitioned between ethyl acetate and aqueous sodium bicarbonate solution, then the separated organic phase washed with water, dried (MgSO$_4$) and evaporated under reduced pressure. The residue was purified by flash chromatography, using an elution gradient of hexane:ethyl acetate (100:0 to 55:45), to afford the title compound (20 mg, 10%) as a colourless amorphous solid. δ(CDCl$_3$): 2.39 (s,3H), 2.68 (m,2H), 3.65 (t,2H), 3.81 (s,3H), 4.02 (s,2H), 4.10 (m,2H), 6.10 (brs,1H), 7.23–7.30 (m,3H), 7.40 (m,2H), 7.75 (dd,1H), 8.70 (d,1H).

LRMS (APCI): 387 (M+H)$^+$.

PREPARATION 86

Methyl 2-{4-[3-methyl-4-(pyridin-3-yl)phenyl]-1,2,3,6-tetrahydropyridin-1-ylsulphonyl}acetate Obtained as a colourless foam (78%), from the title compound of Preparation 37 and 3-(tri-n-butylstannyl)pyridine, using the procedure of Preparation 85, except that the reaction time was 5 hours at reflux followed by 72 hours at room temperature. Found: C, 62.07; H, 5.78; N, 7.09. $C_{20}H_{22}N_2O_4S$ requires C, 62.16; H, 5.74; N, 7.25%. δ(CDCl$_3$): 2.30 (s,3H), 2.70 (m,2H), 3.68 (t,2H), 3.83 (s,3H), 4.03 (s,2H), 4.14 (m,2H), 6.10 (brs,1H), 7.20–7.40 (m,4H), 7.66 (d,1H), 8.60 (m,2H).

LRMS (APCI): 387 (M+H)$^+$.

PREPARATION 87

Methyl 2-{4-[3-methyl-4-(pyridin-4-yl)phenyl]-1,2,3,6-tetrahydropyridin-1-ylsulphonyl}acetate Obtained as a colourless foam (54%), from the title compound of Preparation 37 and 4-(tri-n-butylstannyl) pyridine, using the procedure of Preparation 85. Found: C, 61.98; H, 5.80; N, 7.13. $C_{20}H_{22}N_2O_4S$ requires C, 62.16; H, 5.74; N, 7.25%. δ(CDCl$_3$): 2.30 (s,3H), 2.70 (m,2H), 3.64 (t,2H), 3.81 (s,3H), 4.02 (s,2H), 4.10 (m,2H), 6.10 (brs,1H), 7.20–7.30 (m,5H), 8.66 (d,2H).

LRMS (APCI): 387 (M+H)$^+$.

PREPARATION 88

6-Ethoxy-2-(tri-n-butylstannyl)-pyridine

A 2.5M solution of n-butyllithium in hexane (4.5 ml, 11.3 mmol) was added to a stirred solution of 2-bromo-6-ethoxypyridine (Rec. Trav. chim., 1965, 84, 53; 2.1 g, 11.3 mmol) in anhydrous ether (25 ml), under nitrogen, at about −40° C. After about 20 minutes, tri-n-butyltin chloride (3.1 ml, 11.4 mmol) was slowly added and, after a further 15 minutes, the reaction mixture was allowed to warm to room temperature. The resulting mixture was quenched by the addition of aqueous ammonium chloride solution, then the organic phase separated, washed with water, dried (MgSO$_4$) and evaporated under reduced pressure. The residue was purified by flash chromatography, using an elution gradient of pentane:dichloromethane (100:0 to 80:20), to give the title compound (1.6 g, 34%) as a colourless oil. δ(CDCl$_3$): 0.90 (t,9H), 1.08 (t,6H), 1.30–1.42 (m,9H), 1.58 (m,6H), 4.40 (q,2H), 6.53 (d,1H), 6.97 (d,1H), 7.39 (dd,1H).

PREPARATION 89

Methyl 2-{4-[4-(6-ethoxypyridin-2-yl)-3-methylphenyl]-1,2,3,6-tetrahydropyridin-1-ylsulphonyl}-2-methylpropanoate A stirred mixture of the title compounds of Preparation 40 (500 mg, 1.2 mmol) and Preparation 88 (745 mg, 1.8 mmol), tri-o-tolylphosphine (109 mg, 0.36 mmol), palladium(II) acetate (30 mg, 0.13 mmol), tetrakis(triphenylphosphine) palladium(0) (30 mg, 0.025 mmol), triethylamine (0.45 ml, 3.2 mmol) and anhydrous acetonitrile (15 ml), under nitrogen, was heated under reflux for 18 hours. The cool mixture was partitioned between ethyl acetate and aqueous sodium bicarbonate solution, then the organic phase separated, washed with water, dried (MgSO$_4$) and evaporated under reduced pressure. The residue was purified by flash chromatography, using an elution gradient of pentane:ether (95:5 to 80:20), to yield the title compound (290 mg, 52%) as a colourless foam. δ(CDCl$_3$): 1.40 (t,3H), 1.68 (s,6H), 2.46 (s,3H), 2.66 (m,2H), 3.63 (m,2H), 3.81 (s,3H), 4.12 (m,2H), 4.40 (q,2H), 6.07 (brs,1H), 6.68 (d,1H), 6.98 (d,1H), 7.26 (m,2H), 7.40 (d,1H), 7.60 (dd,1H).

LRMS (APCI): 459 (M+H)$^+$.

PREPARATION 90

Methyl 2-{4-[4-(6-ethoxypyridin-2-yl)-3-methylphenyl]piperidin-1-ylsulphonyl}-2-methylpropanoate A stirred solution of the title compound of Preparation 89 (280 mg, 0.6 mmol) in methanol (12 ml) was hydrogenated at 345 kPa (50 psi) pressure over 10% palladium on carbon (50 mg) for 18 hours, then the resulting mixture filtered. The filtrate was evaporated under reduced pressure and the residue purified by flash chromatography, using an elution gradient of pentane:ether (90:10 to 70:30), to provide the title compound (70 mg, 25%) as a colourless foam. δ(CDCl$_3$): 1.40 (t,3H), 1.67 (s,6H), 1.82 (m,2H), 1.89 (m,2H), 2.43 (s,3H), 2.67 (m,1H), 3.08 (m,2H), 3.81 (s,3H), 3.95 (brd,2H), 4.38 (q,2H), 6.67 (d,1H), 6.96 (d,1H), 7.10 (m,2H), 7.38 (d,1H), 7.60 (dd,1H).

LRMS (APCI): 461 (M+H)$^+$.

PREPARATION 91

2-{4-[4-(6-Ethoxypyridin-2-yl)-3-methylphenyl] piperidin-1-ylsulphonyl}-2-methyl-propanoic acid A solution of the title compound of Preparation 91 (68 mg, 0.15 mmol) in a mixture of 1,4-dioxan (2 ml) and 1M aqueous sodium hydroxide solution (0.26 ml, 0.26 mmol) was stirred at room temperature for 18 hours. The resulting solution was diluted with water (20 ml), acidified with glacial acetic acid to pH ∼4 and extracted with ethyl acetate. The extract was dried (MgSO$_4$) and evaporated under reduced pressure to furnish the title compound (60 mg, 87%) as a colourless solid, m.p. 178–179° C. Found: C, 61.53; H, 6.81; N, 6.09. $C_{23}H_{30}N_2O_5S$ requires C, 61.86; H, 6.77; N, 6.27%. δ(CDCl$_3$): 1.39 (t,3H), 1.68 (s,6H), 1.82 (m,2H), 1.90 (m,2H), 2.43 (s,3H), 2.67 (m,1H), 3.10 (m,2H), 4.00 (brd,2H), 4.38 (q,2H), 6.65 (d,1H), 6.96 (d,1H), 7.10 (m,2H), 7.38 (d,1H), 7.60 (dd,1H).

PREPARATION 92

Methyl 4-[4-(4-phenylphenyl)-1,2,3,6-tetrahydropyridin-1-ylsulphonyl]tetrahydropyran-4-carboxylate Obtained as a colourless solid (67%), m.p. 203–206° C., from the title compound of Preparation 8 and bis-2-iodoethyl ether, using the procedure of Preparation 39. δ(CDCl$_3$): 2.25 (m,2H), 2.44 (d,2H), 2.66 (m,2H), 3.32 (t,2H), 3.61 (m,2H), 3.90 (s,3H), 4.01 (dd,2H), 4.10 (m,2H), 6.08 (brs,1H), 7.30–7.62 (m,9H).

LRMS (Thermospray): 442 (M+H)$^+$.

PREPARATION 93

4-[4-(4-Phenylphenyl)-1,2,3,6-tetrahydropyridin-1-ylsulphonyl]tetrahydropyran-4-carboxylic acid Obtained as a colourless solid (66%), m.p. 214° C., from the title compound of Preparation 92, using the procedure of Preparation 79. δ(CDCl$_3$): 2.27 (m,2H), 2.42 (d,2H), 2.66 (m,2H), 3.41 (t,2H), 3.62 (m,2H), 4.04 (dd,2H), 4.15 (m,2H), 6.08 (brs,1H), 7.30–7.48 (m,5H), 7.58 (m,4H).

LRMS (APCI): 427 (M+H)$^+$.

PREPARATION 94

Methyl 4-{4-[4-(4-ethoxyphenyl)-3-methylpheny]-1,2,3,6-tetrahydropyridin-1-ylsulphonyl}tetrahydropyran-4-carboxylate Obtained as a colourless solid (66%), 140–141° C., from the title compound of Preparation 39 and 4-ethoxyphenylboronic acid, using the procedure of Preparation 41, but with ethyl acetate:hexane (30:70) as eluant. Found: C, 64.59; H, 6.60; N, 2.74. $C_{27}H_{33}NO_6S$ requires C, 64.91; H, 6.66; N, 2.80%. δ( DMSO$_{d6}$): 1.34 (t,3H), 2.00 (m,2H), 2.22 (s,3H), 2.28 (d,2H), 2.55 (brs,2H), 3.19 (t,2H), 3.50 (brs,2H), 3.80 (s,3H), 3.90 (dd,2H), 3.99 (brs,2H), 4.06 (q,2H), 6.17 (brs,1H), 6.96 (d,2H), 7.14 (d,1H), 7.22 (d,2H), 7.28 (d,1H), 7.33 (s,1H).

LRMS (Thermospray): 500 (M+H)$^+$.

PREPARATION 95

4-{4-[4-(4-Ethoxyphenyl)-3-methylphenyl]-1,2,3,6-tetrahydropyridin-1-ylsulphonyl}tetrahydropyran-4-carboxylic acid Obtained as a colourless solid (56%), m.p. 212–214° C., from the title compound of Preparation 94, using the procedure of Preparation 79. δ(CDCl$_3$): 1.34 (t,3H), 1.98 (m,2H), 2.22 (s,3H), 2.24 (d,2H), 2.55 (brs,2H), 3.19 (t,2H), 3.52 (brs,2H), 3.90 (dd,2H), 4.01 (brs,2H), 4.04 (q,2H), 6.17 (brs,1H), 6.96 (d,2H), 7.13 (d,1H), 7.22 (d,2H), 7.28 (d,1H), 7.33 (s,1H).

LRMS (Thermospray): 486 (M+H)$^+$.

PREPARATION 96

Methyl 2-{4-[4-(3-formylphenyl)-3-methylphenyl]-1,2,3,6-tetrahydropyridin-1-ylsulphonyl}acetate Obtained as a colourless gum (86%), from the title compound of Preparation 37 and 3-formylphenylboronic acid, using the procedure of Preparation 41, but with methanol:dichloromethane (1:99) as eluant. δ(CDCl$_3$): 2.30 (s,3H), 2.70 (m,2H), 3.64 (t,2H), 3.82 (s,3H), 4.02 (s,2H), 4.12 (m,2H), 6.10 (brs,1H), 7.20–7.33 (m,3H), 7.60 (m,2H), 7.85 (m,2H), 10.08 (s,1H).

LRMS (APCI): 414 (M+H)$^+$.

PREPARATION 97

Methyl 2-{4-[4-(3-hydroxymethylphenyl)-3-methylphenyl]-1,2,3,6-tetrahydropyridin-1-ylsulphonyl}acetate The title compound of Preparation 96 (303 mg, 0.73 mmol) was dissolved in a mixture of methanol (15 ml) and 1,2-dimethoxyethane (5 ml), polymer-supported borohydride on Amberlite™ IRA-400 (360 mg, 0.91 mmol) added and the reaction mixture stirred for 3 hours at room temperature. The resin was removed by filtration and the filtrate evaporated under reduced pressure to afford the title compound as a colourless foam (270 mg, 90%). δ(CDCl$_3$): 2.30 (s,3H), 2.70 (m,2H), 3.64 (t,2H), 3.82 (s,3H), 4.02 (s,2H), 4.12 (m,2H), 4.77 (brs,2H), 6.10 (brs,1H), 7.20–7.50 (m,7H).

LRMS (Thermospray): 416 (M+H)$^+$.

PREPARATION 98

Quinolin-3-ylboronic Acid

A 2.5M solution of n-butyllithium in hexane (4.4 ml, 11 mmol) was slowly added to a stirred solution of 3-bromoquinoline (2.08 g, 10 mmol) in anhydrous ether (20 ml), under nitrogen, at −75° C. After a further 20 minutes at −75° C., trimethylborate (1.46 ml, 13 mmol) was added, whereupon the red colour changed to yellow. The reaction mixture was allowed to warm to room temperature and quenched with water, followed by 1M aqueous sodium hydroxide solution (10 ml). The resulting mixture was stirred for 30 minutes and then glacial acetic acid added until a pH ~5–6 was attained, which generated a gummy precipitate. Diisopropyl ether was added to this mixture, stirring continued for 1 hour and then the clear aqueous and organic phases were decanted from the solid and discarded. The solid residue was dissolved in ethyl acetate and the solution washed with water, dried (MgSO$_4$) and evaporated under reduced pressure to give the title compound as a pale yellow solid (580 mg, 34%). Found: C, 62.74; H, 4.11; N, 7.92. C$_9$H$_8$BNO$_2$ requires C, 62.49; H, 4.66; N, 8.10%. δ(DMSO$_{d6}$): 7.59 (t,1H), 7.76 (t,1H), 7.98 (m,2H), 8.42 (brs,2H,exchangeable), 8.70 (s,1H), 9.18 (s,1H).

PREPARATION 99

Methyl 2-methyl-2-{4-[3-methyl-4-(quinolin-3-yl)phenyl]-1,2,3,6-tetrahydropyridin-1-ylsulphonyl}propanoate Obtained as a colourless solid (82%), m.p. 149–151° C., from the title compounds of Preparation 40 and Preparation 98, using the procedure of Preparation 41, but using 25% 1-methylpyrrolidin-2-one in 1,2-dimethoxyethane as the reaction solvent and ether:pentane (80:20) as eluant for flash chromatography. Found: C, 67.02; H, 6.20; N, 5.78. C$_{26}$H$_{28}$N$_2$O$_4$S requires C, 67.22; H, 6.08; N, 6.03%. δ(CDCl$_3$): 1.67 (s,6H), 2.36 (s,3H), 2.67 (m,2H), 3.65 (m,2H), 3.82 (s,3H), 4.13 (m,2H), 6.10 (brs,1H), 7.32 (m,3H), 7.60 (t,1H), 7.75 (t,1H), 7.87 (d,1H), 8.10 (s,1H), 8.16 (d,1H), 8.93 (s,1H).

LRMS (Thermospray): 465 (M+H)$^+$.

PREPARATION 100

2-Methyl-2-{4-[3-methyl-4-(quinolin-3-yl)phenyl]-1,2,3,6-tetrahydropyridin-1-ylsulphonyl}propionic acid A solution of the title compound of Preparation 99 (500 mg, 1.08 mmol) in a mixture of 1,4-dioxan (5 ml), methanol (10 ml) and 1M aqueous sodium hydroxide solution (3.2 ml, 3.2 mmol) was stirred under reflux for 30 minutes. The resulting solution was allowed to cool, acidified with glacial acetic acid to pH ~4, diluted with water (15 ml) and the resulting mixture partially evaporated under reduced pressure until crystallisation occurred. The solid was collected and dried to yield the title compound (440 mg, 90%) as a colourless solid, m.p. 222–224° C. Found: C, 66.17; H, 5.77; N, 6.15. C$_{25}$H$_{26}$N$_2$O$_4$S requires C, 66.64 H, 65.82; N, 6.22%. δ( DMSO$_{d6}$): 1.51 (s,6H), 2.31 (s,3H), 2.59 (m,2H), 3.58 (m,2H), 4.08 (m,2H), 6.26 (brs,1H), 7.33–7.50 (m,3H), 7.65 (t,1H), 7.78 (t,1H), 8.05 (t,2H), 8.37 (s,1H), 8.90 (s,1H), 13.4 (brs,1H).

LRMS (APCI): 451 (M+H)$^+$.

PREPARATION 101

3-Methylthiophenylboronic Acid

A solution of 3-bromothioanisole (10.3 g, 50.9 mmol) in anhydrous tetrahydrofuran (15 ml) was added dropwise to a stirred mixture of magnesium turnings (1.86 g, 75 mmol) and a crystal of iodine under nitrogen. Once the reaction was initiated, the remainder of the solution was added at such a rate as to keep the reaction mixture under reflux. When the addition was complete, the mixture was stirred under reflux for a further 1 hour, allowed to cool to room temperature and then added to a solution of trimethyl borate (5.8 ml, 51 mmol) in anhydrous tetrahydrofuran (25 ml), whilst keeping the internal temperature at about −10° C. The reaction mixture was allowed to warm to about 0° C., stirred for 30 minutes and then quenched with 2M hydrochloric acid. The resulting mixture was extracted with ether, then the combined extracts extracted, in turn, with 2M aqueous sodium hydroxide solution. The combined aqueous extracts were acidified with concentrated hydrochloric acid and extracted with ether. The combined ether extracts were dried (MgSO$_4$) and evaporated under reduced pressure to provide the title compound (7.8 g, 100%) as a white solid. δ(DMSO$_{d6}$): 2.45 (s,3H), 7.27 (m,2H), 7.54 (m,1H), 7.67 (s,1H), 8.05 (brs, 2H),

PREPARATION 102

Methyl 2-{4-[3-methyl-4-(3-methylthiophenyl) phenyl]-1,2,3,6-tetrahydropyridin-1-ylsulphonyl}acetate Obtained as a colourless solid (83%), from the title compounds of Preparation 101 and Preparation 37, using the procedure of Preparation 41, but using dichloromethane-:hexane (3:1) as eluant. δ(CDCl$_3$): 2.28 (s,3H), 2.50 (s,3H), 2.68 (m,2H), 3.64 (t,2H), 3.81 (s,3H), 4.02 (s,2H), 4.10 (m,2H), 6.08 (brs,1H), 7.07 (d,1H), 7.20–7.36 (m, 6H).
LRMS (APCI): 432 (M+H)$^+$.

PREPARATION 103

3-Methoxymethylphenylboronic Acid

Obtained as a yellow solid (100%), from 1-bromo-3-methoxymethylbenzene (J. Amer. Chem. Soc., 1989, 111, 6311; Tetrahedron 1985, 41, 1435) and trimethyl borate$_1$ using the procedure of Preparation 101. δ(DMSO$_{d6}$): 3.27 (s,3H), 4.38 (s,2H), 7.31 (m,2H), 7.68 (m,2H), 7.98 (brs, 2H).

PREPARATION 104

Methyl 2-{4-[4-(3-methoxymethylphenyl)-3-methylphenyl]-1,2,3,6-tetrahydropyridin-1-ylsulphonyl}acetate Obtained as a colourless oil (35%), from the title compounds of Preparation 103 and Preparation 37, using the procedure of Preparation 41, but using ether:hexane (60:40) as eluant. δ(CDCl$_3$): 2.27 (s,3H), 2.68 (m,2H), 3.42 (s,3H), 3.64 (t,2H), 3.81 (s,3H), 4.02 (s,2H), 4.10 (m,2H), 4.51 (s,2H), 6.08 (brs,1H), 7.20–7.32 (m, 7H).
LRMS (Thermospray): 430 (M+H)$^+$.

PREPARATION 105

1-Bromo-3-(2-methoxyethoxy)benzene

Anhydrous potassium carbonate (4.2 g, 30.4 mmol) was added to a stirred solution of 3-bromophenol (5.0 g, 28.9 mmol) in anhydrous dimethylformamide (100 ml). After 5 minutes, 1-iodo-2-methoxyethane (Annalen, 1967, 710, 59; 5.9 g, 31.8 mmol) was added and the reaction mixture stirred at room temperature for about 16 hours. At this point the mixture was heated at about 50° C. for approximately 72 hours, before 1-chloro-2-methoxyethane (1.8 ml, 19.8 mmol) was added and heating continued for a further 24 hours. The resulting mixture was evaporated under reduced pressure and the residue partitioned between ethyl acetate and water. The layers were separated and the aqueous layer was further extracted with ethyl acetate. The combined organic phases were washed with saturated aqueous sodium chloride solution, dried (MgSO$_4$) and concentrated to a red oil, which was purified by flash chromatography using hexane:ethyl acetate (3:1) as eluant, to furnish the title compound as a colourless oil (1.7 g, 25%). δ(CDCl$_3$): 3.43 (s,3H), 3.74 (t,2H), 4.10 (t,2H), 6.87 (d,1H), 7.10 (m,3H).

PREPARATION 106

3-(2-Methoxyethoxy)phenylboronic Acid

Obtained as a colourless solid (74%), m.p. 101–103° C., from the title compound of Preparation 105 and trimethyl borate, using the procedure of Preparation 101. Found: C, 55.09; H, 6.70. C$_9$H$_{13}$BO$_4$ requires C, 55.15; H, 6.69%. δ(DMSO$_{d6}$): 3.30 (s,3H), 3.63 (t,2H), 4.06 (t,2H), 6.94 (dd,2 H), 7.22 (t,2 H), 7.32 (m,2H), 7.98 (brs,2H).
LRMS (Thermospray): 214 (M+NH$_4$)$^+$.

PREPARATION 107

Methyl 2-{4-[4-(3-[2-methoxyethoxy]phenyl)-3-methylphenyl]-1,2,3,6-tetrahydropyridin-1-ylsulphonyl}acetate Obtained as a colourless oil (59%), from the title compounds of Preparation 106 and Preparation 37, using the procedure of Preparation 41, but using ether:hexane (1:1) as eluant. δ(CDCl$_3$): 2.28 (s,3H), 2.67 (m,2H), 3.45 (s,3H), 3.63 (t,2H), 3.77 (t,2H), 3.80 (s,3H), 4.02 (s,2H), 4.09 (s,2H), 4.15 (s,2H), 6.07 (brs,1H), 6.90 (m,3H), 7.19–7.3 4 (m, 4H).

PREPARATION 108

2,3-Dihydrobenzofuran-5-ylboronic Acid

Obtained as a colourless solid (38%), m.p. >240° C.(decomp.), from 5-bromo-2,3-dihydrobenzofuran (Synthesis, 1988, 952) and trimethyl borate, using the procedure of Preparation 101. δ(DMSO$_{d6}$): 3.33 (t,2H), 4.48 (t,2H), 6.68 (d,1H), 7.56 (d,1H), 7.63 (s,1H), 7.70 (brs,2H).

PREPARATION 109

5-(4-Bromo-2-methylphenyl)-2,3-dihydrobenzofuran

The title compound of Preparation 108 (2.0 g, 12.2 mmol) was added portionwise over 5 minutes to a stirred mixture of the title compound of Preparation 57 (3.4 g, 12.0 mmol) and palladium(II) acetate (0.15 g, 0.6 mmol) in anhydrous methanol (30 ml) and the reaction mixture heated under reflux for 1.5 hours. The resulting mixture was allowed to cool to room temperature, filtered, then the filtrate diluted with water (100 ml) and extracted with ether (2×100 ml). The combined extracts were dried (MgSO$_4$) and evaporated under reduced pressure, then the residue purified by flash chromatography, using hexane as eluant, to afford the title compound (1.7 g) as a pale orange oil. δ(CDCl$_3$): 2.25 (s,3H), 3.25 (t,2H), 4.62 (t,2H), 6.83 (d,1H), 7.02 (d,1H), 7.09 (m,2H), 7.34 (d, 1H), 7.60 (s,1H).
LRMS (APCI): 289 (M)$^+$.

PREPARATION 110 t-Butyl 4-[4-(2,3-dihydrobenzofuran-5-yl)-3-methyphenyl]-4-hydroxypiperidine-1-carboxalate Obtained as a white solid (66%), from the title compound of Preparation 109 and t-butyl 4-oxopiperidine-1-carboxylate, using the procedure of Preparation 43.

δ(CDCl$_3$): 1.50 (s,9H), 1.78 (m,2H), 2.06 (m,2H), 2.29 (s,3H), 3.26 (m,4H), 4.05 (m,2H), 4.62 (t,2H), 6.82 (d,1H), 7.05 (d,1H), 7.15 (s,1H), 7.21 (d, 1H), 7.30 (m,1H), 7.36 (s,1H).

LRMS (Thermospray): 432 (M+Na)$^+$.

PREPARATION 111

4-[4-(2,3-Dihydrobenzofuran-5-yl)-3-methylphenyl]-1,2,3,6-tetrahydropyridine

Obtained as a colourless viscous oil (98%), from the title compound of Preparation 110 and trifluoroacetic acid, using the procedure of Preparation 44. δ(CDCl$_3$): 2.30 (s,3H), 2.49 (m,2H), 3.12 (t,2H), 3.26 (t,2H), 3.56 (s,2H), 4.62 (t,2H), 6.17 (brs,1H), 6.82 (d,1H), 7.07 (d,1H), 7.16(m,2H), 7.26 (m,2H).

LRMS (Thermospray): 292 (M+H)$^+$.

PREPARATION 112

Methyl 2-{4-[4-(2,3-dihydrobenzofuran-5-yl)-3-methylphenyl]-1,2,3,6-tetrahydropyridin-1-ylsulphonyl}acetate Obtained as a pale yellow, foamy solid (45%), m.p. 118–122° C., from the title compound of Preparation 111 and methyl chlorosulphonylacetate, using the procedure of Preparation 61. δ(CDCl$_3$): 2.30 (s,3H), 2.67 (m,2H), 3.24 (t,2H), 3.62 (t,2H), 3.79 (s,3H), 4.01 (s,2H), 4.06 (s,2H), 4.62 (t,2H), 6.08 (brs,1H), 6.82 (d,1H), 7.05 (d,1H), 7.26 (m,4H).

LRMS (Thermospray): 428 (M+H)$^+$.

PREPARATION 113

3-Methyl-4-(3-trifluoromethylphenyl)bromobenzene

Obtained as a colourless oil (66%), from the title compound of Preparation 57 and 3-trifluoromethylphenylboronic acid, using the procedure of Preparation 109. δ(CDCl$_3$): 2.23 (s,3H), 7.08 (d,1H), 7.40–7.64 (m, 6H).

PREPARATION 114 t-Butyl 4-hydroxy-4-[3-methyl-4-(3-trifluoromethylphenyl)phenyl]piperidine-1-carboxylate Obtained as a yellow oil (54%), from the title compound of Preparation 113 and t-butyl 4-oxopiperidine-1-carboxylate, using the procedure of Preparation 43, but with hexane:ethyl acetate (85:15) as eluant. δ(CDCl$_3$): 1.50 (s,9H), 1.77 (m,2H), 2.04 (m,2H), 2.27 (s,3H), 3.26(m,2H), 4.05 (m,2H), 7.04 (d,1H), 7.15 (s,1H), 7.37 (m,2H), 7.55 (m,4H).

LRMS (Thermospray): 436 (M+H)$^+$.

PREPARATION 115

4-[3-Methyl-4-(3-trifluoromethylphenyl)phenyl]-1,2,3,6-tetrahydropyridine

Obtained as a colourless oil (98%), from the title compound of Preparation 114 and trifluoroacetic acid, using the procedure of Preparation 44. Found: C, 70.90; H, 5.84; N, 4.38. C$_{19}$H$_{18}$P$_3$N; 0.25 H$_2$O requires C, 70.90: H, 5.79; N, 4.35%. δ(CDCl$_3$): 2.26 (s,3H), 2.49 (brs,2H), 3.12 (brs,2H), 3.56 (brs,2H), 6.20 (brs,1H), 7.18 (m,2H), 7.26 (m,2H), 7.55 (m,4H).

LRMS (APCI): 318 (M)$^+$.

PREPARATION 116

Methyl 2-{4-[3-methyl-4-(3-trifluoromethylphenyl)phenyl]-1,2,3,6-tetrahydropyridin-1-ylsulphonyl}acetate Obtained as a pale yellow foam (31%), from the title compound of Preparation 115 and methyl chlorosulphonylacetate, using the procedure of Preparation 61, but with dichloromethane:hexane (80:20) as eluant. Found: C, 56.38; H, 4.77; N, 2.96. C$_{22}$H$_{22}$F$_3$NO$_4$S; 0.25 CH$_2$Cl$_2$ requires C, 56.30; H, 4.78 N, 2.95%. δ(CDCl$_3$): 2.27 (s,3H), 2.70 (m,2H), 3.64 (t,2H), 3.82 (s,3H), 4.03 (s,2H), 4.11 (s,2H), 6.10 (brs,1H), 7.24 (m,3H), 7.55 (m,4H).

LRMS (APCI): 453 (M)$^+$.

PREPARATION 117 t-Butyl 4-hydroxy-4-(4-phenoxyphenyl)piperidine-1-carboxylate

Obtained as a white foam (54%), from 4-phenoxybromobenzene and t-butyl 4-oxopiperidine-1-carboxylate, using the procedure of Preparation 43, but with a mixture of anhydrous ether and anhydrous tetrahydrofuran as solvent and ether:hexane (60:40) as eluant. δ(CDCl$_3$): 1.50 (s,9H), 1.75 (m,2H), 1.99 (m,2H), 3.25 (m,2H), 4.04 (m,2H), 7.00 (m,4H), 7.12 (t,1H), 7.37 (t,2H), 1.99 (d,2H).

PREPARATION 118

4-(4-Phenoxyphenyl)piperidine

Triethylsilane (3.0 ml, 18.9 mmol) was added to a stirred solution of the title compound of Preparation 117 (775 mg, 2.1 mmol) in anhydrous dichloromethane (10 ml), the resulting solution was cooled to about 0° C. and then trifluoroacetic acid (10 ml) was slowly added. The reaction mixture was allowed to warm to room temperature and then stirred for about 1.5 hours. The resulting mixture was evaporated under reduced pressure, then the residue dissolved in methanol and this solution basified with 2M aqueous sodium hydroxide solution. The mixture was extracted with ethyl acetate and the combined extracts dried (MgSO$_4$) and evaporated under reduced pressure.

This residue was dissolved in glacial acetic acid (20 ml) and the solution hydrogenated over palladium on carbon (60 mg) at 345 kPa (50 psi) and room temperature for 2 hours. The mixture was filtered, the filtrate evaporated under reduced pressure and the residue dissolved in methanol. This solution was then basified with 2M aqueous sodium hydroxide solution, extracted with ethyl acetate and the combined extracts dried (Na$_2$SO$_4$) and evaporated under reduced pressure to give the title compound as a yellow oil (550 mg, 100%). δ(CDCl$_3$): 1.63 (m,2H), 1.84 (m,2H), 2.60 (m,1H), 2.74 (t,2H), 3.20 (m,2H), 6.95 (d,2H), 7.00 (d,2H), 7.07 (t,1H), 7.18 (d,2H), 7.33 (m,2H).

LRMS (Thermospray): 254 (M+H)$^+$.

PREPARATION 119

Methyl 2-[4-(4-phenoxyphenyl)piperidin-1-ylsulphonyl]acetate

Obtained as a colourless solid (38%), from the title compound of Preparation 118 and methyl chlorosulphonylacetate, using the procedure of Preparation 45. δ(CDCl$_3$): 1.80 (m,2H), 1.94 (m,2H), 2.64 (m,1H), 3.00 (t,2H), 3.83 (s,3H), 3.95 (m,4H), 6.95 (m,4H), 7.10 (t,1H), 7.16 (d,2H), 7.33 (m,2H), LRMS (Thermospray): 407 (M+NH$_4$)$^+$.

PREPARATION 120

Methyl 2-{4-[4-(3-[2-methoxyethoxy]phenyl)-3-methylphenyl]-1,2,3,6-tetrahydropyridin-1-ylsulphonyl}-2-methylpropionate Obtained as a pale yellow oil (97%), from the title compounds of Preparation 106 and Preparation 40, using the procedure of Preparation41, but with ethyl acetate:hexane (1:3) as eluant. $\delta(CDCl_3)$: 1.67 (s,6H), 2.28 (s,3H), 2.65 (m,2H), 3.45 (s,3H), 3.62 (m,2H), 3.76 (m,2H), 3.80 (s,3H), 4.13 (m,4H), 6.06 (brs,1H), 6.90 (m,3H), 7.19–7.35 (m,4H).

PREPARATION 121

Methyl 2-{4-[4-(3-[2-methoxyethoxy]phenyl)-3-methylphenyl]piperidin-1-ylsulphonyl}-2-methylpropanoate Obtained as a pale yellow oil (83%), from the title compound of Preparation 120, using the procedure of Preparation 90. $\delta(CDCl_3)$: 1.66 (s,6H), 1.78–1.88 (m,4H), 2.27 (s,3H), 2.68 (m,1H), 3.09 (m,2H), 3.45 (s,3H), 3.77 (t,2H), 3.81 (s,3H), 3.96 (d,2H), 4.15 (t,2H), 6.90 (m,3H), 7.10 (m,2H), 7.18 (d,1H), 7.30 (t,1H).

LRMS (Thermospray): 490 (M+H)$^+$.

PREPARATION 122

2-{4-[4-(3-[2-Methoxyethoxy]phenyl)-3-methylphenyl]piperidin-1-ylsulphonyl}-2-methylpropionic acid Obtained as a colourless solid (78%), m.p. 140–141° C., from the title compound of Preparation 121, using the procedure of Preparation 79. Found: C, 62.89; H, 7.06; N, 2.85. $C_{25}H_{33}NO_6S$ requires C, 63.14; H, 6.99; N, 2.95%. $\delta(CDCl_3)$: 1.68 (s,6H), 1.78–1.88 (m,4H), 2.27 (s,3H), 2.68 (m,1H), 3.11 (m,2H), 3.45 (s,3H), 3.77 (t,2H), 4.00 (d,2H), 4.15 (t,2H), 6.90 (m,3H), 7.10 (m,2H), 7.18 (d,1H), 7.30 (t,1H).

LRMS (Thermospray): 475 (M+H)$^+$.

PREPARATION 123

Methyl 4-methoxy-2(R,S)-[4-(3-methyl-4-phenylphenyl)-1,2,3,6-tetrahydropyridin-1-ylsulphonyl]butanoate 60% Sodium hydride dispersion in mineral oil (23 mg, 0.57 mmol) was added to a stirred solution of the title compound of Preparation 9 (200 mg, 0.52 mmol) in anhydrous 1-methylpyrrolidin-2-one (3 ml), under nitrogen, at room temperature. After 30 minutes, 1-iodo-2-methoxyethane (101 mg, 0.57 mmol) was added and stirring continued for a further 16 hours, then the resulting mixture was partitioned between ethyl acetate and water. The organic phase was separated, washed with brine, dried (MgSO$_4$) and evaporated under reduced pressure. The residue was purified by flash chromatography, using dichloromethane as eluant, followed by trituration with diisopropyl ether, to yield the title compound (148 mg) as a colourless solid, m.p. 95–96° C. $\delta(CDCl_3)$: 2.28 (s,3H), 2.39 (m,2H), 2.67 (m,2H), 3.30 (s,3H), 3.40 (m,1H), 3.54 (m,2H), 3.67 (m,1H), 3.80 (s,3H), 4.10 (brs,2H), 4.17 (dd,1H), 6.07 (brs, 1H), 7.22 (m,3H), 7.32 (m,3H), 7.41 (m,2H).

LRMS (APCI): 444 (M+H)$^+$.

PREPARATION 124

4-Methoxy-2(R,S)-[4-(3-methyl-4-phenylphenyl)-1,2,3,6-tetrahydropyridin-1-ylsulphonyl]butanoic acid 1M Aqueous sodium hydroxide solution (1.0 ml, 1.0 mmol) was added to a stirred solution of the title compound of Preparation 123 (148 mg, 0.33 mmol) in a mixture of methanol (5 ml) and 1,4-dioxan (2 ml). The resulting solution was heated at 80° C. for about 4 hours, then allowed to cool to room temperature and evaporated under reduced pressure. The residue was diluted with water, then the resulting mixture acidified with glacial acetic acid and extracted with ethyl acetate. The combined organic phases were dried (MgSO$_4$) and evaporated under reduced pressure to provide the title compound (145 mg) as a colourless solid, m.p. 108–109° C. $\delta(CDCl_3)$: 2.28 (s,3H), 2.39 (m,2H), 2.67 (m,2H), 3.36 (s,3H), 3.53–3.73 (m,5H), 4.12 (brs,2H), 4.20 (dd,1H), 6.07 (brs, 1H), 7.19–7.47 (m,8H).

LRMS (APCI): 429 (M+H)$^+$.

PREPARATION 125

Methyl 4-[4-(3-methyl-4-phenylphenyl)-1,2,3,6-tetrahydropyridin-1-ylsulphonyl]tetrahydropyran-4-carboxylate 60% Sodium hydride dispersion in mineral oil (34 mg, 0.86 mmol) was added to a stirred solution of the title compound of Preparation 9 (300 mg, 0.78 mmol) in anhydrous 1-methylpyrrolidin-2-one (3 ml), under nitrogen, at room temperature. After 30 minutes, bis-2-iodoethyl ether (380 mg, 0.78 mmol) was added and stirring continued for a further 4 hours, then more 60% sodium hydride dispersion in mineral oil (34 mg, 0.86 mmol) was added and the mixture stirred for a further 16 hours. The resulting mixture was partitioned between ethyl acetate and water, then the organic phase separated, washed with water, dried (MgSO$_4$) and evaporated under reduced pressure. The residue was purified by crystallisation from diisopropyl ether to furnish the title compound (188 mg) as a colourless solid, m.p. 117–119° C. Found: C, 65.70; H,6.44; N, 2.98. $C_{25}H_{29}NO_5S$ requires C, 65.91; H, 6.42; N,3.08%. $\delta(CDCl_3)$: 2.22 (m,2H), 2.29 (s,3H), 2.47 (m,2H), 2.64 (m,2H), 3.33 (t,2H), 3.60 (m,2H), 3.87 (s,3H), 4.00 (dd,2H), 4.10 (m,2H), 6.07 (brs,1H), 7.20–7.43 (m,8H).

LRMS (Thermospray): 456 (M+H)$^+$.

PREPARATION 126

4-[4-(3-Methyl-4-phenylphenyl)-1,2,3,6-tetrahydropyridin-1-ylsulphonyl]tetrahydropyran-4-carboxylic acid 1M Aqueous sodium hydroxide solution (1.4 ml, 1.4 mmol) was added to a stirred solution of the title compound of Preparation 125 (160 mg, 0.35 mmol) in a mixture of methanol (5 ml) and 1,4-dioxan (2 ml). The resulting solution was heated at 80° C. for 4 hours, then allowed to cool to room temperature, diluted with water and concentrated under reduced pressure. The resulting mixture was acidified with 1M hydrochloric acid and the precipitate thus obtained was collected, washed with water and dried to afford the title compound (135 mg) as a colourless solid, m.p. 211–213° C. Found: C,64.89; H, 6.14; N, 3.07. $C_{24}H_{27}NO_5S$ requires C, 65.28; H,6.14; N, 3.17%. $\delta(DMSO_{d6})$: 1.96 (m,2H), 2.03 (s,3H), 2.10 (m,2H), 2.53 (m,2H), 3.23 (t,2H), 3.54 (m,2H), 3.92 (dd,2H), 4.03 (m,2H), 6.18 (brs,1H), 7.16 (d,1H), 7.28–7.43 (m,7H), 13.7 (brs,1H).

LRMS (APCI): 442 (M+H)$^+$.

PREPARATION 127

4-[4-(3-Methoxyphenyl)-3-methylphenyl]piperidine

Obtained as a pink oil (74%), from the title compound of Preparation 59, using the procedure of Preparation 118.

δ(CDCl$_3$): 1.67 (m,2H), 1.88 (m,2H), 2.29 (s,3H), 2.63 (m,1H), 2.57 (t,2H), 3.22 (m,2H), 3.83 (s,3H), 6.89 (m,3H), 7.10 (m,2H), 7.18 (d,1H), 7.32 (t,1H).

LRMS (Thermospray): 282 (M+H)$^+$.

PREPARATION 128

Methyl 2-{4-[4-(3-methoxyphenyl)-3-methylphenyl]piperidin-1-ylsulphonyl}acetate

Obtained as a colourless solid (47%), m.p. 96–98° C., from the title compound of Preparation 127 and methyl chlorosulphonylacetate, using the procedure of Preparation 45. δ(CDCl$_3$): 1.83 (m,2H), 1.96 (m,2H), 2.28 (s,3H), 2.63 (m,1H), 3.02 (t,2H), 3.83 (s,6H), 4.01 (m,4H), 6.89 (m,3H), 7.10 (m,2H), 7.20 (d,1H), 7.34 (t,1H).

LRMS (Thermospray): 418 (M+H)$^+$.

PREPARATION 129

Methyl 2-{4-[4-(3-methoxyphenyl)-3-methylphenyl]piperidin-1-ylsulphonyl}indane-2-carboxylate 1,2-Di(bromomethyl)benzene (409 mg, 1.55 mmol) was added to a stirred mixture of the title compound of Preparation 128 (500 mg, 1.2 mmol) and anhydrous potassium carbonate (497 mg, 3.6 mmol) in anhydrous 1,2-dimethoxyethane (5 ml) and the resulting mixture stirred at room temperature for 17 hours. Little reaction had occurred, so the solvent was evaporated under reduced pressure and the residue dissolved in 1-methylpyrrolidin-2-one (5 ml) and the solution heated at 100° C. for 2 hours. This mixture was allowed to cool to room temperature, partitioned between ether and water, then the organic phase washed with water, dried (MgSO$_4$) and evaporated under reduced pressure to give a yellow oil. Purification by flash chromatography, using an elution gradient of pentane:ethyl acetate (10:1 to 3:1), yielded the title compound as a white crystalline solid (160 mg), m.p. 174–176° C. Found: C, 68.95; H, 6.48; N, 2.56. C$_{30}$H$_{33}$NO$_5$S requires C,69.34; H, 6.40; N, 2.70%. δ(CDCl$_3$): 1.74 (m,2H), 1.85 (m,2H), 2.27 (s,3H), 2.57 (m,1H), 2.89 (t,2H), 3.73–3.86 (m,4H), 3.83 (s,6H), 3.96 (m,2H), 6.87 (m,3H), 7.06 (m,2H), 7.18–7.33 (m,6H).

LRMS (Thermospray): 520 (M+H)$^+$.

PREPARATION 130

2-{4-[4-(3-Methoxyphenyl)-3-methylphenyl]piperidin-1-ylsulphonyl}indane-2-carboxylic acid Obtained as a colourless solid (83%), m.p. 204–206° C., from the title compound of Preparation 129, using the procedure of Preparation 79. Found: C, 68.17; H, 6.22; N, 2.74. C$_{29}$H$_{31}$NO$_5$S; 0.30 H$_2$O requires C, 68.16; H, 6.23; N, 2.74%. δ(DMSO$_{d6}$): 1.54 (m,2H), 1.76 (m,2H), 2.21 (s,3H), 2.57 (m,1H), 2.89 (t,2H), 3.55 (d,2H), 3.72 (d,2H), 3.77 (s,3H), 3.81 (m,2H), 6.87 (m,3H), 7.07 (m,3H), 7.19 (m,2H), 7.28 (m,3H), 13.65 (brs,1H).

LRMS (Thermospray): 520 (M+NH$_4$)$^+$.

PREPARATION 131

Methyl 1-{4-[4-(3-methoxyphenyl)-3-methylphenyl]piperidin-1-ylsulphonyl}cyclobutanecarboxylate 1,3-Diiodopropane (513 mg, 1.73 mmol) was added to a stirred mixture of the title compound of Preparation 128 (557 mg, 1.33 mmol), anhydrous potassium carbonate (553 mg, 4.0 mmol) and anhydrous 1,2-dimethoxyethane (8 ml), then the mixture was stirred at room temperature for 17 hours and at reflux for 72 hours. The resulting mixture was allowed to cool to room temperature and partitioned between ethyl acetate and water, then the organic phase dried (MgSO$_4$) and evaporated under reduced pressure to give a yellow oil. Purification by flash chromatography, using pentane:ethyl acetate (3:1) as eluant, provided the title compound (472 mg) as a white crystalline solid, m.p. 97–101° C. δ(CDCl$_3$): 1.75–2.02 (m,5H), 2.13 (m,1H), 2.28 (s,3H), 2.59–2.75 (m,3H), 2.90 (m,2H), 3.00 (t,2H), 3.82 (s,3H), 3.87 (s,3H), 3.93 (m,2H), 6.87 (m,3H), 7.06 (m,2H), 7.18 (d,1H), 7.32 (t,1H).

LRMS (Thermospray): 458 (M+H)$^+$.

PREPARATION 132

1-{4-[4-(3-Methoxyphenyl)-3-methylphenyl]piperidin-1-ylsulphonyl}cyclobutanecarboxylic acid Obtained as a colourless solid (100%), m.p. 155–160° C., from the title compound of Preparation 131, using the procedure of Preparation 79. δ(CDCl$_3$): 1.80 (m,2H), 1.91 (m,2H), 2.12 (m,2H), 2.27 (s,3H), 2.62 (m,1H), 2.74 (m,2H), 2.91 (m,2H), 3.04 (t,2H), 3.82 (s,3H), 3.99 (m,2H), 6.87 (m,3H), 7.06 (m,2H), 7.18 (d,1H), 7.32 (t,1H).

LRMS (Thermospray): 444 (M+H)$^+$.

PREPARATION 133

Methyl 4-{4-[4-(3-methoxyphenyl)-3-methylphenyl]piperidin-1-ylsulphonyl}-1-methylpiperidine-4-carboxylate The title compound of Preparation 128 (500 mg, 1.2 mmol) and anhydrous potassium carbonate (553 mg, 4.0 mmol), followed by anhydrous 1,2-dimethoxyethane (8 ml), were added to N-methyl-bis(2-chloroethyl)amine hydrochloride (231 mg, 1.2 mmol) and the mixture was heated under reflux for 48 hours. The resulting mixture was allowed to cool to room temperature, diluted with ethyl acetate, washed with 5% aqueous citric acid solution, dried (MgSO$_4$) and evaporated under reduced pressure to give a yellow oil. The residual oil was dissolved in ethyl acetate and the solution washed successively with aqueous sodium bicarbonate solution/aqueous sodium hydroxide solution (pH 12) and aqueous sodium chloride solution, then dried (MgSO$_4$) and evaporated under reduced pressure to furnish the title compound as a yellow gum (175 mg). δ(CDCl$_3$): 1.87 (m,6H), 2.20 (m,2H), 2.25 (s,3H), 2.27 (s,3H), 2.53 (m,2H), 2.66 (m,1H), 2.90 (m,2H), 3.07 (t,2H), 3.82 (s,3H), 3.88 (s,3H), 3.93 (m,2H), 6.88 (m,3H), 7.08 (m,2H), 7.20 (d,1H), 7.32 (t,1H).

LRMS (Thermospray): 501 (M+H)$^+$.

PREPARATION 134

4-{4-[4-(3-Methoxyphenyl)-3-methylphenyl]piperidin-1-ylsulphonyl}-1-methylpiperidine-4-carboxylic acid hydrochloride 1M Aqueous sodium hydroxide solution (1.4 ml, 1.4 mmol) was added to a stirred solution of the title compound of Preparation 133 (172 mg, 0.34 mmol) in a mixture of methanol (5 ml) and 1,4-dioxan (3 ml). The reaction solution was heated at 80° C. for 10 hours, then allowed to cool to room temperature and concentrated under reduced pressure. The resulting mixture was acidified with 1M hydrochloric acid, washed with dichloromethane and evaporated under reduced pressure, then the residue was washed with water to afford the title compound (143 mg) as a colourless solid. δ(CDCl$_3$): 1.67 (m,2H), 1.84 (m,2H), 2.20 (s,3H), 2.30 (m,2H), 2.62–2.90 (m,7H), 3.12 (t,2H), 3.48 (m,2H), 3.77 (brs,6H), 6.88 (m,3H), 7.10 (brs,2H), 7.18 (brs,1H), 7.32 (t,1H).

LRMS (Thermospray): 523 (M+HCl)$^+$.

PREPARATION 135

Methyl 3-phenyl-2(R,S)-[4-(4-phenylphenyl)-1,2,3,6-tetrahydropyridin-1-ylsulphonyl]propanoate 60% Sodium hydride dispersion in mineral oil (34 mg, 0.77 mmol) was added to a stirred solution of the title compound of Preparation 8 (288 mg, 0.77 mmol) in anhydrous dimethylformamide (5 ml), under nitrogen, at room temperature. After 30 minutes, benzyl bromide (0.1 ml, 0.82 mmol) was added and stirring continued for a further 16 hours, then the resulting mixture was partitioned between ethyl acetate and water The organic phase was separated and the aqueous phase washed with ethyl acetate. The combined organic solutions were washed sequentially with water and aqueous sodium chloride solution, dried (MgSO$_4$) and evaporated under reduced pressure. The resulting residue was triturated with diisopropyl ether to give the title compound (170 mg) as a colourless solid, m.p. 137–138° C. δ(CDCl$_3$): 2.68 (m,2H), 3.42 (m,2H), 3.59 (m,1H), 3.67 (s,3H), 3.72 (m,1H), 4.14 (brs,2H), 4.21 (dd,1H), 6.10 (brs,1H), 7.18–7.37 (m,6H), 7.44 (m,4H), 7.59 (m,4H).

LRMS (Thermospray): 462 (M+H)$^+$.

PREPARATION 136

3-Phenyl-2(R,S)-[4-(4-phenylphenyl)-1,2,3,6-tetrahydropyridin-1-ylsulphonyl]propanoic acid Obtained as a colourless solid (50%), m.p. 164–165° C., from the title compound of Preparation 135, using the procedure of Preparation 79. δ(CDCl$_3$): 2.68 (m,2H), 3.41 (m,2H), 3.60 (m,1H), 3.72 (m,1H), 4.14 (brs,2H), 4.24 (dd,1H), 6.08 (brs,1H), 7.20–7.37 (m,6H), 7.43 (m,4H), 7.59 (m,4H).

LRMS (APCI): 447 (M+H)$^+$.

PREPARATION 137

Methyl 2-[4-(4-phenylphenyl)-1,2,3,6-tetrahydropyridin-1-ylsulphonyl]indane-2-carboxylate 60% Sodium hydride dispersion in mineral oil (30 mg, 0.73 mmol) was added to a stirred solution of the title compound of Preparation 8 (250 mg, 0.67 mmol) in anhydrous dimethylformamide (5 ml), under nitrogen, at room temperature. After 30 minutes, 1,2-di(bromomethyl)benzene (267 mg, 1.0 mmol) was added and stirring continued for a further 16 hours. Next, an additional quantity of sodium hydride dispersion in mineral oil (30 mg, 0.73 mmol) was added and the reaction mixture stirred at room temperature for a further 2 hours. The resulting mixture was partitioned between ethyl acetate and water, the organic phase was separated and the aqueous phase was extracted with ethyl acetate. The combined organic solutions were washed successively with water and aqueous sodium chloride solution, dried (MgSO$_4$) and evaporated under reduced pressure, then the residue purified by flash chromatography, using pentane:ether (3:1) as eluant, followed by trituration with diisopropyl ether, to yield the title compound (154 mg) as a colourless solid, m.p. 186–188° C. δ(CDCl$_3$): 2.60 (m,2H), 3.56 (m,2H), 3.75–3.88 (m,4H), 3.82 (s,3H), 4.07 (brs,2H), 6.05 (brs,1H), 7.19–7.28 (m,4H), 7.34–7.45 (m,5H), 7.59 (m,4H).

LRMS (APCI): 474 (M+H)$^+$.

PREPARATION 138

2-[4-(4-Phenylphenyl)-1,2,3,6-tetrahydropyridin-1-ylsulphonyl]indane-2-carboxylic acid Obtained as a colourless solid (67%), from the title compound of Preparation 137, using the procedure of Preparation 50, except that the residue was triturated with diisopropyl ether. δ(CDCl$_3$): 2.60 (m,2H), 3.56–3.84 (m,6H), 4.07 (brs,2H), 6.05 (brs,1H), 7.19–7.60(m,13H).

PREPARATION 139

4-(3-Chloro-4-fluorophenyl)-3-methylbromobenzene

Obtained as a colourless oil (20%), from the title compound of Preparation 57 and 3-chloro-4-fluorophenylboronic acid, using the procedure of Preparation 109. δ(CDCl$_3$): 2.22 (s,3H), 7.04 (d,1H), 7.10–7.20 (m,2H), 7.28–7.39 (m,2H), 7.42 (s,1H).

PREPARATION 140 t-Butyl 4-[4-(3-chloro-4-fluorophenyl)-3-methylphenyl]-4-hydroxypiperidine-1-carboxylate Obtained as a colourless gum (39%), from the title compound of Preparation 139 and t-butyl 4-oxopiperidine-1-carboxylate, using the procedure of Preparation 43. Found: C, 65.96;H, 6.64; N, 3.36. C$_{23}$H$_{27}$ClFNO$_3$ requires C, 65.79; H, 6.48; N, 3.34%. δ(CDCl$_3$): 1.50 (s,9H), 1.76 (m,2H), 2.04 (m,2H), 2.28 (s,3H), 3.28 (t,2H), 4.07 (m,2H), 7.16–7.20 (m,3H), 7.30–7.40 (m,3H).

LRMS (APCI): 420 (M+H)$^+$.

PREPARATION 141

4-[4-(3-Chloro-4-fluorophenyl)-3-methylphenyl]-1,2,3,6-tetrahydropyridine

Obtained as a pale yellow oil (99%), from the title compound of Preparation 140 and trifluoroacetic acid, using the procedure of Preparation 35. δ(CDCl$_3$): 2.26 (s,3H), 2.50 (m,2H), 3.12 (t,2H), 3.56 (m,2H), 6.16 (brs,1H), 7.15 (m,3H), 7.27 (m,2H), 7.35 (d,1H).

LRMS (APCI): 302 (M+H)$^+$.

PREPARATION 142

Methyl 2-{4-[4-(3-chloro-4-fluorophenyl)-3-methylphenyl]-1,2,3,6-tetrahydropyridin-1-ylsulphonyl}acetate Obtained as a colourless solid (37%), m.p. 125–126° C., from the title compound of Preparation 141 and methyl chlorosulphonylacetate, using the procedure of Preparation 61. Found: C, 57.46;H, 4.83; N, 3.14. C$_{21}$H$_{21}$ClFNO$_4$S requires C, 57.60;H, 4.83; N, 3.20%. δ(CDCl$_3$): 2.28 (s,3H), 2.67 (m,2H), 3.62 (t,2H), 3.80 (s,3H), 4.01 (s,2H), 4.06 (s,2H), 6.08 (brs,1H), 7.17 (m,3H), 7.23 (m,2H), 7.36 (d,1H).

LRMS (Thermospray): 438 (M+H)$^+$.

PREPARATION 143

4-(1,3-Benzodioxol-5-yl)-3-methylbromobenzene

Obtained as a colourless oil (34%), from the title compound of Preparation 57 and 1,3-benzodioxol-5-ylboronic acid, using the procedure of Preparation 109. δ(CDCl$_3$): 2.22 (s,3H), 6.00 (s,2H), 6.70 (d,1H), 6.75 (s,1H), 6.85 (d,1H), 7.06 (d,1H), 7.33 (d,1H), 7.40 (s,1H).

PREPARATION 144 t-Butyl 4-[4-(1,3-benzodioxol-5-yl)-3-methylphenyl] 4-hydroxypiperidine-1-carboxylate Obtained as a colourless solid (39%), m.p. 135–138° C., from the title compound of Preparation 143 and t-butyl 4-oxopiperidine-1-carboxylate, using the procedure of Preparation 43. Found: C, 69.82;H, 7.15; N, 3.44. $C_{24}H_{29}NO_5$ requires C, 70.05; H, 7.10; N, 3.40%. δ(CDCl$_3$): 1.50 (s,9H), 1.76 (m,2H), 2.04 (m,2H), 2.29 (s,3H). 3.28 (t,2H), 4.04 (m,2H), 6.00 (s,2H), 6.76 (d,1H), 6.79 (s,1H), 6.87 (d,1H), 7.20 (d,1H), 7.30 (d,1H), 7.37 (s,1H).

LRMS (APCI): 412 (M+H)$^+$.

PREPARATION 145

4-[4-(1,3-Benzodioxol-5-yl)-3-methylphenyl]-1,2,3, 6-tetrahydropyridine

Obtained as a pale yellow solid (96%), m.p. 105–108° C., from the title compound of Preparation 144 and trifluoroacetic acid, using the procedure of Preparation 35. δ(CDCl$_3$): 2.28 (s,3H), 2.50 (m,2H), 3.12 (t,2H), 3.56 (m,2H), 6.00 (s,2H), 6.17 (brs,1H), 6.75–6.82 (m,2H), 6.87 (d,1H), 7.17 (d,1H), 7.22–7.30 (m,2H).

LRMS (APCI): 294 (M+H)$^+$.

PREPARATION 146

Methyl 2- {4-[4-(1,3-benzodioxol-5-yl)-3-methylphenyl]-1,2,3,6-tetrahydropyridin-1-ylsulphonyl}acetate Obtained as a colourless solid (57%), m.p. 133–134° C., from the title compound of Preparation 145 and methyl chlorosulphonylacetate, using the procedure of Preparation 61. Found: C, 61.15; H, 5.41; N, 3.15. $C_{22}H_{23}NO_6S$ requires C, 61.52;H, 5.40; N, 3.26%. δ(CDCl$_3$): 2.28 (s,3H), 2.67 (m,2H), 3.62 (t,2H), 3;80 (s,3H), 4.01 (s,2H), 4.06 (s,2H), 6.00 (s,2H), 6.08 (brs,1H), 6.78 (m,2H), 6.87 (d,1H), 7.20 (m,2H), 7.26 (m,1H).

LRMS (APCI): 430 (M+H)$^+$.

PREPARATION 147

4-(2-Fluorophenyl)-3-methylbromobenzene

Obtained as a colourless oil (33%), from the title compound of Preparation 57 and 3-fluorophenylboronic acid, using the procedure of Preparation 109. δ(CDCl$_3$): 2.20 (s,3H), 7.06–7.25 (m,4H), 7.30–7.40 (m,2H), 7.43 (s,1H).

PREPARATION 148 t-Butyl 4-[4-(2-fluorophenyl)-3-methylphenyl]4-hydroxypiperidine-1-carboxylate

Obtained as a pale yellow, amorphous solid (53%), from the title compound of Preparation 147 and t-butyl 4-oxopiperidine-1-carboxylate, using the procedure of Preparation 43. Found: C, 71.39;H, 7.37; N, 3.69. $C_{23}H_{28}FNO_3$ requires C, 71.67;H, 7.32; N, 3.63%. δ(CDCl$_3$): 1.50 (s,9H), 1.78 (d,2H), 2.04 (m,2H), 2.22 (s,3H). 3.28 (t,2H), 4.04 (m,2H), 7.12 (t,1H), 7.16–7.26 (m,3H), 7.35 (m,2H), 7.40 (s,1H).

LRMS (APCI): 386 (M+H)$^+$.

PREPARATION 149

4-[4-(2-Fluorophenyl)-3-methylphenyl]-1,2,3,6-tetrahydropyridine

Obtained as a pale yellow oil (93%), from the title compound of Preparation 148 and trifluoroacetic acid, using the procedure of Preparation 35. δ(CDCl$_3$): 1.80 (brs,1H), 2.21 (s,3H), 2.50 (m,2H), 3.12 (t,2H), 3.57 (m,2H), 6.19 (brs,1H), 7.10–7.38 (m,7H).

LRMS (APCI): 268 (M+H)$^+$.

PREPARATION 150

Methyl 2-{4-[4-(2-fluorophenyl)-3-methylphenyl]-1, 2,3,6-tetrahydropyridin-1-ylsulphonyl}acetate Obtained as a colourless solid (30%), m.p. 128–130° C., from the title compound of Preparation 149 and methyl chlorosulphonylacetate, using the procedure of Preparation 61. Found: C, 62.57;H, 5.71; N, 3.32. $C_{21}H_{22}FNO_4S$ requires C, 62.52;H, 5.50; N, 3.47%. δ(CDCl$_3$): 2.21 (s,3H), 2.69 (m,2H), 3.63 (t,2H), 3.81 (s,3H), 4.01 (s,2H), 4.10 (m,2H), 6.09 (brs,1H), 7.14 (t,1H), 7.17–7.30 (m,5H), 7.35 (m,1H).

LRMS (APCI): 404 (M+H)$^+$.

PREPARATION 151

Methyl 2-{4-[4-(3,4-dimethoxyphenyl)-3-methylphenyl]-1,2,3,6-tetrahydropyridin-1-ylsulphonyl}acetate Obtained as a colourless gum (76%), from the title compound of Preparation 37 and 3,4-dimethoxyphenylboronic acid, using the procedure of Preparation 41. Found: C, 61.71; H, 6.10; N, 2.91. $C_{23}H_{27}NO_6S$ requires C, 62.01; H, 6.11; N, 3.14%. δ(CDCl$_3$): 2.30 (s,3H), 2.67 (m,2H), 3.62 (t,2H), 3.82 (s,3H), 3.87 (s,3H), 3.92 (s,3H), 4.02 (s,2H), 4.10 (m,2H), 6.08 (brs,1H), 6.83–6.97 (m,3H), 7.20–7.30 (m,3H).

LRMS (APCI): 446 (M+H)$^+$.

PREPARATION 152

Methyl 2-{4-[4-(indan-5-yl)-3-methylphenyl]-1,2,3, 6-tetrahydropyridin-1-ylsulphonyl}acetate Obtained as a pale yellow solid (75%), from the title compound of Preparation 37 and indan-5-ylboronic acid (WO-A-97/32853), using the procedure of Preparation 41. δ(CDCl$_3$): 2.10 (m,2H), 2.30 (s,3H), 2.69 (m,2H), 2.98 (m,4H), 3.62 (t,2H), 3.82 (s,3H), 4.02 (s,2H), 4.10 (m,2H), 6.08 (brs,1H), 7.09 (d,1H), 7.18–7.35 (m,5H).

LRMS (Thermospray): 443 (M+NH$_4$)$^+$.

PREPARATION 153

Methyl 2-{4-[3-methyl4-(3-trifluoromethoxyphenyl) phenyl]-1,2,3,6-tetrahydropyridin-1-ylsulphonyl}acetate Obtained as an amorphous solid (28%), from the title compound of Preparation 37 and 3-trifluoromethoxyphenylboronic acid (WO-A-96/13500), using the procedure of Preparation 41. δ(CDCl$_3$): 2.30 (s,3H), 2.69 (m,2H), 3.64 (t,2H), 3.81 (s,3H), 4.02 (s,2H), 4.10 (m,2H), 6.10 (brs,1H), 7.15–7.30 (m,6H), 7.43 (t,1H).

LRMS (APCI): 471 (M+H)$^+$.

PREPARATION 154

4-Phenyl-3trifluoromethylbromobenzene

Obtained as an orange oil (37%), from 4-bromo-2-trifluoromethylaniline, using the procedure of Preparation 42. Found: C, 51.70;C, 2.61. $C_{13}H_8BrF_3$ requires C, 51.86;H, 2.68%. $\delta(CDCl_3)$: 7.19 (d,1H), 7.26 (m,2H), 7.38 (m,3H), 7.65 (d,₁H), 7.86 (s,1H).

PREPARATION 155 t-Butyl 4-hydroxy-4-(4-phenyl-3-trifluoromethylphenyl)piperidine-1-carboxylate Obtained as a colourless solid (53%), m.p. 153–155° C. (from hexane), from the title compound of Preparation 154 and t-butyl 4-oxopiperidine-1-carboxylate, using the procedure of Preparation 43. Found: C, 65.34;H, 6.22; N, 3.26. $C_{23}H_{26}F_3NO_3$ requires C, 65.55;H, 6.22; N, 3.32%. $\delta(CDCl_3)$: 1.50 (s,9H), 1.78 (d,2H), 2.04 (m,2H), 3.28 (t,2H), 4.10 (m,2H), 7.28–7.42 (m,6H), 7.66 (d,1H), 7.88 (s,1H).

LRMS (Thermospray): 422 (M+H)⁺.

PREPARATION 156

4-(4-Phenyl-3-trifluoromethylphenyl)-1,2,3,6-tetrahydropyridine

Obtained as a pale brown oil (90%), from the title compound of Preparation 155 and p-toluenesulphonic acid, using the procedure of Preparation 70. $\delta(CDCl_3)$: 2.50 (m,2H), 3.17 (t,2H), 3.58 (m,2H), 6.27 (brs,1H), 7.25–7.42 (m,6H), 7.56 (d,1H), 7.75 (s,1H).

LRMS (Thermospray): 304 (M+H)⁺.

PREPARATION 157

Methyl 2-[4-(4-phenyl-3-trifluoromethylphenyl)-1,2,3,6-tetrahydropyridin-1-ylsulphonyl]acetate Obtained as a pale yellow oil (59%), from the title compound of Preparation 156 and methyl chlorosulphonylacetate, using the procedure of Preparation 37. $\delta(CDCl_3)$: 2.71 (m,2H), 3.66 (t,2H), 3.82 (s,3H), 4.02 (s,2H), 4.12 (m,2H), 6.18 (brs,1H), 7.28–7.42 (m,6H), 7.55 (d,1H), 7.72 (s,1H).

LRMS (APCI): 440 (M+H)⁺.

PREPARATION 158

2,2-Dimethyl-1,3-benzodioxol-5-ylboronic acid

Obtained as a green solid (47%), m.p. 174–176° C., from 5-bromo-2,2-dimethyl-1,3-benzodioxole (GB-A-2187452) and trimethyl borate, using the procedure of Preparation 101. $\delta(DMSO_{d6})$: 1.60 (s,6H), 6.77 (d,₁H), 7.17 (s,1H), 7.28 (d,1H), 7.80 (s,2H).

PREPARATION 159

Methyl 2-{4-[4-(2,2-dimethyl-1,3-benzodioxol-5-yl)-3-methylphenyl]-1,2,3,6-tetrahydropyridin-1-ylsulphonyl}-2-methylpropanoate Obtained as a colourless, amorphous solid (33%), from the title compounds of Preparation 158 and Preparation 40, using the procedure of Preparation 41, but with ether:hexane (1:4) as eluant. $\delta(CDCl_3)$: 1.67 (s,6H), 1.73 (s,6H), 2.30 (s,3H), 2.65 (m,2H), 3.62 (t,2H), 3.80 (s,3H), 4.13 (m,2H), 6.05 (brs,1H), 6.70–6.78 (m,3H), 7.19–7.30 (m,3H).

LRMS (Thermospray): 486 (M+H)⁺.

PREPARATION 160

Methyl 2-{4-[4-(2,2-dimethyl-1,3-benzodioxol-5-yl)-3-methylphenyl]piperidin-1-ylsulphonyl}-2-methylpropanoate Obtained as a colourless, amorphous solid (96%), from the title compound of Preparation 159, using the procedure of Preparation 90. $\delta(CDCl_3)$: 1.64 (s,6H), 1.72 (s,6H), 1.78–1.88 (m,4H), 2.27 (s,3H), 2.63 (m,1H), 3.09 (m,2H), 3.81 (s,3H), 3.98 (d,2H), 6.68–6.77 (m,3H), 7.07 (m,2H), 7.17 (d,1H).

LRMS (Thermospray): 488 (M+H)⁺.

PREPARATION 161

2-{4-[4-(2,2-Dimethyl-1,3-benzodioxol-5-yl)-3-methylphenyl]piperidin-1-ylsulphonyl}-2-methylpropanoic acid Obtained as a colourless, amorphous solid (47%) from the title compound of Preparation 160, using the procedure of Preparation 79. $\delta(CDCl_3)$: 1.67 (s,6H), 1.72 (s,6H), 1.78–1.88 (m,4H), 2.27 (s,3H), 2.63 (m,1H), 3.10 (m,2H), 4.00 (d,2H), 6.68–6.77 (m,3H), 7.05 (m,2H), 7.16 (d,1H).

LRMS (Thermospray): 474 (M+H)⁺.

PREPARATION 162

1,2-Dimethyl-5-(4,4,5 5-tetramethyl-1,3,2-dioxaborolan-2-yl)benzimidazole

A mixture of 5-bromo-1,2-dimethylbenzimidazole (J. Chem. Soc., 1931, 1143; 2 g, 8.88 mmol), 4,4,5,5-tetramethyl-1,3,2-dioxaborolane (2.06 ml, 14 mmol), triethylamine (3.9 ml, 28 mmol), [1,1'-bis(diphenylphosphino)ferrocene]dichloro palladium(II) (224 mg, 0.27 mmol) and anhydrous 1,4-dioxan (35 ml), under nitrogen, was stirred under reflux for 44 hours, then allowed to cool and partitioned between ethyl acetate and water. This mixture was filtered to remove palladium residues, the layers separated and the aqueous phase washed with ethyl acetate. The combined organic solutions were dried ($MgSO_4$) and evaporated under reduced pressure, then the residue was purified by flash chromatography, using methanol:dichloromethane (1:3) as eluant, followed by trituration with diisopropyl ether, to provide the title compound (356 mg, 15%) as a colourless, amorphous solid. $\delta(CDCl_3)$: 1.37 (s,12H), 2.60 (s,3H), 3.72 (s,3H), 7.27 (d,1H), 7.70 (d,1H), 8.15 (s,1H).

LRMS (Thermospray): 273 (M+H)⁺.

PREPARATION 163

Methyl 2-{4-[4-(1,2-dimethylbenzimidazol-5-yl)-3-methylphenyl]-1,2,3,6-tetrahydropyridin-1-ylsulphonyl}-2-methylpropanoate To a stirred solution of the title compound of Preparation 40 (400 mg, 0.96 mmol) in degassed 1,2-dimethoxyethane (20 ml) was added the title compound of Preparation 162 (351 mg, 1.29 mmol), cesium fluoride (380 mg, 2.5 mmol), tri-o-tolylphosphine (31 mg, 0.1 mmol) and tris (dibenzylideneacetone)dipalladium(0) (47 mg, 0.05 mmol), then the reaction mixture heated under reflux for about 3 hours, under nitrogen. Because of limited solubility, a portion of 1-methylpyrrolidin-2-one (4 ml) was added and the resulting mixture refluxed for 9 hours, then allowed to cool to room temperature, diluted with ethyl acetate, washed with water, dried ($MgSO_4$) and evaporated under reduced pressure. The residue was purified by flash chromatography, using an elution gradient of methanol:dichloromethane (0:100 to 2:98), followed by crystallisation from diisopropyl ether, to furnish the title compound (261 mg, 56%) as a colourless solid, m.p. 148–151° C. $\delta(CDCl_3)$: 1.67 (s,6H), 2.30 (s,3H), 2.63 (s,3H), 2.67 (m,2H), 3.63 (m,2H), 3.77 (s,3H), 3.81 (s,3H), 4.13 (m,2H), 6.07 (brs,1H), 7.19–7.32 (m,5H), 7.62 (s,1H).

LRMS (Thermospray): 482 $(M+H)^+$.

PREPARATION 164

Methyl 2-{4-[4-(1,2-dimethylbenzimidazol-5-yl)-3-methylphenyl]piperidin-1-ylsulphonyl}-2-methylpropanoate Obtained as a pale yellow gum (32%), from the title compound of Preparation 163, using the procedure of Preparation 90, except that the hydrogenation was conducted at 414 kPa (60 psi) and 70° C. for 24 hours and methanol:dichloromethane (3:97) was used as chromatography eluant. $\delta(CDCl_3)$: 1.65 (s,6H), 1.78–1.88 (m,4H), 2.27 (s,3H), 2.62 (s,3H), 2.65 (m,1H), 3.09 (m,2H), 3.75 (s,3H), 3.81 (s,3H), 3.97 (m,2H), 7.05–7.32 (m,5H), 7.61 (s,1H).

LRMS (Thermospray): 484 $(M+H)^+$.

PREPARATION 165

2-{4-[4-(1,2-Dimethylbenzimidazol-5-yl)-3-methylphenyl]piperidin-1-ylsulphonyl}-2-methylpropanoic acid Obtained as a colourless solid (88%), m.p. 125–127° C., from the title compound of Preparation 164, using the procedure of Preparation 91. $\delta(DMSO_{d6})$: 1.50 (s,6H), 1.62 (m,2H), 1.82 (m,2H), 2.20 (s,3H), 2.70 (m,1H), 2.78 (s,3H), 3.08 (t,2H), 3.81 (d,2H), 3.92 (s,3H), 7.10–7.20 (m,3H), 7.46 (d,1H), 7.65 (s,1H), 7.88 (d,1H).

LRMS (Thermospray): 471 $(M+H)^+$.

PREPARATION 166

2-[4-(4-Bromo-3-methylphenyl)-1,2,3 6-tetrahydropyridin-1 -ylsulphonyl]-2-methylpropanoic acid 1M Aqueous sodium hydroxide solution (4.2 ml, 4.2 mmol) was added to a stirred solution of the title compound of Preparation 40 (500 mg, 1.2 mmol) in a mixture of methanol (3 ml) and 1,4dioxan (3 ml). The resulting solution was heated at 50° C. for 2 hours, then allowed to cool to room temperature and poured into ethyl acetate. The mixture was washed with 2M hydrochloric acid, then the organic phase dried ($MgSO_4$) and evaporated under reduced pressure to afford the title compound (439 mg, 91%) as a colourless, amorphous solid. $\delta(CDCl_3)$: 1.67 (s,6H), 2.40 (s,3H), 2.58 (m,2H), 3.64 (t,2H), 4.11 (m,2H), 6.00 (brs,1H), 7.03 (d,1H), 7.21 (d,1H), 7.48 (d,1H).

LRMS (Electrospray): 425 $(M+Na)^+$.

PREPARATION 167

N-Benzyloxy 2-[4-(4-bromo-3-methylphenyl)-1,2,3,6-tetrahydropyridin-1-ylsulphonyl]-2-methylpropionamide 1-(3-Dimethylaminopropyl)-3-ethylcarbodiimide hydrochloride (274 mg, 1.43 mmol) was added to a stirred mixture of the title compound of Preparation 166 (439 mg, 1.19 mmol), N-hydroxybenzotriazole (176 mg, 1.3 mmol), O-benzylhydroxylamine hydrochloride (200 mg, 1.25 mmol), N-methylmorpholine (0.29 ml, 2.62 mmol) and anhydrous dichloromethane (8 ml). The reaction mixture was stirred at room temperature for 18 hours, diluted with dichloromethane, washed sequentially with dilute aqueous citric acid, water and aqueous sodium bicarbonate solution, dried ($MgSO_4$) and evaporated under reduced pressure. The residue was flash chromatographed, using an elution gradient of methanol:dichloromethane (1:99 to 2:98), to give the title compound (553 mg, 91%) as a colourless oil. $\delta(CDCl_3)$: 1.60 (s,6H), 2.40 (s,3H), 2.53 (m,2H), 3.58 (t,2H), 4.04 (m,2H), 4.93 (s,2H), 5.95 (brs,1H), 7.00 (d,1H), 7.20 (s,1H), 7.36–7.50 (m,6H), 9.20 (brs,1H).

LRMS (Electrospray): 531 $(M+Na)^+$.

PREPARATION 168

N-Benzyloxy 2-{4-[4-(3-cyanophenyl)-3-methylphenyl]-1,2,3,6-tetrahydropyridin-1-ylsulphonyl}-2-methylpropionamide Obtained as an amorphous solid (30%), from the title compound of Preparation 167 and 3-cyanophenylboronic acid (Arch. Pharm. 1996, 329, 73), using the procedure of Preparation 41, but using an elution gradient of ethyl acetate:pentane (10:90 to 50:50) for the flash chromatographic purification step. $\delta(CDCl_3)$: 1.60 (s,6H), 2.24 (s,3H), 2.61 (m,2H), 3.60 (t,2H), 4.08 (m,2H), 4.95 (s,2H), 6.03 (brs,1H), 7.15 ($d_{,1}$H), 7.25 (m,2H), 7.40 (m,5H), 7.55 (m,2H), 7.62 (m,2H), 9.20 (s,1H).

LRMS (Thermospray): 530 $(M+H)^+$.

PREPARATION 169

3-Ethoxy-5-(tri-n-butylstannyl)pyridine

A stirred mixture of 3-bromo-5-ethoxypyridine (Rec. Trav. chim., 1948, 67, 377; 930 mg, 4.6 mmol), bis(tri-n-butyltin) (3.46 ml, 6.9 mmol), tri-o-tolylphosphine (420 mg, 1.37 mmol), palladium(II) acetate (78 mg, 0.35 mmol), triethylamine (1.23 ml, 8.84 mmol) and acetonitrile (15 ml), under nitrogen, was heated under reflux for 18 hours, then allowed to cool. The solution was decanted from the black, tarry residue and evaporated under reduced pressure, then the resulting residue flash chromatographed, using an elution gradient of ethyl acetate:pentane (0:100 to 5:95), to yield the title compound (600 mg, 32%) as a colourless oil. $\delta(CDCl_3)$: 0.90 (t,9H), 1.08 (t,6H), 1.30–1.42 (m,6H), 1.42 (t,3H), 1.58 (m,6H), 4.08 (q,2H), 7.25 (s,1H), 8.17 (s,1H), 8.19 (s,1H).

PREPARATION 170

Methyl 2-{4-[4-(3-ethoxypyridin-5-yl)-3-methylphenyl]-1,2,3,6-tetrahydropyridin-1-ylsulphonyl}-2-methylpropanoate Obtained as a gum (30%), from the title compounds of Preparation 169 and Preparation 40, using the procedure of Preparation 89. $\delta(CDCl_3)$: 1.46 (t,3H), 1.68 (s,6H), 2.28 (s,3H), 2.65 (m,2H), 3.63 (m,2H), 3.81 (s,3H), 4.10 (m,4H), 6.08 (brs,1H), 7.12 (s,1H), 7.20 (d,1H), 7.28 (m,2H), 8.18 (s,1H) (s,1H).

LRMS (APCI): 459 $(M+H)^+$.

PREPARATION 171

Methyl 2-{4-[4-(3-ethoxypyridin-5-yl)-3-methylphenyl]piperidin-1-ylsulphonyl}-2-methylpropanoate Obtained as a colourless solid (88%), m.p. 110–112° C., from the title compound of Preparation 170, using the procedure of Preparation 66. Found: C, 62.24;H, 6.96; N, 5.97. $C_{24}H_{32}N_2O_5S$ requires C, 62.59; H, 7.00; N, 6.08%. δ($CDCl_3$): 1.44 (t,3H), 1.67 (s,6H), 1.82 (m,2H), 1.89 (m,2H), 2.28 (s,3H), 2.67 (m,1H), 3.08 (m,2H), 3.81 (s,3H), 3.96 (m,2H), 4.12 (q,2H), 7.10–7.20 (m,4H), 8.17 (s,1H), 8.27 (s,1H).

LRMS (Electrospray): 461 $(M+H)^+$.

PREPARATION 172

2-{4-[4-(3-ethoxypyridin-5-yl)-3-methylphenyl] piperidin-1-ylsulphonyl}-2-methyl-propanoic acid Obtained as a colourless solid (98%), m.p. 202–203° C., from the title compound of Preparation 171, using the procedure of Preparation 91. δ($CDCl_3$): 1.44 (t,3H), 1.70 (s,6H), 1.80 (m,4H), 2.18 (s,3H), 2.60 (m,1H), 3.08 (m,2H), 3.96 (m,2H), 4.13 (q,2H), 7.05–7.15 (m,3H), 7.26 (obscured by $CHCl_3$, 1H), 8.22 (s,1H), 8.33 (s,1H).

LRMS (Thermospray): 447 $(M+H)^+$.

PREPARATION 173

3-(2-Hydronxyethoxy)bromobenzene

Anhydrous potassium carbonate (18.0 g, 130 mmol) was added to a stirred solution of 3-bromophenol (6.0 ml, 52 mmol) in anhydrous dimethylformamide (120 ml) and the mixture was heated under reflux for 45 minutes, then allowed to cool to about 50° C. 2-Bromoethanol (3.1 ml, 43 mmol) was added and the reaction mixture heated under reflux for a further 2 hours, before being allowed to slowly cool to room temperature. The resulting mixture was poured into ether, the mixture washed with water and the organic phase dried ($MgSO_4$) and evaporated under reduced pressure. The residue was purified by flash chromatography, using an elution gradient of pentane:ethyl acetate (10:1 to 5:1), to provide the title compound as a colourless oil (6.4 g, 57%). δ($CDCl_3$): 1.98 (t,1H), 3.95 (t,2H), 4.07 (m,2H), 6.87 (d,1H), 7.08–7.17 (m,3H).

PREPARATION 174

3-(2-t-Butyldiphenylsilyloxyethoxy)bromobenzene

Triethylamine (1.7 ml, 9.2 mmol) was added to a stirred solution of the title compound of Preparation 173 (1.8 g, 8.2 mmol) in anhydrous dimethylformamide (30 ml) and the mixture was cooled to about 0° C. t-Butyldiphenylsilyl chloride (2.4 ml, 9.2 mmol) was added and the reaction mixture stirred at 0° C. for 1 hour and at room temperature for about 16 hours, then poured into ether. The resulting mixture was washed with 0.5M hydrochloric acid, then the aqueous washings back-washed with ether. The combined organic solutions were washed with water, dried ($MgSO_4$) and evaporated under reduced pressure, then the residue purified by flash chromatography, using an elution gradient of pentane:dichloromethane (3:1 to 2:1 to 1:1), to furnish the title compound as a colourless oil (2.2 g, 62%). δ($CDCl_3$): 1.10 (s,9H), 4.00 (t,2H), 4.08 (t,2H), 6.82 (m,1H), 7.03–7.29 (m,4H), 7.38–7.48 (m,5H), 7.71 (m,4H).

LRMS (Thermospray): 474 $(M+NH_4)^+$.

PREPARATION 175

3-(2-t-Butyldiphenylsilyloxyethoxy)phenylboronic acid n-Butyllithium (2.3ml of a 2.5M solution in hexane, 5.9 mmol) was added to a stirred solution of the title compound of Preparation 174 (2.5 g, 5.6 mmol) in anhydrous tetrahydrofuran (25 ml), keeping the internal temperature below −60° C. The reaction mixture was stirred at about −70° C. for 1 hour, then trimethylborate (4.4 ml, 38 mmol) was added dropwise, again keeping the internal temperature below −60° C. The reaction mixture was stirred at −70° C. for 30 min, allowed to slowly warm to room temperature, quenched with a mixture of concentrated hydrochloric acid (12.5 ml) and water (30 ml), then ether (30 ml) added. The layers were separated and the aqueous layer was washed with ether. The combined organic solutions were dried ($MgSO_4$) and evaporated under reduced pressure, then the residue purified by flash chromatography, using ether as eluant, to afford the title compound as a colourless oil (1.14 g, 50%). δ($CDCl_3$): 1.08 (s,9H), 4.06 (t,2H), 4.19 (t,2H), 7.12 (m,1H), 7.36–7.45 (m,8H), 7.74 (m,6H), 7.82 (m,1H).

LRMS (Thermospray): 438 $(M+NH_4)^+$.

PREPARATION 176

Methyl 2-{4-[4(3-[2-t-butyldiphenylsilyloxyethoxy] phenyl)-3-methylphenyl]-1,2,3,6-tetrahydropyridin-1-ylsulphonyl}-2-methylpropionate Obtained as an oil (73%), from the title compounds of Preparation 175 and Preparation 40, using the procedure of Preparation 41, except that purification by flash chromatography involved an elution gradient of pentane:ethyl acetate (10:1 to 5:1). δ($CDCl_3$): 1.07 (s,9H), 1.67 (s,6H), 2.28 (s,3H), 2.65 (m,2H), 3.62 (m,2H), 3.81 (s,3H), 4.02 (m,2H), 4.08–4.16 (m,4H), 6.08 (brs,1H), 6.90 (m,3H), 7.19–7.42 (m,10H), 7.71 (d,4H).

LRMS (Thermospray): 438 $(M+NH_4)^+$.

PREPARATION 177

Methyl 2-{4-[4-(3-[2-t-butyldiphenylsilyloxyethoxy] phenyl)-3-methylphenyl]piperidin-1-ylsulphonyl}-2-methylpropanoate Obtained as a colourless oil (88%), from the title compound of Preparation 176, using the procedure of Preparation 66. δ($CDCl_3$): 1.07 (s,9H), 1.67 (s,6H), 1.80–1.95 (m,4H), 2.28 (s,3H), 2.65 (m,1H), 3.10 (t,2H), 3.81 (s,3H), 3.95 (m,2H), 3.97 (t,2H), 4.11 (t,2H), 6.86 (m,3H), 7.10 (m,2H), 7.19 (d,1H), 7.34–7.47 (m,6H), 7.71 (d,4H).

LRMS: (Thermospray): 438 $(M+NH_4)^+$.

PREPARATION 178

2-{4-[4-(3-[2-t-Butyldiphenylsilyloxyethoxy] phenyl)-3-methylphenyl]piperidin-1-ylsulphonyl}-2-methylpropanoic acid Obtained as a colourless foam (88%), from the title compound of Preparation 177, using the procedure of Preparation 79, but with the reaction being carried out at room temperature. δ($CDCl_3$): 1.07 (s,9H), 1.67 (s,6H), 1.78–1.95 (m,4H), 2.27 (s,3H), 2.65 (m,1H), 3.11 (t,2H), 3.97 (t,2H), 4.02 (m,2H), 4.11 (t,2H), 6.86 (m,3H), 7.10 (m,2H), 7.18 (d,1H), 7.30 (d,1H), 7.34–7.43 (m,6H), 7.71 (d,4H).

BIOLOGICAL ACTIVITY

The following Table illustrates the in vitro activities for a range of the compounds of the invention as MMP inhibitors.

TABLE

| EXAMPLE NO. | IC$_{50}$(nM) | | |
|---|---|---|---|
| | MMP-3 | MMP-2 | MMP-13 |
| 2 | 16 | 315 | 28 |
| 3 | 26 | 38 | 25 |
| 15 | 20 | 173 | NR |
| 28 | 24 | 432 | NR |
| 40 | 18 | 525 | NR |
| 50 | 23 | 1907 | NR |
| 56 | 15 | 387 | NR |

NR = no result

What is claimed is:

1. A compound of formula (I):

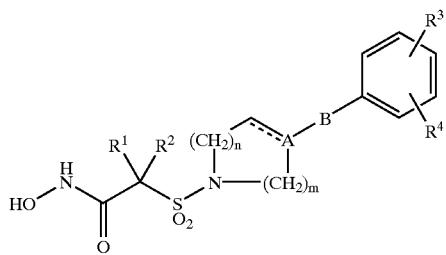

or a pharmaceutically or veterinarily acceptable salt thereof, or a pharmaceutically or veterinarily acceptable solvate of either entity,
wherein
the broken line represents an optional bond;
A is C or CH;
B is CH$_2$, O or absent;
R$^1$ and R$^2$ are each independently selected from hydrogen, C$_1$ to C$_6$ alkyl optionally substituted with C$_1$ to C$_4$ alkoxy or phenyl, and C$_1$ to C$_6$ alkenyl; or, together with the carbon atom to which they are attached, form a C$_3$ to C$_6$ cycloalkyl group which optionally incorporates a heteroatom linkage selected from O, SO, SO$_2$ and
NR$^6$ or which is optionally benzo-fused;
R$^3$ is hydrogen, halo, R$^7$ or OR$^7$;
R$^4$ is hydrogen, C$_1$ to C$_4$ alkyl, C$_1$ to C$_4$ alkoxy, trifluoromethyl or halo;
R$^6$ is hydrogen or C$_1$ to C$_4$ alkyl;
R$^7$ is a monocyclic or bicyclic ring system selected from phenyl, thienyl, furyl, pyridinyl, pyrimidinyl, naphthyl, indanyl, benzothienyl, benzofuranyl, 2,3-dihydrobenzofuranyl, indolyl, quinolinyl, isoquinolinyl, benzodioxolyl, benzimidazolyl, benzoxazolyl, benzothiazolyl and benzodioxanyl, any of which ring systems is optionally substituted with one or two substituents selected from C$_1$ to C$_4$ alkyl optionally substituted with C$_1$ to C$_4$ alkoxy or hydroxy, C$_1$–C$_4$ alkoxy optionally substituted with C$_1$ to C$_4$ alkoxy or hydroxy, C$_1$ to C$_4$ alkylthio, trifluoromethyl, trifluoromethoxy, halo and cyano;
m is 1 or 2; and
n is 0, 1 or 2;
with the proviso that B is not O when A is C.

2. A compound according to claim 1 wherein B is absent; R$^1$ is hydrogen, C$_1$ to C$_4$ alkyl optionally substituted with methoxy or phenyl, or C$_1$ to C$_5$ alkenyl; R$^2$ is hydrogen or C$_1$ to C$_4$ alkyl; or R$^1$ and R$^2$, together with the carbon atom to which they are attached, form a C$_4$ to C$_5$ cycloalkyl group which optionally incorporates a heteroatom linkage selected from O and NR$^6$ or which is optionally benzo-fused; R$^3$ is selected from 4-phenyl, 4-pyridinyl, 4-(indan-5-yl), 4-(2,3-dihydrobenzofuran-5-yl), 4-(quinolin-3-yl), 4-(benzodioxol-5-yl) and 4-(benzimidazol-5-yl), any of which is optionally substituted with one or two substituents selected from C$_1$ to C$_3$ alkyl optionally substituted with methoxy or hydroxy, C$_1$ to C$_3$ alkoxy optionally substituted with methoxy or hydroxy, methylthio, trifluoromethyl, trifluoromethoxy, fluoro, chloro and cyano; R$^4$ is hydrogen, methyl, ethyl, methoxy, trifluoromethyl, fluoro or chloro; R$^6$ is methyl; m is 2; and n is 1.

3. A compound according to claim 2 wherein R$^1$ is hydrogen, methyl, ethyl, 2-methylprop-1-yl, but-1-yl, 2-methoxyethyl, benzyl, 3-phenylprop-1-yl, allyl, 2-methylallyl, or 3,3-dimethylallyl; R$^2$ is hydrogen, methyl or ethyl; or R$^1$ and R$^2$, together with the carbon atom to which they are attached, form a cyclobutyl, cyclopentyl, tetrahydropyran-4,4diyl, 1-methylpiperidin-4,4-diyl or indan-2,2-diyl group; R$^3$ is 4-phenyl, 4-(2-methylphenyl), 4-(3-methylphenyl), 4-(3-ethylphenyl), 4-[3-(prop-2-yl)phenyl], 4-(3,5-dimethylphenyl), 4-(3-methoxymethylphenyl), 4-(3-hydroxymethylphenyl), 4-(2-methoxyphenyl), 4-(3-methoxyphenyl), 4-(3-ethoxyphenyl), 4-(4-ethoxyphenyl), 4-[3-(prop-1-oxy)phenyl], 4-[3-(prop-2-oxy)phenyl], 4-[4-(prop-2-oxy)phenyl], 4-(3,4-dimethoxyphenyl), 4-[3-(2-methoxyethoxy)phenyl], 4-[3-(2-hydroxyethoxy)phenyl], 4-(3-methylthiophenyl), 4-(3-trifluoromethylphenyl), 4-(3-trifluoromethoxyphenyl), 4-(2-fluorophenyl), 4-(3-chloro-4-fluorophenyl), 4-(3-cyanophenyl), 4-(pyridin-2-yl), 4-(pyridin-3-yl), 4-(pyridin4-yl), 4-(6-ethoxypyridin-2-yl), 4-(5-ethoxypyridin-3-yl), 4-(indan-5-yl), 4-(2,3-dihydrobenzofuran-5-yl), 4-(quinolin-3-yl), 4-(benzodioxol-5-yl), 4-(2,2-dimethylbenzodioxol-5-yl) and 4-(1,2-dimethylbenzimidazol-5-yl); or R$^4$ is hydrogen, 2-methyl, 3-methyl, 3-ethyl, 3-methoxy, 3-trifluoromethyl, 3-fluoro or 3-chloro.

4. A compound according to claim 3 wherein R$^1$ and R$^2$ are both hydrogen or methyl or, together with the carbon atom to which they are attached, form a cyclobutyl, cyclopentyl, tetrahydropyran-4,4-diyl or 1-methylpiperidin-4,4-diyl group; R$^3$ is 4-phenyl, 4-(3-methoxyphenyl), 4-(3-ethoxyphenyl), 4-[3-(2-methoxyethoxy)phenyl], 4-[3-(2-hydroxyethoxy)phenyl] or 4-(6-ethoxypyridin-2-yl); and R$^4$ is 3-methyl or 3-methoxy.

5. A compound according to claim 4 wherein the compound of formula (I) is selected from N-hydroxy-2-{4-[4-(3-ethoxyphenyl)-3-methylphenyl]-1,2,3,6-tetrahydropyridin-1-ylsulphonyl}acetamide;

N-hydroxy-2-{4-[4-(3-ethoxyphenyl)-3-methylphenyl]-1,2,3,6-tetrahydropyridin-1-ylsulphonyl}-2-methylpropanamide;

N-hydroxy-2-{4-[4-(3-ethoxyphenyl)-3-methylphenyl]piperidin-1-ylsulphonyl}-2-methylpropanamide;

N-hydroxy-1-{4-[4-(3-methoxyphenyl)-3-methylphenyl]piperidin-1-ylsulphonyl}cyclopentanecarboxamide;

N-hydroxy-1-{4-[4-(3-methoxyphenyl)-3-methylphenyl]piperidin-1-ylsulphonyl}cyclobutanecarboxamide;

N-hydroxy-2-{4-[4-(3-ethoxyphenyl)-3-methoxyphenyl]piperidin-1-ylsulphonyl}-2-methylpropanamide;

N-hydroxy-2-{4-[4-(6-ethoxypyridin-2-yl)-3-methylphenyl]piperidin-1-ylsulphohyl}-2-methylpropanamide;

N-hydroxy-2-{4-[4-(3-[2-methoxyethoxy]phenyl)-3-methylphenyl]-piperidin-1-ylsulphonyl}-2-methylpropanamide; and N-hydroxy-2-{4-[4-(3-[2-hydroxyethoxy]phenyl)-3-methylphenyl]piperidine-1-ylsulphonyl}-2-methylpropanamide.

6. A pharmaceutical composition comprising a compound of formula (I), or a pharmaceutically acceptable salt thereof, or a pharmaceutically acceptable solvate of either entity, according to claim 1, together with a pharmaceutically acceptable diluent or carrier.

7. A veterinary formulation comprising a compound of formula (I), or a veterinarily acceptable salt thereof, or a veterinarily acceptable solvate of either entity, according to claim 1, together with a veterinarily acceptable diluent or carrier.

8. A compound of formula (II):

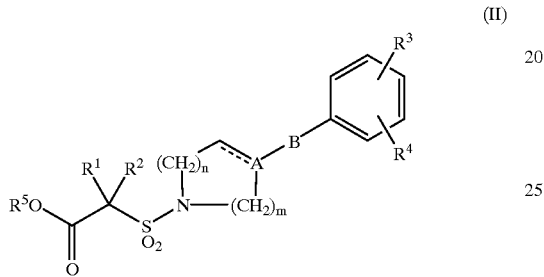

(II)

wherein $R^5$ is hydrogen or $C_1$ to $C_3$ alkyl, and the broken line, A,B, $R^1$, $R^2$, $R^3$, $R^4$, m and n are as previously defined for formula (I) in claim 1.

9. A method of treating a pathological condition which requires inhibition of MMP in a mammal comprises administering to said mammal a therapeutically effective amount of a compound of formula (I), or a pharmaceutically or veterinarily acceptable salt thereof, or a pharmaceutically or veterinarily acceptable solvate of either entity, according to claim 1.

10. A method according to claim 9 wherein the inhibitor is a MMP-3 inhibitor.

11. A method of treating a pathological condition of claim 9, said condition is selected from atherosclerotic plaque rupture, myocardial infarction, heart failure, restenosis, stroke, periodontal disease, tissue ulceration, wound repair, skin diseases, cancer metastasis, tumor angiogenesis, age-related macular degeneration, fibrotic disease, rheumatoid arthritis, osteoarthritis and inflammatory diseases dependent on migratory inflammatory cells.

12. A process for the preparation of a compound of formula (I):

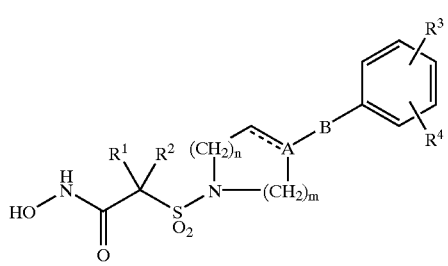

(I)

or a pharmaceutically or veterinarily acceptable salt thereof, or a pharmaceutically or veterinarily acceptable solvate of either entity, wherein
the broken line represents an optional bond;
A is C or CH;
B is $CH_2$, O or absent;
$R^1$ and $R^2$ are each independently selected from hydrogen, $C_1$ to $C_6$ alkyl optionally substituted with $C_1$ to $C_4$ alkoxy or phenyl, and $C_1$ to $C_6$ alkenyl; or, together with the carbon atom to which they are attached, form a $C_3$ to $C_6$ cycloalkyl group which optionally incorporates a heteroatom linkage selected from O, SO, $SO_2$ and
$NR^6$ or which is optionally benzo-fused;
$R^3$ is hydrogen, halo, $R^7$ or $OR^7$;
$R^4$ is hydrogen, $C_1$ to $C_4$ alkyl, $C_1$ to $C_4$ alkoxy, trifluoromethyl or halo;
$R^6$ is hydrogen or $C_1$ to $C_4$ alkyl;
$R^7$ is a monocyclic or bicyclic ring system selected from phenyl, thienyl, furyl, pyridinyl, pyrimidinyl, naphthyl, indanyl, benzothienyl, benzofuranyl, 2,3-dihydrobenzofuranyl, indolyl, quinolinyl, isoquinolinyl, benzodioxolyl, benzimidazolyl, benzoxazolyl, benzothiazolyl and benzodioxanyl, any of which ring systems is optionally substituted with one or two substituents selected from $C_1$ to $C_4$ alkyl optionally substituted with $C_1$ to $C_4$ alkoxy or hydroxy, $C_1$–$C_4$ alkoxy optionally substituted with $C_1$ to $C_4$ alkoxy or hydroxy, $C_1$ to $C_4$ alkylthio, trifluoromethyl, trifluoromethoxy, halo and cyano;
m is 1 or 2; and
n is 0, 1 or 2;
with the proviso that B is not O when A is C;
which comprises reacting a compound of formula (II):

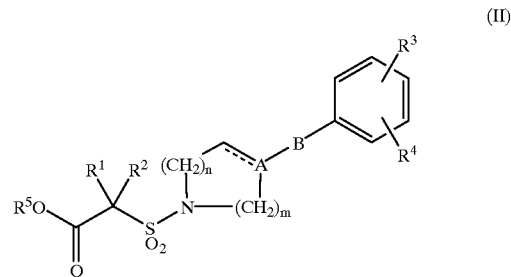

(II)

wherein $R^5$ is hydrogen or $C_1$ to $C_3$ alkyl, and the broken line, A,B, $R^1$, $R^2$, $R^3$, $R^4$, m and n are as previously defined for formula (I), with hydroxylamine, optionally followed by formation of a pharmaceutically or veterinarily acceptable salt of the required product or a pharmaceutically or veterinarily acceptable solvate of either entity.

13. A process according to claim 12 wherein, when $R^5$ is $C_1$ to $C_3$ alkyl, the ester of formula (II) is treated with up to a 3-fold excess of hydroxylamine hydrochloride in the presence of a molar equivalent amount of a suitable base in a suitable solvent at from about room temperature to about 85° C.

14. A process according to claim 13 wherein the base is an alkali metal carbonate or bicarbonate, the solvent is methanol, optionally combined with tetrahydrofuran or dichloromethane as co-solvent, and the reaction temperature is from about 65 to about 70° C.

15. A process according to claim 12 wherein, when $R^5$ is hydrogen, the acid of formula (II) in the presence of from 1.1 to 2.0 molecular equivalents of an activating agent and from 1.0 to 4.0 molecular equivalents of a tertiary amine, in a suitable solvent, is treated with up to about a 3-fold excess of hydroxylamine hydrochloride, optionally in the same solvent, at from about 0° C. to about room temperature.

16. A process according to claim 15 wherein the activating agent is O-(7-azabenzotriazol-1-yl)-1,1,3,3-tetramethyluronium hexafluorophosphate (HATU), the tertiary amine is N-ethyldiisopropylamine, the solvent is anhydrous dimethylformamide or anhydrous 1-methylpyrrolidin-2-one and the reaction temperature is about room temperature.

* * * * *